United States Patent [19]
Cappello et al.

[11] Patent Number: 5,773,249
[45] Date of Patent: *Jun. 30, 1998

[54] HIGH MOLECULAR WEIGHT COLLAGEN-LIKE PROTEIN POLYMERS

[75] Inventors: Joseph Cappello, San Diego; Franco A. Ferrari, La Jolla, both of Calif.

[73] Assignee: Protein Polymer Technologies, Inc., San Diego, Calif.

[*] Notice: The term of this patent shall not extend beyond the expiration date of Pat. No. 5,496,712.

[21] Appl. No.: 642,255

[22] Filed: May 2, 1996

Related U.S. Application Data

[63] Continuation-in-part of Ser. No. 577,046, Dec. 22, 1995, which is a continuation of Ser. No. 972,032, Nov. 5, 1992, Pat. No. 5,496,712, which is a continuation-in-part of Ser. No. 791,960, Nov. 12, 1991, abandoned, which is a continuation-in-part of Ser. No. 609,716, Nov. 6, 1990, Pat. No. 5,514,581, which is a continuation-in-part of Ser. No. 269,429, Nov. 9, 1988, abandoned, which is a continuation-in-part of Ser. No. 114,618, Oct. 29, 1987, Pat. No. 5,243,038, which is a continuation-in-part of Ser. No. 927,258, Nov. 4, 1986, abandoned.

[51] Int. Cl.$^6$ .......................... C12P 21/02; C07K 14/435; C12N 15/12
[52] U.S. Cl. ..................... 435/69.1; 435/69.7; 435/252.3; 435/252.77; 530/356; 530/388.9; 530/389.8; 536/23.5
[58] Field of Search ..................................... 530/356, 350, 530/388.9, 389.8; 536/93.5; 435/252.3, 252.33, 69.1, 69.7

[56] References Cited

FOREIGN PATENT DOCUMENTS

| | | |
|---|---|---|
| WO/8803533 | 5/1988 | WIPO . |
| WO/8805082 | 7/1988 | WIPO . |
| WO/9005177 | 11/1988 | WIPO . |

OTHER PUBLICATIONS

Goldberg et al., "Cloning and Expression of a Collagen–Analog–Encoding Synthetic Gene in *E. coli*", Gene (1989), 80:305–314.

Kempe et al., "Multiple Copy Genes: Production and Modification of Monomeric Peptides From Large Multimeric Fusion Proteins", Gene (1985), 39:239–245.

Lennick et al., "High–Level Expression of A–Human Atrial Natriuretic Peptide From Multiple Joined Genes in *E. coli*", Gene (1987), 61:103–112.

Taylor and Hagerman, "A General Method for Cloning DNA Fragments in Multiple Copies", Gene (1987), 53:139–144.

Aslund et al., "Synthetic Gene Contruct Expression a Repeated and Highly Immunogenic", PNAS (1987), 84:1399–1403.

Schulz et al., "Increased Expression in *E. coli* of a Synthetic Gene Encoding Human Somatomedin C After Gene Duplication and Fusion", J. Bact. (1987), 169:5385–5392.

Kim and Szybalski, "Amplification of Cloned DNA as Tandem Multimers Using BspM1–Generated Asymmetric Cohesive Ends", Gene (1988), 7:1–8.

Takeshita et al., "Tandem Gene Amplification In Vitro for Rapid and Efficient Expression in Animal Cells", Gene (1988), 71:9–18.

Bressan et al., "Repeating Structure of Chick Tropoelastin Revealed By Complentary DNA Cloning", Biochemistry (1987), 26:1497–1503.

Shen, "Multiple Joined Genes Prevent Product Degradation in *E. coli.*", PNAS (1984), 81:4627–4631.

Doel et al., "The Expression in *E. coli* of Synthetic Repeating Polymeric Genes Coding for Poly)L–aspartyl–L–phenylalanine", Nucl. Acids. Res (1980), 8:4575–4592.

Hartley et al., "Cloning Multiple Copies of a DNA Segment", Gene (1981), 13:347–353.

Sadler et al., "Plasmids Containing Many Tandem Copies of a Synthetic Lactose Operator", Gene (1980), 8:279–300.

Fleishmajer et al., "Collagen Fibrillogenesis in Human Skin", Annals of the New York Academy of Sciences (1985), 260:246–257.

Miller, E.J. (1985) Ann. N.Y. Acad. Sci. 460,1–13.

*Primary Examiner*—Charles L. Patterson, Jr.
*Attorney, Agent, or Firm*—Flehr Hohbach Test Albritton and Herbert LLP; Richard F. Trecartin; Mark T. Kresnak

[57] ABSTRACT

Collagen-like polymers having repetitive triads are produced having reduced proline content, where glycine is the initial amino acid and the subsequent amino acids are varied, while retaining at least a minimum percentage of prolines. The resulting polymers have collagen-like properties, but are capable of being produced in unicellular microorganisms at high molecular weights and in high efficiency. The polymers, while retaining collagen-like characteristics, include various novel sequences which impart new characteristics, finding wide use in photographic, medical, structural and fiber applications.

32 Claims, No Drawings

SEQUENCE LISTING ( 1 ) GENERAL INFORMATION:

( i i i ) NUMBER OF SEQUENCES: 135

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Gly Ala Pro Gly Pro Ala Gly Pro Lys
   1               5

( 2 ) INFORMATION FOR SEQ ID NO:2:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Gly Ala Pro Gly Pro Ala Gly Pro Pro Gly Ala His
   1               5                   1 0

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Gly Ser Pro Gly Ala Pro Gly Pro Ala
   1               5

( 2 ) INFORMATION FOR SEQ ID NO:4:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Gly Ala Pro Gly Pro Ala Gly Ser Arg Gly Asp Pro Gly Pro Ala
   1               5                   1 0                  1 5

( 2 ) INFORMATION FOR SEQ ID NO:5:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear (ii) MOLECULE TYPE: peptide (xi) SEQUENCE DESCRIPTION: SEQ ID NO:5:

Gly Ala Asn Gly Ala Pro Gly Pro Ala Gly Pro Ala Gly Ala Pro Gly
1               5                   10                  15

Pro Pro (2) INFORMATION FOR SEQ ID NO:6:

(i) SEQUENCE CHARACTERISTICS:
      (A) LENGTH: 18 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:6:

Gly Ala Gln Gly Pro Ala Gly Pro Gly Gly Ala Pro Gly Pro Ala Gly
1               5                   10                  15

Pro Gly (2) INFORMATION FOR SEQ ID NO:7:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:7:

Gly Ala Pro Gly Pro Ala Gly Ala Ser
1               5

(2) INFORMATION FOR SEQ ID NO:8:

(i) SEQUENCE CHARACTERISTICS:
      (A) LENGTH: 18 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:8:

Gly Pro Ala Gly Ala Pro Gly Ser Arg Gly Asp Pro Gly Ala Pro Gly
1               5                   10                  15

Pro Pro (2) INFORMATION FOR SEQ ID NO:9:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:9:

Gly Val Ser Gly Pro Arg Gly Pro Ala Gly Ala Pro Gly Pro Pro
1               5                   10                  15

(2) INFORMATION FOR SEQ ID NO:10:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Gly Ala Gln Gly Pro Ala Gly Pro Gly
1                  5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Gly Ala His Gly Pro Ala Gly Pro Lys
1                  5

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Gly Ala His Gly Pro Ala Gly Pro Arg
1                  5

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Gly Ala Val Gly Ala Pro Gly Pro Lys
1                  5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Gly Pro Ala Gly Ala Pro Gly Glu Pro
1                  5

( 2 ) INFORMATION FOR SEQ ID NO:15:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

```
Gly  Val  Ser  Gly  Pro  Arg  Gly  Ala  Pro
1                   5
```

( 2 ) INFORMATION FOR SEQ ID NO:16:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Gly  Ala  His  Gly  Pro  Ala  Gly  Pro  Lys  Gly  Ala  His  Gly  Pro  Ala  Gly
1                   5                            10                            15
Pro  Lys  Gly  Ala  Pro  Gly  Pro  Ala  Gly  Pro  Pro  Gly  Ala  Pro  Gly  Pro
                    20                           25                            30
Ala  Gly  Pro  Pro
               35
```

( 2 ) INFORMATION FOR SEQ ID NO:17:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Gly  Ala  Pro  Gly  Pro  Ala  Gly  Pro  Pro  Gly  Ser  Arg  Gly  Asp  Pro  Gly
1                   5                            10                            15
Pro  Pro  Gly  Ala  Pro  Gly  Pro  Ala  Gly  Pro  Pro  Gly  Ser  Arg  Gly  Asp
                    20                           25                            30
Pro  Gly  Pro  Pro
               35
```

( 2 ) INFORMATION FOR SEQ ID NO:18:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Gly  Ala  Pro  Gly  Ala  Pro  Gly  Ser  Gln  Gly  Ala  Pro  Gly  Leu  Gln  Gly
1                   5                            10                            15
Ala  Pro  Gly  Ala  Pro  Gly  Ser  Gln  Gly  Ala  Pro  Gly  Leu  Gln  Tyr  Met
                    20                           25                            30
Lys
```

( 2 ) INFORMATION FOR SEQ ID NO:19:

( i ) SEQUENCE CHARACTERISTICS:
 ( A ) LENGTH: 21 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:19:

Gly Leu Pro Gly Pro Lys Gly Asp Arg Gly Asp Ala Gly Pro Lys Gly
1               5                   10                  15

Ala Asp Gly Ser Pro
                20

( 2 ) INFORMATION FOR SEQ ID NO:20:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:20:

AATTCGGTGC CCCTGGTCCG CCTGGTCCGC CTGGTCCACC GGGTCCTCCG GGGGCTC          57

( 2 ) INFORMATION FOR SEQ ID NO:21:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:21:

GCCACGGGGA CCAGGCGGAC CAGGCGGACC AGGTGGCCCA GGAGGCCCCC GAGCATG          57

( 2 ) INFORMATION FOR SEQ ID NO:22:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:22:

CCGGGTCCTC CAGGACCGCC AGGTCCGCCT GGTCCCCC          38

( 2 ) INFORMATION FOR SEQ ID NO:23:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:23:

CCGAGGCCCA GGAGGTCCTG GCGGTCCAGG CGGACCAGGG GG          42

( 2 ) INFORMATION FOR SEQ ID NO:24:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:24:

```
GGGTCCTGCA  GGTCCAGTAG  GTAGCCCCGG  TGCCATGTGT  GCGCATCGAT  ATC         53
```

( 2 ) INFORMATION FOR SEQ ID NO:25:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:25:

```
CCCAGGACGT  CCAGGTCATC  CATCGGGGCC  ACGGTACACA  CGCGTAGCTA  TAGAGCT     57
```

( 2 ) INFORMATION FOR SEQ ID NO:26:

( i ) SEQUENCE CHARACTERISTICS:
        ( A ) LENGTH: 123 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synethic"

( x i ) SEQUENCE DESCRIPTION: SEQ ID NO:26:

```
GGTGCCCCTG  GTCCGCCTGG  TCCGCCTGGT  CCACCGGGTC  CTCCGGGGGC  TCCGGGTCCT   60
CCAGGACCGC  CAGGTCCGCC  TGGTCCCCCG  GGTCCTGCAG  GTCCAGTAGG  TAGCCCCGGT  120
GCC                                                                     123
```

( 2 ) INFORMATION FOR SEQ ID NO:27:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Gly  Ala  Pro  Gly  Pro  Pro  Gly  Pro  Pro  Gly  Pro  Pro  Gly  Pro  Pro  Gly
 1              5                        10                       15
Ala  Pro  Gly  Pro  Pro  Gly  Pro  Pro  Gly  Pro  Pro  Gly  Pro  Pro  Gly  Pro
              20                       25                       30
Ala  Gly  Pro  Val  Gly  Ser  Pro  Gly  Ala
             35                       40
```

( 2 ) INFORMATION FOR SEQ ID NO:28:

( i ) SEQUENCE CHARACTERISTICS:
        ( A ) LENGTH: 63 base pairs (B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:28:

```
CCGGGACTGC CAGGCCCGAA AGGCGATCGT GGCGACGCCG GTCCTAAAGG CGCAGATGGC      60
AGC                                                                    63
```

(2) INFORMATION FOR SEQ ID NO:29:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:29:

```
GGCCCTGACG GTCCGGGCTT TCCGCTAGCA CCGCTGCGGC CAGGATTTCC GCGTCTACCG      60
TCGGGCC                                                                67
```

(2) INFORMATION FOR SEQ ID NO:30:

(i) SEQUENCE CHARACTERISTICS:
(A) LENGTH: 186 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:30:

```
GGTGCCCCTG GTCCGCCTGG TCCGCCTGGT CCACCGGGTC CTCCGGGGGC TCCGGGTCCT      60
CCAGGACCGC CAGGTCCGCC TGGTCCCCCG GGACTGCCAG GCCCGAAAGG CGATCGTGGC     120
GACGCCGGTC CTAAAGGCGC AGATGGCAGC CCGGGTCCTG CAGGTCCAGT AGGTAGCCCC     180
GGTGCC                                                                186
```

(2) INFORMATION FOR SEQ ID NO:31:

(i) SEQUENCE CHARACTERISTICS:
(A) LENGTH: 62 amino acids
(B) TYPE: amino acid
(C) STRANDEDNESS: double
(D) TOPOLOGY: linear (ii) MOLECULE TYPE: peptide (xi) SEQUENCE DESCRIPTION: SEQ ID NO:31:

```
Gly Ala Pro Gly Pro Pro Gly Pro Pro Gly Pro Pro Gly Pro Pro Gly
 1               5                  10                  15
Ala Pro Gly Pro Pro Gly Pro Pro Gly Pro Pro Gly Pro Pro Gly Leu
            20                  25                  30
Pro Gly Pro Lys Gly Asp Arg Gly Asp Ala Gly Pro Lys Gly Ala Asp
        35                  40                  45
Gly Ser Pro Gly Pro Ala Gly Pro Val Gly Ser Pro Gly Ala
    50                  55                  60
```

(2) INFORMATION FOR SEQ ID NO:32:

( i ) SEQUENCE CHARACTERISTICS:
- ( A ) LENGTH: 330 amino acids
- ( B ) TYPE: amino acid
- ( C ) STRANDEDNESS: single
- ( D ) TOPOLOGY: linear ( i i ) MOLECULE TYPE: protein ( x i ) SEQUENCE DESCRIPTION: SEQ ID NO:32:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
             20                  25                  30

Met Gly Ala Pro Gly Pro Pro Gly Pro Pro Gly Pro Pro Gly Pro Pro
         35                  40                  45

Gly Ala Pro Gly Pro Pro Gly Pro Pro Gly Pro Pro Gly Pro Pro Gly
     50                  55                  60

Pro Ala Gly Pro Val Gly Ser Pro Gly Ala Pro Gly Pro Pro Gly Pro
 65                  70                  75                  80

Pro Gly Pro Pro Gly Pro Pro Gly Ala Pro Gly Pro Pro Gly Pro Pro
                 85                  90                  95

Gly Pro Pro Gly Pro Pro Gly Pro Ala Gly Pro Val Gly Ser Pro Gly
                 100                 105                 110

Ala Pro Gly Pro Pro Gly Pro Pro Gly Pro Pro Gly Pro Pro Gly Ala
         115                 120                 125

Pro Gly Pro Pro Gly Pro Pro Gly Pro Pro Gly Pro Pro Gly Pro Ala
     130                 135                 140

Gly Pro Val Gly Ser Pro Gly Ala Pro Gly Pro Pro Gly Pro Pro Gly
145                  150                 155                 160

Pro Pro Gly Pro Pro Gly Ala Pro Gly Pro Pro Gly Pro Pro Gly Pro
                 165                 170                 175

Pro Gly Pro Pro Gly Pro Ala Gly Pro Val Gly Ser Pro Gly Ala Pro
             180                 185                 190

Gly Pro Pro Gly Pro Pro Gly Pro Pro Gly Pro Pro Gly Ala Pro Gly
         195                 200                 205

Pro Pro Gly Pro Pro Gly Pro Pro Gly Pro Pro Gly Pro Ala Gly Pro
     210                 215                 220

Val Gly Ser Pro Gly Ala Pro Gly Pro Pro Gly Pro Pro Gly Pro Pro
225                  230                 235                 240

Gly Pro Pro Gly Ala Pro Gly Pro Pro Gly Pro Pro Gly Pro Pro Gly
                 245                 250                 255

Pro Pro Gly Pro Ala Gly Pro Val Gly Ser Pro Gly Ala Pro Gly Pro
             260                 265                 270

Pro Gly Pro Pro Gly Pro Pro Gly Pro Pro Gly Pro Ala Pro Gly Pro Pro
         275                 280                 285

Gly Pro Pro Gly Pro Pro Gly Pro Pro Gly Pro Ala Gly Pro Val Gly
     290                 295                 300

Ser Pro Gly Ala Met Cys Ala His Arg Tyr Gln Leu Ser Ala Gly Arg
305                  310                 315                 320

Tyr His Tyr Gln Leu Val Trp Cys Gln Lys
                 325                 330
```

( 2 ) INFORMATION FOR SEQ ID NO:33:

( i ) SEQUENCE CHARACTERISTICS:
- ( A ) LENGTH: 357 amino acids
- ( B ) TYPE: amino acid -continued (C) STRANDEDNESS: single
(D) TOPOLOGY: linear (ii) MOLECULE TYPE: protein (xi) SEQUENCE DESCRIPTION: SEQ ID NO:33:

| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |

| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |

| Met | Gly | Ala | Pro | Gly | Pro | Pro | Gly | Pro | Pro | Gly | Pro | Pro | Gly | Pro | Pro |
| | | 35 | | | | | 40 | | | | | 45 | | | |

| Gly | Ala | Pro | Gly | Pro | Pro | Gly | Pro | Pro | Gly | Pro | Pro | Gly | Pro | Pro | Gly |
| | 50 | | | | | 55 | | | | | 60 | | | | |

| Leu | Pro | Gly | Pro | Lys | Gly | Asp | Arg | Gly | Asp | Ala | Gly | Pro | Lys | Gly | Ala |
| 65 | | | | | 70 | | | | | 75 | | | | | 80 |

| Asp | Gly | Ser | Pro | Gly | Pro | Ala | Gly | Pro | Val | Gly | Ser | Pro | Gly | Ala | Pro |
| | | | | 85 | | | | | 90 | | | | | 95 | |

| Gly | Pro | Pro | Gly | Pro | Pro | Gly | Pro | Pro | Gly | Pro | Pro | Gly | Ala | Pro | Gly |
| | | | 100 | | | | | 105 | | | | | 110 | | |

| Pro | Pro | Gly | Pro | Pro | Gly | Pro | Pro | Gly | Pro | Pro | Gly | Leu | Pro | Gly | Pro |
| | | 115 | | | | | 120 | | | | | 125 | | | |

| Lys | Gly | Asp | Arg | Gly | Asp | Ala | Gly | Pro | Lys | Gly | Ala | Asp | Gly | Ser | Pro |
| | 130 | | | | | 135 | | | | | 140 | | | | |

| Gly | Pro | Ala | Gly | Pro | Val | Gly | Ser | Pro | Gly | Ala | Pro | Gly | Pro | Pro | Gly |
| 145 | | | | | 150 | | | | | 155 | | | | | 160 |

| Pro | Pro | Gly | Pro | Pro | Gly | Pro | Pro | Gly | Ala | Pro | Gly | Pro | Pro | Gly | Pro |
| | | | | 165 | | | | | 170 | | | | | 175 | |

| Pro | Gly | Pro | Pro | Gly | Pro | Pro | Gly | Leu | Pro | Gly | Pro | Lys | Gly | Asp | Arg |
| | | | 180 | | | | | 185 | | | | | 190 | | |

| Gly | Asp | Ala | Gly | Pro | Lys | Gly | Ala | Asp | Gly | Ser | Pro | Gly | Pro | Ala | Gly |
| | | 195 | | | | | 200 | | | | | 205 | | | |

| Pro | Val | Gly | Ser | Pro | Gly | Ala | Pro | Gly | Pro | Pro | Gly | Pro | Pro | Gly | Pro |
| | 210 | | | | | 215 | | | | | 220 | | | | |

| Pro | Gly | Pro | Pro | Gly | Ala | Pro | Gly | Pro | Pro | Gly | Pro | Pro | Gly | Pro | Pro |
| 225 | | | | | 230 | | | | | 235 | | | | | 240 |

| Gly | Pro | Pro | Gly | Leu | Pro | Gly | Pro | Lys | Gly | Asp | Arg | Gly | Asp | Ala | Gly |
| | | | | 245 | | | | | 250 | | | | | 255 | |

| Pro | Lys | Gly | Ala | Asp | Gly | Ser | Pro | Gly | Pro | Ala | Gly | Pro | Val | Gly | Ser |
| | | | 260 | | | | | 265 | | | | | 270 | | |

| Pro | Gly | Ala | Pro | Gly | Pro | Pro | Gly | Pro | Pro | Gly | Pro | Pro | Gly | Pro | Pro |
| | | 275 | | | | | 280 | | | | | 285 | | | |

| Gly | Ala | Pro | Gly | Pro | Pro | Gly | Pro | Pro | Gly | Pro | Pro | Gly | Pro | Pro | Gly |
| | 290 | | | | | 295 | | | | | 300 | | | | |

| Leu | Pro | Gly | Pro | Lys | Gly | Asp | Arg | Gly | Asp | Ala | Gly | Pro | Lys | Gly | Ala |
| 305 | | | | | 310 | | | | | 315 | | | | | 320 |

| Asp | Gly | Ser | Pro | Gly | Pro | Ala | Gly | Pro | Val | Gly | Ser | Pro | Gly | Ala | Met |
| | | | | 325 | | | | | 330 | | | | | 335 | |

| Cys | Ala | His | Arg | Tyr | Gln | Leu | Ser | Ala | Gly | Arg | Tyr | His | Tyr | Gln | Leu |
| | | | 340 | | | | | 345 | | | | | 350 | | |

| Val | Trp | Cys | Gln | Lys |
| | | 355 | | |

(2) INFORMATION FOR SEQ ID NO:34:

(i) SEQUENCE CHARACTERISTICS:

(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Gly Ala Pro Gly Pro Ala Gly Pro Pro
1               5

(2) INFORMATION FOR SEQ ID NO:35:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:35:

Gly Ser Arg Gly Asp Pro Gly Pro Pro
1               5

(2) INFORMATION FOR SEQ ID NO:36:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:36:

GTGCTGCGGA TGCTCGAGAT GGTGCATGCA TGTACATCCG AGTACTTCGA T          51

(2) INFORMATION FOR SEQ ID NO:37:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:37:

ATCGCCGTAC TCGGATGTAC ATGCATGCAC CATCTCGAGC ATCCGCA              47

(2) INFORMATION FOR SEQ ID NO:38:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:38:

CTACATGTGT TACACATCCC GTGC                                       24

(2) INFORMATION FOR SEQ ID NO:39:

(i) SEQUENCE CHARACTERISTICS:

(A) LENGTH: 28 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:39:

GCACGGGATC TGTAACACAT GTAGAGCC 28

(2) INFORMATION FOR SEQ ID NO:40:

(i) SEQUENCE CHARACTERISTICS:
(A) LENGTH: 59 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:40:

GTGCTCACGG CCCAGCAGGT CCGAAGGGCG CGCATGGCCC AGCAGGCCCG AAAGGTGCC 59

(2) INFORMATION FOR SEQ ID NO:41:

(i) SEQUENCE CHARACTERISTICS:
(A) LENGTH: 59 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:41:

GCACGGCACC TTTCGGGCCT GCTGGGCCAT GCGCGCCCTT CGGACCTGCT GGGCCGTGA 59

(2) INFORMATION FOR SEQ ID NO:42:

(i) SEQUENCE CHARACTERISTICS:
(A) LENGTH: 54 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:42:

GTGCCCATGG CCCAGCAGGA CCGAAAGGAG CTCACGGTCC GGCAGGTCCG AAAG 54

(2) INFORMATION FOR SEQ ID NO:43:

(i) SEQUENCE CHARACTERISTICS:
(A) LENGTH: 53 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:43:

GCACCTTTCG GACCTGCCGG ACCGTGAGCT CCTTTCGGTC CTGCTGGGCC ATG 53

(2) INFORMATION FOR SEQ ID NO:44:

(i) SEQUENCE CHARACTERISTICS:

(A) LENGTH: 108 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:44:

```
GGTGCTCACG GCCCAGCAGG TCCGAAGGGC GCGCATGGCC CAGCAGGCCC GAAAGGTGCC          60
CATGGCCCAG CAGGACCGAA AGGAGCTCAC GGTCCGGCAG GTCCGAAA                      108
```

(2) INFORMATION FOR SEQ ID NO:45:

(i) SEQUENCE CHARACTERISTICS:
(A) LENGTH: 36 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:45:

```
Gly Ala His Gly Pro Ala Gly Pro Lys Gly Ala His Gly Pro Ala Gly
 1               5                  10                  15
Pro Lys Gly Ala His Gly Pro Ala Gly Pro Lys Gly Ala His Gly Pro
            20                  25                  30
Ala Gly Pro Lys
            35
```

(2) INFORMATION FOR SEQ ID NO:46:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:46:

```
GTGCGCCTGG ACCGGCTGGT CCACCGGGTG CTCCGGGACC TGCAGGCCCG CCAG               54
```

(2) INFORMATION FOR SEQ ID NO:47:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:47:

```
GCACCTGGCG GGCCTGCAGG TCCCGGAGCA CCCGGTGGAC CAGCCGGTCC AGGC               54
```

(2) INFORMATION FOR SEQ ID NO:48:

(i) SEQUENCE CHARACTERISTICS:
(A) LENGTH: 432 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic"

( x i ) SEQUENCE DESCRIPTION: SEQ ID NO:48:

| | | | | | |
|---|---|---|---|---|---|
| GGTGCTCACG | GCCCAGCAGG | TCCGAAGGGC | GCGCATGGCC | CAGCAGGCCC | GAAAGGTGCG | 60 |
| CCTGGACCGG | CTGGTCCACC | GGGTGCTCCG | GGACCTGCAG | GCCCGCCAGG | TGCGCCTGGA | 120 |
| CCGGCTGGTC | CACCGGGTGC | TCCGGGACCT | GCAGGCCCGC | CAGGTGCGCC | TGGACCGGCT | 180 |
| GGTCCACCGG | GTGCTCCGGG | ACCTGCAGGC | CCGCCAGGTG | CGCCTGGACC | GGCTGGTCCA | 240 |
| CCGGGTGCTC | CGGGACCTGC | AGGCCCGCCA | GGTGCGCCTG | GACCGGCTGG | TCCACCGGGT | 300 |
| GCTCCGGGAC | CTGCAGGCCC | GCCAGGTGCG | CCTGGACCGG | CTGGTCCACC | GGGTGCTCCG | 360 |
| GGACCTGCAG | GCCCGCCAGG | TGCCCATGGC | CCAGCAGGAC | CGAAAGGAGC | TCACGGTCCG | 420 |
| GCAGGTCCGA | AA | | | | | 432 |

( 2 ) INFORMATION FOR SEQ ID NO:49:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Gly Ala His Gly Pro Ala Gly Pro Lys Gly Ala His Gly Pro Ala Gly
 1               5                  10                  15
Pro Lys Gly Ala Pro Gly Pro Ala Gly Pro Pro Gly Ala Pro Gly Pro
            20                  25                  30
Ala Gly Pro Pro Gly Ala Pro Gly Pro Ala Gly Pro Pro Gly Ala Pro
        35                  40                  45
Gly Pro Ala Gly Pro Pro Gly Ala Pro Gly Pro Ala Gly Pro Pro Gly
    50                  55                  60
Ala Pro Gly Pro Ala Gly Pro Pro Gly Ala Pro Gly Pro Ala Gly Pro
65                  70                  75                  80
Pro Gly Ala Pro Gly Pro Ala Gly Pro Pro Gly Ala Pro Gly Pro Ala
                85                  90                  95
Gly Pro Pro Gly Ala Pro Gly Pro Ala Gly Pro Pro Gly Ala Pro Gly
               100                 105                 110
Pro Ala Gly Pro Pro Gly Ala Pro Gly Pro Ala Gly Pro Pro Gly Ala
           115                 120                 125
His Gly Pro Ala Gly Pro Lys Gly Ala His Gly Pro Ala Gly Pro Lys
       130                 135                 140
```

( 2 ) INFORMATION FOR SEQ ID NO:50:

( i ) SEQUENCE CHARACTERISTICS:
        ( A ) LENGTH: 756 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:50:

| | | | | | |
|---|---|---|---|---|---|
| GGTGCTCACG | GCCCAGCAGG | TCCGAAGGGC | GCGCATGGCC | CAGCAGGCCC | GAAAGGTGCG | 60 |
| CCTGGACCGG | CTGGTCCACC | GGGTGCTCCG | GGACCTGCAG | GCCCGCCAGG | TGCGCCTGGA | 120 |
| CCGGCTGGTC | CACCGGGTGC | TCCGGGACCT | GCAGGCCCGC | CAGGTGCGCC | TGGACCGGCT | 180 |
| GGTCCACCGG | GTGCTCCGGG | ACCTGCAGGC | CCGCCAGGTG | CGCCTGGACC | GGCTGGTCCA | 240 |

| | | | | | |
|---|---|---|---|---|---|
|CCGGGTGCTC|CGGGACCTGC|AGGCCCGCCA|GGTGCGCCTG|GACCGGCTGG|TCCACCGGGT 300|
|GCTCCGGGAC|CTGCAGGCCC|GCCAGGTGCG|CCTGGACCGG|CTGGTCCACC|GGGTGCTCCG 360|
|GGACCTGCAG|GCCCGCCAGG|TGCGCCTGGA|CCGGCTGGTC|CACCGGGTGC|TCCGGGACCT 420|
|GCAGGCCCGC|CAGGTGCGCC|TGGACCGGCT|GGTCCACCGG|GTGCTCCGGG|ACCTGCAGGC 480|
|CCGCCAGGTG|CGCCTGGACC|GGCTGGTCCA|CCGGGTGCTC|CGGGACCTGC|AGGCCCGCCA 540|
|GGTGCGCCTG|GACCGGCTGG|TCCACCGGGT|GCTCCGGGAC|CTGCAGGCCC|GCCAGGTGCG 600|
|CCTGGACCGG|CTGGTCCACC|GGGTGCTCCG|GACCTGCAG|GCCCGCCAGG|TGCGCCTGGA 660|
|CCGGCTGGTC|CACCGGGTGC|TCCGGGACCT|GCAGGCCCGC|CAGGTGCCCA|TGGCCCAGCA 720|
|GGACCGAAAG|GAGCTCACGG|TCCGGCAGGT|CCGAAA| | 756|

( 2 ) INFORMATION FOR SEQ ID NO:51:

( i ) SEQUENCE CHARACTERISTICS:
        ( A ) LENGTH: 234 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Gly Ala Pro Gly Pro Ala Gly Pro Pro Gly Ala Pro Gly Pro Ala Gly
1               5                   10                  15
Pro Pro Gly Ala Pro Gly Pro Ala Gly Pro Pro Gly Ala Pro Gly Pro
            20                  25                  30
Ala Gly Pro Pro Gly Ala Pro Gly Pro Ala Gly Pro Pro Gly Ala Pro
                35                  40                  45
Gly Pro Ala Gly Pro Pro Gly Ala Pro Gly Pro Ala Gly Pro Pro Gly
        50                  55                  60
Ala Pro Gly Pro Ala Gly Pro Pro Gly Ala Pro Gly Pro Ala Gly Pro
65                  70                  75                  80
Pro Gly Ala Pro Gly Pro Ala Gly Pro Pro Gly Ala Pro Gly Pro Ala
                85                  90                  95
Gly Pro Pro Gly Ala Pro Gly Pro Ala Gly Pro Pro Gly Ala Pro Gly
            100                 105                 110
Pro Ala Gly Pro Pro Gly Ala Pro Gly Pro Ala Gly Pro Pro Gly Ala
        115                 120                 125
Pro Gly Pro Ala Gly Pro Pro Gly Ala Pro Gly Pro Ala Gly Pro Pro
    130                 135                 140
Gly Ala Pro Gly Pro Ala Gly Pro Pro Gly Ala Pro Gly Pro Ala Gly
145                 150                 155                 160
Pro Pro Gly Ala Pro Gly Pro Ala Gly Pro Pro Gly Ala Pro Gly Pro
                165                 170                 175
Ala Gly Pro Pro Gly Ala Pro Gly Pro Ala Gly Pro Pro Gly Ala Pro
            180                 185                 190
Gly Pro Ala Gly Pro Pro Gly Ala Pro Gly Pro Ala Gly Pro Pro Gly
        195                 200                 205
Ala Pro Gly Pro Ala Gly Pro Pro Gly Ala His Gly Pro Ala Gly Pro
    210                 215                 220
Lys Gly Ala His Gly Pro Ala Gly Pro Lys
225                 230
```

( 2 ) INFORMATION FOR SEQ ID NO:52:

( i ) SEQUENCE CHARACTERISTICS:

(A) LENGTH: 561 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:52:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |

| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |

| Met | Gly | Ala | His | Gly | Pro | Ala | Gly | Pro | Lys | Gly | Ala | His | Gly | Pro | Ala |
| | | 35 | | | | 40 | | | | | 45 | | | | |

| Gly | Pro | Lys | Gly | Ala | Pro | Gly | Pro | Ala | Gly | Pro | Pro | Gly | Ala | Pro | Gly |
| | 50 | | | | | 55 | | | | | 60 | | | | |

| Pro | Ala | Gly | Pro | Pro | Gly | Ala | Pro | Gly | Pro | Ala | Gly | Pro | Pro | Gly | Ala |
| 65 | | | | | 70 | | | | | 75 | | | | | 80 |

| Pro | Gly | Pro | Ala | Gly | Pro | Pro | Gly | Ala | Pro | Gly | Pro | Ala | Gly | Pro | Pro |
| | | | | 85 | | | | | 90 | | | | | 95 | |

| Gly | Ala | Pro | Gly | Pro | Ala | Gly | Pro | Pro | Gly | Ala | Pro | Gly | Pro | Ala | Gly |
| | | | 100 | | | | | 105 | | | | | 110 | | |

| Pro | Pro | Gly | Ala | Pro | Gly | Pro | Ala | Gly | Pro | Pro | Gly | Ala | Pro | Gly | Pro |
| | | 115 | | | | | 120 | | | | | 125 | | | |

| Ala | Gly | Pro | Pro | Gly | Ala | Pro | Gly | Pro | Ala | Gly | Pro | Pro | Gly | Ala | Pro |
| | 130 | | | | | 135 | | | | | 140 | | | | |

| Gly | Pro | Ala | Gly | Pro | Pro | Gly | Ala | Pro | Gly | Pro | Ala | Gly | Pro | Pro | Gly |
| 145 | | | | | 150 | | | | | 155 | | | | | 160 |

| Ala | Pro | Gly | Pro | Ala | Gly | Pro | Pro | Gly | Ala | Pro | Gly | Pro | Ala | Gly | Pro |
| | | | | 165 | | | | | 170 | | | | | 175 | |

| Pro | Gly | Ala | Pro | Gly | Pro | Ala | Gly | Pro | Pro | Gly | Ala | Pro | Gly | Pro | Ala |
| | | | 180 | | | | | 185 | | | | | 190 | | |

| Gly | Pro | Pro | Gly | Ala | Pro | Gly | Pro | Ala | Gly | Pro | Pro | Gly | Ala | Pro | Gly |
| | | 195 | | | | | 200 | | | | | 205 | | | |

| Pro | Ala | Gly | Pro | Pro | Gly | Ala | Pro | Gly | Pro | Ala | Gly | Pro | Pro | Gly | Ala |
| | 210 | | | | | 215 | | | | | 220 | | | | |

| Pro | Gly | Pro | Ala | Gly | Pro | Pro | Gly | Ala | Pro | Gly | Pro | Ala | Gly | Pro | Pro |
| 225 | | | | | 230 | | | | | 235 | | | | | 240 |

| Gly | Ala | Pro | Gly | Pro | Ala | Gly | Pro | Pro | Gly | Ala | Pro | Gly | Pro | Ala | Gly |
| | | | | 245 | | | | | 250 | | | | | 255 | |

| Pro | Pro | Gly | Ala | Pro | Gly | Pro | Ala | Gly | Pro | Pro | Gly | Ala | His | Gly | Pro |
| | | | 260 | | | | | 265 | | | | | 270 | | |

| Ala | Gly | Pro | Lys | Gly | Ala | His | Gly | Pro | Ala | Gly | Pro | Lys | Gly | Ala | His |
| | | 275 | | | | | 280 | | | | | 285 | | | |

| Gly | Pro | Ala | Gly | Pro | Lys | Gly | Ala | His | Gly | Pro | Ala | Gly | Pro | Lys | Gly |
| | 290 | | | | | 295 | | | | | 300 | | | | |

| Ala | Pro | Gly | Pro | Ala | Gly | Pro | Pro | Gly | Ala | Pro | Gly | Pro | Ala | Gly | Pro |
| 305 | | | | | 310 | | | | | 315 | | | | | 320 |

| Pro | Gly | Ala | Pro | Gly | Pro | Ala | Gly | Pro | Pro | Gly | Ala | Pro | Gly | Pro | Ala |
| | | | | 325 | | | | | 330 | | | | | 335 | |

| Gly | Pro | Pro | Gly | Ala | Pro | Gly | Pro | Ala | Gly | Pro | Pro | Gly | Ala | Pro | Gly |
| | | | 340 | | | | | 345 | | | | | 350 | | |

| Pro | Ala | Gly | Pro | Pro | Gly | Ala | Pro | Gly | Pro | Ala | Gly | Pro | Pro | Gly | Ala |
| | | 355 | | | | | 360 | | | | | 365 | | | |

| Pro | Gly | Pro | Ala | Gly | Pro | Pro | Gly | Ala | Pro | Gly | Pro | Ala | Gly | Pro | Pro |
| | 370 | | | | | 375 | | | | | 380 | | | | |

Gly Ala Pro Gly Pro Ala Gly Pro Pro Gly Ala Pro Gly Pro Ala Gly
385                     390                 395                 400

Pro Pro Gly Ala Pro Gly Pro Ala Gly Pro Pro Gly Ala Pro Gly Pro
            405                 410                 415

Ala Gly Pro Pro Gly Ala Pro Gly Pro Ala Gly Pro Pro Gly Ala Pro
            420                 425                 430

Gly Pro Ala Gly Pro Pro Gly Ala Pro Gly Pro Ala Gly Pro Pro Gly
        435                 440                 445

Ala Pro Gly Pro Ala Gly Pro Pro Gly Ala Pro Gly Pro Ala Gly Pro
    450                 455                 460

Pro Gly Ala Pro Gly Pro Ala Gly Pro Pro Gly Ala Pro Gly Pro Ala
465                 470                 475                 480

Gly Pro Pro Gly Ala Pro Gly Pro Ala Gly Pro Pro Gly Ala Pro Gly
                485                 490                 495

Pro Ala Gly Pro Pro Gly Ala Pro Gly Pro Ala Gly Pro Pro Gly Ala
            500                 505                 510

Pro Gly Pro Ala Gly Pro Pro Gly Ala His Gly Pro Ala Gly Pro Lys
        515                 520                 525

Gly Ala His Gly Pro Ala Gly Pro Lys Gly Ala Met Asp Pro Gly Arg
    530                 535                 540

Tyr Gln Leu Ser Ala Gly Arg Tyr His Tyr Gln Leu Val Trp Cys Gln
545                 550                 555                 560

Lys ( 2 ) INFORMATION FOR SEQ ID NO:53:

( i ) SEQUENCE CHARACTERISTICS:
        ( A ) LENGTH: 777 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:53:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala His Gly Pro Ala Gly Pro Lys Gly Ala His Gly Pro Ala
        35                  40                  45

Gly Pro Lys Gly Ala Pro Gly Pro Ala Gly Pro Pro Gly Ala Pro Gly
    50                  55                  60

Pro Ala Gly Pro Pro Gly Ala Pro Gly Pro Ala Gly Pro Pro Gly Ala
65                  70                  75                  80

Pro Gly Pro Ala Gly Pro Pro Gly Ala Pro Gly Pro Ala Gly Pro Pro
                85                  90                  95

Gly Ala Pro Gly Pro Ala Gly Pro Pro Gly Ala Pro Gly Pro Ala Gly
                100                 105                 110

Pro Pro Gly Ala Pro Gly Pro Ala Gly Pro Pro Gly Ala Pro Gly Pro
        115                 120                 125

Ala Gly Pro Pro Gly Ala Pro Gly Pro Ala Gly Pro Pro Gly Ala Pro
        130                 135                 140

Gly Pro Ala Gly Pro Pro Gly Ala Pro Gly Pro Ala Gly Pro Pro Gly
145                 150                 155                 160

Ala His Gly Pro Ala Gly Pro Lys Gly Ala His Gly Pro Ala Gly Pro

```
                        165                             170                             175
Lys  Gly  Ala  His  Gly  Pro  Ala  Gly  Pro  Lys  Gly  Ala  His  Gly  Pro  Ala
                        180                             185                             190
Gly  Pro  Lys  Gly  Ala  Pro  Gly  Pro  Ala  Gly  Pro  Pro  Gly  Ala  Pro  Gly
                        195                             200                             205
Pro  Ala  Gly  Pro  Pro  Gly  Ala  Pro  Gly  Pro  Ala  Gly  Pro  Pro  Gly  Ala
                        210                             215                             220
Pro  Gly  Pro  Ala  Gly  Pro  Pro  Gly  Ala  Pro  Gly  Pro  Ala  Gly  Pro  Pro
225                             230                             235                             240
Gly  Ala  Pro  Gly  Pro  Ala  Gly  Pro  Pro  Gly  Ala  Pro  Gly  Pro  Ala  Gly
                        245                             250                             255
Pro  Pro  Gly  Ala  Pro  Gly  Pro  Ala  Gly  Pro  Pro  Gly  Ala  Pro  Gly  Pro
                        260                             265                             270
Ala  Gly  Pro  Pro  Gly  Ala  Pro  Gly  Pro  Ala  Gly  Pro  Pro  Gly  Ala  Pro
                        275                             280                             285
Gly  Pro  Ala  Gly  Pro  Pro  Gly  Ala  Pro  Gly  Pro  Ala  Gly  Pro  Pro  Gly
                        290                             295                             300
Ala  His  Gly  Pro  Ala  Gly  Pro  Lys  Gly  Ala  His  Gly  Pro  Ala  Gly  Pro
305                             310                             315                             320
Lys  Gly  Ala  His  Gly  Pro  Ala  Gly  Pro  Lys  Gly  Ala  His  Gly  Pro  Ala
                        325                             330                             335
Gly  Pro  Lys  Gly  Ala  Pro  Gly  Pro  Ala  Gly  Pro  Pro  Gly  Ala  Pro  Gly
                        340                             345                             350
Pro  Ala  Gly  Pro  Pro  Gly  Ala  Pro  Gly  Pro  Ala  Gly  Pro  Pro  Gly  Ala
                        355                             360                             365
Pro  Gly  Pro  Ala  Gly  Pro  Pro  Gly  Ala  Pro  Gly  Pro  Ala  Gly  Pro  Pro
                        370                             375                             380
Gly  Ala  Pro  Gly  Pro  Ala  Gly  Pro  Pro  Gly  Ala  Pro  Gly  Pro  Ala  Gly
385                             390                             395                             400
Pro  Pro  Gly  Ala  Pro  Gly  Pro  Ala  Gly  Pro  Pro  Gly  Ala  Pro  Gly  Pro
                        405                             410                             415
Ala  Gly  Pro  Pro  Gly  Ala  Pro  Gly  Pro  Ala  Gly  Pro  Pro  Gly  Ala  Pro
                        420                             425                             430
Gly  Pro  Ala  Gly  Pro  Pro  Gly  Ala  Pro  Gly  Pro  Ala  Gly  Pro  Pro  Gly
                        435                             440                             445
Ala  His  Gly  Pro  Ala  Gly  Pro  Lys  Gly  Ala  His  Gly  Pro  Ala  Gly  Pro
                        450                             455                             460
Lys  Gly  Ala  His  Gly  Pro  Ala  Gly  Pro  Lys  Gly  Ala  His  Gly  Pro  Ala
465                             470                             475                             480
Gly  Pro  Lys  Gly  Ala  Pro  Gly  Pro  Ala  Gly  Pro  Pro  Gly  Ala  Pro  Gly
                        485                             490                             495
Pro  Ala  Gly  Pro  Pro  Gly  Ala  Pro  Gly  Pro  Ala  Gly  Pro  Pro  Gly  Ala
                        500                             505                             510
Pro  Gly  Pro  Ala  Gly  Pro  Pro  Gly  Ala  Pro  Gly  Pro  Ala  Gly  Pro  Pro
                        515                             520                             525
Gly  Ala  Pro  Gly  Pro  Ala  Gly  Pro  Pro  Gly  Ala  Pro  Gly  Pro  Ala  Gly
                        530                             535                             540
Pro  Pro  Gly  Ala  Pro  Gly  Pro  Ala  Gly  Pro  Pro  Gly  Ala  Pro  Gly  Pro
545                             550                             555                             560
Ala  Gly  Pro  Pro  Gly  Ala  Pro  Gly  Pro  Ala  Gly  Pro  Pro  Gly  Ala  Pro
                        565                             570                             575
Gly  Pro  Ala  Gly  Pro  Pro  Gly  Ala  Pro  Gly  Pro  Ala  Gly  Pro  Pro  Gly
                        580                             585                             590
```

| | | | | | | | | | | | | | |
|---|---|---|---|---|---|---|---|---|---|---|---|---|---|
| Ala | His | Gly<br>595 | Pro | Ala | Gly | Pro | Lys<br>600 | Gly | Ala | His | Gly<br>605 | Pro | Ala | Gly | Pro |
| Lys | Gly<br>610 | Ala | His | Gly | Pro<br>615 | Ala | Gly | Pro | Lys | Gly<br>620 | Ala | His | Gly | Pro | Ala |
| Gly<br>625 | Pro | Lys | Gly | Ala | Pro<br>630 | Gly | Pro | Ala | Gly | Pro<br>635 | Pro | Gly | Ala | Pro | Gly<br>640 |
| Pro | Ala | Gly | Pro | Pro<br>645 | Gly | Ala | Pro | Gly | Pro<br>650 | Ala | Gly | Pro | Pro<br>655 | Gly | Ala |
| Pro | Gly | Pro | Ala<br>660 | Gly | Pro | Pro | Gly<br>665 | Ala | Pro | Gly | Pro<br>670 | Ala | Gly | Pro | Pro |
| Gly | Ala | Pro<br>675 | Gly | Pro | Ala | Gly | Pro<br>680 | Pro | Gly | Ala | Pro<br>685 | Gly | Pro | Ala | Gly |
| Pro | Pro<br>690 | Gly | Ala | Pro | Gly | Pro<br>695 | Ala | Gly | Pro | Pro | Gly<br>700 | Ala | Pro | Gly | Pro |
| Ala<br>705 | Gly | Pro | Pro | Gly | Ala<br>710 | Pro | Gly | Pro | Ala | Gly<br>715 | Pro | Pro | Gly | Ala | Pro<br>720 |
| Gly | Pro | Ala | Gly | Pro<br>725 | Pro | Gly | Ala | Pro | Gly<br>730 | Pro | Ala | Gly | Pro | Pro<br>735 | Gly |
| Ala | His | Gly | Pro<br>740 | Ala | Gly | Pro | Lys<br>745 | Gly | Ala | His | Gly | Pro<br>750 | Ala | Gly | Pro |
| Lys | Gly | Ala<br>755 | Met | Asp | Pro | Gly | Arg<br>760 | Tyr | Gln | Leu | Ser | Ala<br>765 | Gly | Arg | Tyr |
| His | Tyr | Gln<br>770 | Leu | Val | Trp | Cys<br>775 | Gln | Lys | | | | | | | |

( 2 ) INFORMATION FOR SEQ ID NO:54:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:54:

GTGCTCCGGG ACCTGCAGAA TATTATTCTA GAGGTGACCC AGGACGCCT G       51

( 2 ) INFORMATION FOR SEQ ID NO:55:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:55:

GCACCACGCG GTCCTGGGTC ACCTCTAGAA TAATATTCTG CAGGTCCCGG A       51

( 2 ) INFORMATION FOR SEQ ID NO:56:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:56:

GGCCCACCGG GTAGCCGTGG CGATCCGGGA CCACCGGGTG CACCTGGCCC AGCGGGTCCG 60

CCTGGAT 67

( 2 ) INFORMATION FOR SEQ ID NO:57:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic"

( x i ) SEQUENCE DESCRIPTION: SEQ ID NO:57:

CTAGATCCAG GCGGACCCGC TGGGCCAGGT GCACCCGGTG GTCCCGGATC GCCACGGCTA 60

CCCGGTGGGC CTGCA 75

( 2 ) INFORMATION FOR SEQ ID NO:58:

( i ) SEQUENCE CHARACTERISTICS:
    ( A ) LENGTH: 108 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "synthetic"

( x i ) SEQUENCE DESCRIPTION: SEQ ID NO:58:

GGTGCTCCGG GACCTGCAGG CCCACCGGGT AGCCGTGGCG ATCCGGGACC ACCGGGTGCA 60

CCTGGCCCAG CGGGTCCGCC TGGATCTAGA GGTGACCCAG GACCGCCT 108

( 2 ) INFORMATION FOR SEQ ID NO:59:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:59:

Gly Ala Pro Gly Pro Ala Gly Pro Pro Gly Ser Arg Gly Asp Pro Gly
 1               5                  10                  15

Pro Pro Gly Ala Pro Gly Pro Ala Gly Pro Pro Gly Ser Arg Gly Asp
             20                  25                  30

Pro Gly Pro Pro
         35

( 2 ) INFORMATION FOR SEQ ID NO:60:

( i ) SEQUENCE CHARACTERISTICS:
    ( A ) LENGTH: 810 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "synthetic"

( x i ) SEQUENCE DESCRIPTION: SEQ ID NO:60:

GGTGCTCACG GCCCAGCAGG TCCGAAGGGC GCGCATGGCC CAGCAGGCCC GAAAGGTGCT 60

| | | | | | |
|---|---|---|---|---|---|
| CCGGGACCTG | CAGGCCCACC | GGGTAGCCGT | GGCGATCCGG | GACCACCGGG | TGCACCTGGC | 120
| CCAGCGGGTC | CGCCTGGATC | TAGAGGTGAC | CCAGGACCGC | CTGGTGCTCC | GGGACCTGCA | 180
| GGCCCACCGG | GTAGCCGTGG | CGATCCGGGA | CCACCGGGTG | CACCTGGCCC | AGCGGGTCCG | 240
| CCTGGATCTA | GAGGTGACCC | AGGACCGCCT | GGTGCTCCGG | GACCTGCAGG | CCCACCGGGT | 300
| AGCCGTGGCG | ATCCGGGACC | ACCGGGTGCA | CCTGGCCCAG | CGGGTCCGCC | TGGATCTAGA | 360
| GGTGACCCAG | GACCGCCTGG | TGCTCCGGGA | CCTGCAGGCC | CACCGGGTAG | CCGTGGCGAT | 420
| CCGGGACCAC | CGGGTGCACC | TGGCCCAGCG | GGTCCGCCTG | GATCTAGAGG | TGACCCAGGA | 480
| CCGCCTGGTG | CTCCGGGACC | TGCAGGCCCA | CCGGGTAGCC | GTGGCGATCC | GGGACCACCG | 540
| GGTGCACCTG | GCCCAGCGGG | TCCGCCTGGA | TCTAGAGGTG | ACCCAGGACC | GCCTGGTGCT | 600
| CCGGGACCTG | CAGGCCCACC | GGGTAGCCGT | GGCGATCCGG | GACCACCGGG | TGCACCTGGC | 660
| CCAGCGGGTC | CGCCTGGATC | TAGAGGTGAC | CCAGGACCGC | CTGGTGCCCA | TGGCCCAGCA | 720
| GGACCGAAAG | GAGCTCACGG | TCCGGCAGGT | CCGAAACCAC | GGGTACCGGG | TCGTCCTGGC | 780
| TTTCCTCGAG | TGCCAGGCCG | TCCAGGCTTT | | | | 810

(2) INFORMATION FOR SEQ ID NO:61:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Gly Ala His Gly Pro Ala Gly Pro Lys Gly Ala His Gly Pro Ala Gly
  1               5                  10                  15
Pro Lys Gly Ala Pro Gly Pro Ala Gly Pro Pro Gly Ser Arg Gly Asp
             20                  25                  30
Pro Gly Pro Pro Gly Ala Pro Gly Pro Ala Gly Pro Pro Gly Ser Arg
         35                  40                  45
Gly Asp Pro Gly Pro Pro Gly Ala Pro Gly Pro Ala Gly Pro Pro Gly
     50                  55                  60
Ser Arg Gly Asp Pro Gly Pro Pro Gly Ala Pro Gly Pro Ala Gly Pro
 65                  70                  75                  80
Pro Gly Ser Arg Gly Asp Pro Gly Pro Pro Gly Ala Pro Gly Pro Ala
                 85                  90                  95
Gly Pro Pro Gly Ser Arg Gly Asp Pro Gly Pro Pro Gly Ala Pro Gly
                100                 105                 110
Pro Ala Gly Pro Pro Gly Ser Arg Gly Asp Pro Gly Pro Pro Gly Ala
            115                 120                 125
Pro Gly Pro Ala Gly Pro Pro Gly Ser Arg Gly Asp Pro Gly Pro Pro
        130                 135                 140
Gly Ala Pro Gly Pro Ala Gly Pro Pro Gly Ser Arg Gly Asp Pro Gly
145                 150                 155                 160
Pro Pro Gly Ala Pro Gly Pro Ala Gly Pro Pro Gly Ser Arg Gly Asp
                165                 170                 175
Pro Gly Pro Pro Gly Ala Pro Gly Pro Ala Gly Pro Pro Gly Ser Arg
            180                 185                 190
Gly Asp Pro Gly Pro Pro Gly Ala Pro Gly Pro Ala Gly Pro Pro Gly
        195                 200                 205
Ser Arg Gly Asp Pro Gly Pro Pro Gly Ala Pro Gly Pro Ala Gly Pro
    210                 215                 220
```

Pro Gly Ser Arg Gly Asp Pro Gly Pro Pro Gly Ala His Gly Pro Ala
225                 230             235                 240

Gly Pro Lys Gly Ala His Gly Pro Ala Gly Pro Lys
            245             250

( 2 ) INFORMATION FOR SEQ ID NO:62:

( i ) SEQUENCE CHARACTERISTICS:
        ( A ) LENGTH: 1064 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:62:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala His Gly Pro Ala Gly Pro Lys Gly Ala His Gly Pro Ala
        35                  40                  45

Gly Pro Lys Gly Ala Pro Gly Pro Ala Gly Pro Pro Gly Ser Arg Gly
    50                  55                  60

Asp Pro Gly Pro Pro Gly Ala Pro Gly Pro Ala Gly Pro Pro Gly Ser
65                  70                  75                  80

Arg Gly Asp Pro Gly Pro Pro Gly Ala Pro Gly Pro Ala Gly Pro Pro
            85                  90                  95

Gly Ser Arg Gly Asp Pro Gly Pro Pro Gly Ala Pro Gly Pro Ala Gly
            100                 105                 110

Pro Pro Gly Ser Arg Gly Asp Pro Gly Pro Pro Gly Ala Pro Gly Pro
        115                 120                 125

Ala Gly Pro Pro Gly Ser Arg Gly Asp Pro Gly Pro Pro Gly Ala Pro
    130                 135                 140

Gly Pro Ala Gly Pro Pro Gly Ser Arg Gly Asp Pro Gly Pro Pro Gly
145                 150                 155                 160

Ala Pro Gly Pro Ala Gly Pro Pro Gly Ser Arg Gly Asp Pro Gly Pro
            165                 170                 175

Pro Gly Ala Pro Gly Pro Ala Gly Pro Gly Ser Arg Gly Asp Pro
        180                 185                 190

Gly Pro Pro Gly Ala Pro Gly Pro Ala Gly Pro Pro Gly Ser Arg Gly
        195                 200                 205

Asp Pro Gly Pro Pro Gly Ala Pro Gly Pro Ala Gly Pro Pro Gly Ser
    210                 215                 220

Arg Gly Asp Pro Gly Pro Pro Gly Ala Pro Gly Pro Ala Gly Pro Pro
225                 230                 235                 240

Gly Ser Arg Gly Asp Pro Gly Pro Pro Gly Ala Pro Gly Pro Ala Gly
            245                 250                 255

Pro Pro Gly Ser Arg Gly Asp Pro Gly Pro Pro Gly Ala His Gly Pro
        260                 265                 270

Ala Gly Pro Lys Gly Ala His Gly Pro Ala Gly Pro Lys Gly Ala His
        275                 280                 285

Gly Pro Ala Gly Pro Lys Gly Ala His Gly Pro Ala Gly Pro Lys Gly
        290                 295                 300

Ala Pro Gly Pro Ala Gly Pro Pro Gly Ser Arg Gly Asp Pro Gly Pro
305                 310                 315                 320

-continued

| | | | | | | | | | | | | | | |
|---|---|---|---|---|---|---|---|---|---|---|---|---|---|---|
|Pro|Gly|Ala|Pro|Gly 325|Pro|Ala|Gly|Pro|Pro 330|Gly|Ser|Arg|Gly|Asp Pro 335|
|Gly|Pro|Pro|Gly 340|Ala|Pro|Gly|Pro|Ala 345|Gly|Pro|Pro|Gly|Ser|Arg Gly 350|
|Asp|Pro 355|Gly|Pro|Pro|Gly|Ala|Pro 360|Gly|Pro|Ala|Gly|Pro 365|Pro|Gly Ser|
|Arg 370|Gly|Asp|Pro|Gly|Pro 375|Pro|Gly|Ala|Pro|Gly 380|Pro|Ala|Gly|Pro Pro|
|Gly 385|Ser|Arg|Gly|Asp|Pro 390|Gly|Pro|Pro|Gly|Ala 395|Pro|Gly|Pro|Ala Gly 400|
|Pro|Pro|Gly|Ser|Arg 405|Gly|Asp|Pro|Gly|Pro 410|Pro|Gly|Ala|Pro|Gly Pro 415|
|Ala|Gly|Pro|Pro 420|Gly|Ser|Arg|Gly|Asp 425|Pro|Gly|Pro|Pro|Gly 430|Ala Pro|
|Gly|Pro|Ala 435|Gly|Pro|Pro|Gly|Ser 440|Arg|Gly|Asp|Pro|Gly 445|Pro|Pro Gly|
|Ala|Pro 450|Gly|Pro|Ala|Gly|Pro 455|Pro|Gly|Ser|Arg|Gly 460|Asp|Pro|Gly Pro|
|Pro 465|Gly|Ala|Pro|Gly|Pro 470|Ala|Gly|Pro|Pro|Gly 475|Ser|Arg|Gly|Asp Pro 480|
|Gly|Pro|Pro|Gly|Ala 485|Pro|Gly|Pro|Ala|Gly 490|Pro|Pro|Gly|Ser|Arg Gly 495|
|Asp|Pro|Gly|Pro 500|Pro|Gly|Ala|Pro|Gly 505|Pro|Ala|Gly|Pro 510|Pro|Gly Ser|
|Arg|Gly|Asp 515|Pro|Gly|Pro|Pro|Gly 520|Ala|His|Gly|Pro|Ala 525|Gly|Pro Lys|
|Gly|Ala|His 530|Gly|Pro|Ala|Gly 535|Pro|Lys|Gly|Ala|His 540|Gly|Pro|Ala Gly|
|Pro 545|Lys|Gly|Ala|His|Gly 550|Pro|Ala|Gly|Pro|Lys 555|Gly|Ala|Pro|Gly Pro 560|
|Ala|Gly|Pro|Pro|Gly 565|Ser|Arg|Gly|Asp|Pro 570|Gly|Pro|Pro|Gly|Ala Pro 575|
|Gly|Pro|Ala|Gly 580|Pro|Pro|Gly|Ser|Arg 585|Gly|Asp|Pro|Gly|Pro 590|Pro Gly|
|Ala|Pro|Gly 595|Pro|Ala|Gly|Pro|Pro 600|Gly|Ser|Arg|Gly|Asp 605|Pro|Gly Pro|
|Pro|Gly|Ala 610|Pro|Gly|Pro|Ala 615|Gly|Pro|Pro|Gly|Ser 620|Arg|Gly|Asp Pro|
|Gly 625|Pro|Pro|Gly|Ala 630|Pro|Gly|Pro|Ala|Gly 635|Pro|Pro|Gly|Ser|Arg Gly 640|
|Asp|Pro|Gly|Pro|Pro 645|Gly|Ala|Pro|Gly|Pro 650|Ala|Gly|Pro|Pro|Gly Ser 655|
|Arg|Gly|Asp|Pro 660|Gly|Pro|Pro|Gly|Ala 665|Pro|Gly|Pro|Ala|Gly 670|Pro Pro|
|Gly|Ser|Arg 675|Gly|Asp|Pro|Gly|Pro 680|Pro|Gly|Ala|Pro|Gly 685|Pro|Ala Gly|
|Pro|Pro|Gly|Ser|Arg 690|Gly|Asp|Pro|Gly|Pro 695|Pro|Gly|Ala|Pro 700|Gly Pro|
|Ala|Gly|Pro|Pro 705|Gly|Ser|Arg|Gly|Asp 710|Pro|Gly|Pro|Pro|Gly 715|Ala Pro 720|
|Gly|Pro|Ala|Gly 725|Pro|Pro|Gly|Ser|Arg 730|Gly|Asp|Pro|Gly|Pro 735|Pro Gly|
|Ala|Pro|Gly|Pro 740|Ala|Gly|Pro|Pro|Gly 745|Ser|Arg|Gly|Asp|Pro 750|Gly Pro|

```
Pro Gly Ala Pro Gly Pro Ala Gly Pro Pro Gly Ser Arg Gly Asp Pro
        755             760             765
Gly Pro Pro Gly Ala His Gly Pro Ala Gly Pro Lys Gly Ala His Gly
    770             775             780
Pro Ala Gly Pro Lys Gly Ala His Gly Pro Ala Gly Pro Lys Gly Ala
785             790             795             800
His Gly Pro Ala Gly Pro Lys Gly Ala Pro Gly Pro Ala Gly Pro Pro
            805             810             815
Gly Ser Arg Gly Asp Pro Gly Pro Pro Gly Ala Pro Gly Pro Ala Gly
        820             825             830
Pro Pro Gly Ser Arg Gly Asp Pro Gly Pro Pro Gly Ala Pro Gly Pro
        835             840             845
Ala Gly Pro Pro Gly Ser Arg Gly Asp Pro Gly Pro Pro Gly Ala Pro
    850             855             860
Gly Pro Ala Gly Pro Pro Gly Ser Arg Gly Asp Pro Gly Pro Pro Gly
865             870             875             880
Ala Pro Gly Pro Ala Gly Pro Pro Gly Ser Arg Gly Asp Pro Gly Pro
            885             890             895
Pro Gly Ala Pro Gly Pro Ala Gly Pro Pro Gly Ser Arg Gly Asp Pro
        900             905             910
Gly Pro Pro Gly Ala Pro Gly Pro Ala Gly Pro Pro Gly Ser Arg Gly
        915             920             925
Asp Pro Gly Pro Pro Gly Ala Pro Gly Pro Ala Gly Pro Pro Gly Ser
    930             935             940
Arg Gly Asp Pro Gly Pro Pro Gly Ala Pro Gly Pro Ala Gly Pro Pro
945             950             955             960
Gly Ser Arg Gly Asp Pro Gly Pro Pro Gly Ala Pro Gly Pro Ala Gly
            965             970             975
Pro Pro Gly Ser Arg Gly Asp Pro Gly Pro Pro Gly Ala Pro Gly Pro
        980             985             990
Ala Gly Pro Pro Gly Ser Arg Gly Asp Pro Gly Pro Pro Gly Ala Pro
        995             1000            1005
Gly Pro Ala Gly Pro Pro Gly Ser Arg Gly Asp Pro Gly Pro Pro Gly
    1010            1015            1020
Ala His Gly Pro Ala Gly Pro Lys Gly Ala His Gly Pro Ala Gly Pro
1025            1030            1035            1040
Lys Gly Ala Met Asp Pro Gly Arg Tyr Gln Leu Ser Ala Gly Arg Tyr
            1045            1050            1055
His Gln Leu Val Trp Cys Gln Lys
            1060
```

( 2 ) INFORMATION FOR SEQ ID NO:63:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

```
Gly Ala Gln Gly Pro Ala Gly Pro Gly
1               5
```

( 2 ) INFORMATION FOR SEQ ID NO:64:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic"

( x i ) SEQUENCE DESCRIPTION: SEQ ID NO:64:

GTGCACAGGG ACCGGCGGGA CCAGGTGGCT CTCGAGGCGA TCCGGGTCCT CCGG 54

( 2 ) INFORMATION FOR SEQ ID NO:65:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic"

( x i ) SEQUENCE DESCRIPTION: SEQ ID NO:65:

GCACCCGGAG GACCCGGATC GCCTCGAGAG CCACCTGGTC CCGCCGGTCC CTGT 54

( 2 ) INFORMATION FOR SEQ ID NO:66:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic"

( x i ) SEQUENCE DESCRIPTION: SEQ ID NO:66:

GTGCACAAGG ACCGGCAGGC CCTGGTGGCA GCCGCGGTGA TCCGGGCCCA CCGG 54

( 2 ) INFORMATION FOR SEQ ID NO:67:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic"

( x i ) SEQUENCE DESCRIPTION: SEQ ID NO:67:

GCACCCGGTG GGCCCGGATC ACCGCGGCTG CCACCAGGGC CTGCCGGTCC TTGT 54

( 2 ) INFORMATION FOR SEQ ID NO:68:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic"

( x i ) SEQUENCE DESCRIPTION: SEQ ID NO:68:

GTGCTCAAGG ACCGGCTGGC CCAGGCGGTT CCCGTGGAGA CCCGGGTCCA CCGG 54

( 2 ) INFORMATION FOR SEQ ID NO:69:

(  i  ) SEQUENCE CHARACTERISTICS:
            ( A ) LENGTH: 53 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic"

( x i ) SEQUENCE DESCRIPTION: SEQ ID NO:69:

GCACCCGGTG GACCCGGGTC TCCACGGGAA CCGCCTGGCC AGCCGGTCCT TGA    53

( 2 ) INFORMATION FOR SEQ ID NO:70:

(  i  ) SEQUENCE CHARACTERISTICS:
            ( A ) LENGTH: 162 base pairs
            ( B ) TYPE: nucleic acid
            ( C ) STRANDEDNESS: double
            ( D ) TOPOLOGY: linear ( i i ) MOLECULE TYPE: other nucleic acid
            ( A ) DESCRIPTION: /desc = "synthetic"

( x i ) SEQUENCE DESCRIPTION: SEQ ID NO:70:

GGTGCACAGG GACCGGCGGG ACCAGGTGGC TCTCGAGGCG ATCCGGGTCC TCCGGGTGCA    60

CAAGGACCGG CAGGCCCTGG TGGCAGCCGC GGTGATCCGG GCCCACCGGG TGCTCAAGGA    120

CCGGCTGGCC CAGGCGGTTC CCGTGGAGAC CCGGGTCCAC CG    162

( 2 ) INFORMATION FOR SEQ ID NO:71:

(  i  ) SEQUENCE CHARACTERISTICS:
            ( A ) LENGTH: 54 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:71:

Gly Ala Gln Gly Pro Ala Gly Pro Gly Gly Ser Arg Gly Asp Pro Gly
    1               5                   10                  15

Pro Pro Gly Ala Gln Gly Pro Ala Gly Pro Gly Gly Ser Arg Gly Asp
                    20                  25                  30

Pro Gly Pro Pro Gly Ala Gln Gly Pro Ala Gly Pro Gly Gly Ser Arg
                35                  40                  45

Gly Asp Pro Gly Pro Pro
                50

( 2 ) INFORMATION FOR SEQ ID NO:72:

(  i  ) SEQUENCE CHARACTERISTICS:
            ( A ) LENGTH: 1065 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:72:

Met Asp Pro Val Val Leu Gln Arg Arg Asp Trp Glu Asn Pro Gly Val
    1               5                   10                  15

Thr Gln Leu Asn Arg Leu Ala Ala His Pro Pro Phe Ala Ser Asp Pro
                    20                  25                  30

Met Gly Ala His Gly Pro Ala Gly Pro Lys Gly Ala His Gly Pro Ala
                35                  40                  45

```
Gly Pro Lys Gly Ala Gln Gly Pro Ala Gly Pro Gly Gly Ser Arg Gly
     50              55              60

Asp Pro Gly Pro Pro Gly Ala Gln Gly Pro Ala Gly Pro Gly Gly Ser
65              70              75                          80

Arg Gly Asp Pro Gly Pro Pro Gly Ala Gln Gly Pro Ala Gly Pro Gly
             85                  90              95

Gly Ser Arg Gly Asp Pro Gly Pro Pro Gly Ala Gln Gly Pro Ala Gly
            100             105             110

Pro Gly Gly Ser Arg Gly Asp Pro Gly Pro Pro Gly Ala Gln Gly Pro
            115             120             125

Ala Gly Pro Gly Gly Ser Arg Gly Asp Pro Gly Pro Pro Gly Ala Gln
    130             135             140

Gly Pro Ala Gly Pro Gly Gly Ser Arg Gly Asp Pro Gly Pro Pro Gly
145             150             155                         160

Ala Gln Gly Pro Ala Gly Pro Gly Gly Ser Arg Gly Asp Pro Gly Pro
                165             170             175

Pro Gly Ala Gln Gly Pro Ala Gly Pro Gly Gly Ser Arg Gly Asp Pro
            180             185             190

Gly Pro Pro Gly Ala Gln Gly Pro Ala Gly Pro Gly Gly Ser Arg Gly
        195             200             205

Asp Pro Gly Pro Pro Gly Ala Gln Gly Pro Ala Gly Pro Gly Gly Ser
210             215             220

Arg Gly Asp Pro Gly Pro Pro Gly Ala Gln Gly Pro Ala Gly Pro Gly
225             230             235                         240

Gly Ser Arg Gly Asp Pro Gly Pro Pro Gly Ala Gln Gly Pro Ala Gly
            245             250             255

Pro Gly Gly Ser Arg Gly Asp Pro Gly Pro Pro Gly Ala His Gly Pro
            260             265             270

Ala Gly Pro Lys Gly Ala His Gly Pro Ala Gly Pro Lys Gly Ala His
        275             280             285

Gly Pro Ala Gly Pro Lys Gly Ala His Gly Pro Ala Gly Pro Lys Gly
    290             295             300

Ala Gln Gly Pro Ala Gly Pro Gly Gly Ser Arg Gly Asp Pro Gly Pro
305             310             315                         320

Pro Gly Ala Gln Gly Pro Ala Gly Pro Gly Gly Ser Arg Gly Asp Pro
            325             330             335

Gly Pro Pro Gly Ala Gln Gly Pro Ala Gly Pro Gly Gly Ser Arg Gly
        340             345             350

Asp Pro Gly Pro Pro Gly Ala Gln Gly Pro Ala Gly Pro Gly Gly Ser
        355             360             365

Arg Gly Asp Pro Gly Pro Pro Gly Ala Gln Gly Pro Ala Gly Pro Gly
    370             375             380

Gly Ser Arg Gly Asp Pro Gly Pro Pro Gly Ala Gln Gly Pro Ala Gly
385             390             395                         400

Pro Gly Gly Ser Arg Gly Asp Pro Gly Pro Pro Gly Ala Gln Gly Pro
            405             410             415

Ala Gly Pro Gly Gly Ser Arg Gly Asp Pro Gly Pro Pro Gly Ala Gln
        420             425             430

Gly Pro Ala Gly Pro Gly Gly Ser Arg Gly Asp Pro Gly Pro Pro Gly
    435             440             445

Ala Gln Gly Pro Ala Gly Pro Gly Gly Ser Arg Gly Asp Pro Gly Pro
450             455             460

Pro Gly Ala Gln Gly Pro Ala Gly Pro Gly Gly Ser Arg Gly Asp Pro
465             470             475             480
```

Gly Pro Pro Gly Ala Gln Gly Pro Ala Gly Pro Gly Gly Ser Arg Gly
                485                 490                 495
Asp Pro Gly Pro Pro Gly Ala Gln Gly Pro Ala Gly Pro Gly Gly Ser
            500                 505                 510
Arg Gly Asp Pro Gly Pro Pro Gly Ala His Gly Pro Ala Gly Pro Lys
        515                 520                 525
Gly Ala His Gly Pro Ala Gly Pro Lys Gly Ala His Gly Pro Ala Gly
    530                 535                 540
Pro Lys Gly Ala His Gly Pro Ala Gly Pro Lys Gly Ala Gln Gly Pro
545                 550                 555                 560
Ala Gly Pro Gly Gly Ser Arg Gly Asp Pro Gly Pro Pro Gly Ala Gln
                565                 570                 575
Gly Pro Ala Gly Pro Gly Gly Ser Arg Gly Asp Pro Gly Pro Pro Gly
            580                 585                 590
Ala Gln Gly Pro Ala Gly Pro Gly Gly Ser Arg Gly Asp Pro Gly Pro
        595                 600                 605
Pro Gly Ala Gln Gly Pro Ala Gly Pro Gly Gly Ser Arg Gly Asp Pro
    610                 615                 620
Gly Pro Pro Gly Ala Gln Gly Pro Ala Gly Pro Gly Gly Ser Arg Gly
625                 630                 635                 640
Asp Pro Gly Pro Pro Gly Ala Gln Gly Pro Ala Gly Pro Gly Gly Ser
                645                 650                 655
Arg Gly Asp Pro Gly Pro Pro Gly Ala Gln Gly Pro Ala Gly Pro Gly
            660                 665                 670
Gly Ser Arg Gly Asp Pro Gly Pro Pro Gly Ala Gln Gly Pro Ala Gly
        675                 680                 685
Pro Gly Gly Ser Arg Gly Asp Pro Gly Pro Pro Gly Ala Gln Gly Pro
    690                 695                 700
Ala Gly Pro Gly Gly Ser Arg Gly Asp Pro Gly Pro Pro Gly Ala Gln
705                 710                 715                 720
Gly Pro Ala Gly Pro Gly Gly Ser Arg Gly Asp Pro Gly Pro Pro Gly
                725                 730                 735
Ala Gln Gly Pro Ala Gly Pro Gly Gly Ser Arg Gly Asp Pro Gly Pro
            740                 745                 750
Pro Gly Ala Gln Gly Pro Ala Gly Pro Gly Gly Ser Arg Gly Asp Pro
        755                 760                 765
Gly Pro Pro Gly Ala His Gly Pro Ala Gly Pro Lys Gly Ala His Gly
    770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
                805                 810                 815
Gly Ser Arg Gly Asp Pro Gly Pro Pro Gly Ala Gln Gly Pro Ala Gly
            820                 825                 830
Pro Gly Gly Ser Arg Gly Asp Pro Gly Pro Pro Gly Ala Gln Gly Pro
        835                 840                 845
Ala Gly Pro Gly Gly Ser Arg Gly Asp Pro Gly Pro Pro Gly Ala Gln
    850                 855                 860
Gly Pro Ala Gly Pro Gly Gly Ser Arg Gly Asp Pro Gly Pro Pro Gly
865                 870                 875                 880
Ala Gln Gly Pro Ala Gly Pro Gly Gly Ser Arg Gly Asp Pro Gly Pro
                885                 890                 895
Pro Gly Ala Gln Gly Pro Ala Gly Pro Gly Gly Ser Arg Gly Asp Pro

```
                        900                         905                         910
Gly  Pro  Pro  Gly  Ala  Gln  Gly  Pro  Ala  Gly  Pro  Gly  Gly  Ser  Arg  Gly
               915                      920                      925

Asp  Pro  Gly  Pro  Pro  Gly  Ala  Gln  Gly  Pro  Ala  Gly  Pro  Gly  Gly  Ser
930                      935                      940

Arg  Gly  Asp  Pro  Gly  Pro  Pro  Gly  Ala  Gln  Gly  Pro  Ala  Gly  Pro  Gly
945                      950                      955                           960

Gly  Ser  Arg  Gly  Asp  Pro  Gly  Pro  Pro  Gly  Ala  Gln  Gly  Pro  Ala  Gly
                    965                           970                      975

Pro  Gly  Gly  Ser  Arg  Gly  Asp  Pro  Gly  Pro  Pro  Gly  Ala  Gln  Gly  Pro
               980                      985                           990

Ala  Gly  Pro  Gly  Gly  Ser  Arg  Gly  Asp  Pro  Gly  Pro  Pro  Gly  Ala  Gln
               995                      1000                     1005

Gly  Pro  Ala  Gly  Pro  Gly  Gly  Ser  Arg  Gly  Asp  Pro  Gly  Pro  Pro  Gly
               1010                     1015                     1020

Ala  His  Gly  Pro  Ala  Gly  Pro  Lys  Gly  Ala  His  Gly  Pro  Ala  Gly  Pro
1025                     1030                     1035                          1040

Lys  Gly  Ala  Met  Asp  Pro  Gly  Arg  Tyr  Gln  Leu  Ser  Ala  Gly  Arg  Tyr
               1045                     1050                     1055

His  Tyr  Gln  Leu  Val  Trp  Cys  Cys  Lys
                    1060                1065
```

( 2 ) INFORMATION FOR SEQ ID NO:73:

( i ) SEQUENCE CHARACTERISTICS:
        ( A ) LENGTH: 633 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:73:

```
Met  Asp  Pro  Val  Val  Leu  Gln  Arg  Arg  Asp  Trp  Glu  Asn  Pro  Gly  Val
1                   5                        10                       15

Thr  Gln  Leu  Asn  Arg  Leu  Ala  Ala  His  Pro  Pro  Phe  Ala  Ser  Asp  Pro
               20                       25                       30

Met  Gly  Ala  His  Gly  Pro  Ala  Gly  Pro  Lys  Gly  Ala  His  Gly  Pro  Ala
               35                       40                       45

Gly  Pro  Lys  Gly  Ala  Gln  Gly  Pro  Ala  Gly  Pro  Gly  Gly  Ser  Arg  Gly
     50                       55                       60

Asp  Pro  Gly  Pro  Pro  Gly  Ala  Gln  Gly  Pro  Ala  Gly  Pro  Gly  Gly  Ser
65                       70                       75                           80

Arg  Gly  Asp  Pro  Gly  Pro  Pro  Gly  Ala  Gln  Gly  Pro  Ala  Gly  Pro  Gly
               85                       90                       95

Gly  Ser  Arg  Gly  Asp  Pro  Gly  Pro  Pro  Gly  Ala  Gln  Gly  Pro  Ala  Gly
               100                      105                      110

Pro  Gly  Gly  Ser  Arg  Gly  Asp  Pro  Gly  Pro  Pro  Gly  Ala  Gln  Gly  Pro
          115                      120                      125

Ala  Gly  Pro  Gly  Gly  Ser  Arg  Gly  Asp  Pro  Gly  Pro  Pro  Gly  Ala  Gln
     130                      135                      140

Gly  Pro  Ala  Gly  Pro  Gly  Gly  Ser  Arg  Gly  Asp  Pro  Gly  Pro  Pro  Gly
145                      150                      155                          160

Ala  His  Gly  Pro  Ala  Gly  Pro  Lys  Gly  Ala  His  Gly  Pro  Ala  Gly  Pro
               165                      170                      175

Lys  Gly  Ala  His  Gly  Pro  Ala  Gly  Pro  Lys  Gly  Ala  His  Gly  Pro  Ala
               180                      185                      190
```

```
Gly Pro Lys Gly Ala Gln Gly Pro Ala Gly Pro Gly Gly Ser Arg Gly
        195                 200                 205
Asp Pro Gly Pro Pro Gly Ala Gln Gly Pro Ala Gly Pro Gly Gly Ser
        210                 215                 220
Arg Gly Asp Pro Gly Pro Pro Gly Ala Gln Gly Pro Ala Gly Pro Gly
225                 230                 235                 240
Gly Ser Arg Gly Asp Pro Gly Pro Pro Gly Ala Gln Gly Pro Ala Gly
                    245                 250                 255
Pro Gly Gly Ser Arg Gly Asp Pro Gly Pro Pro Gly Ala Gln Gly Pro
                260                 265                 270
Ala Gly Pro Gly Gly Ser Arg Gly Asp Pro Gly Pro Pro Gly Ala Gln
            275                 280                 285
Gly Pro Ala Gly Pro Gly Gly Ser Arg Gly Asp Pro Gly Pro Pro Gly
        290                 295                 300
Ala His Gly Pro Ala Gly Pro Lys Gly Ala His Gly Pro Ala Gly Pro
305                 310                 315                 320
Lys Gly Ala His Gly Pro Ala Gly Pro Lys Gly Ala His Gly Pro Ala
                    325                 330                 335
Gly Pro Lys Gly Ala Gln Gly Pro Ala Gly Pro Gly Gly Ser Arg Gly
                340                 345                 350
Asp Pro Gly Pro Pro Gly Ala Gln Gly Pro Ala Gly Pro Gly Gly Ser
            355                 360                 365
Arg Gly Asp Pro Gly Pro Pro Gly Ala Gln Gly Pro Ala Gly Pro Gly
370                 375                 380
Gly Ser Arg Gly Asp Pro Gly Pro Pro Gly Ala Gln Gly Pro Ala Gly
385                 390                 395                 400
Pro Gly Gly Ser Arg Gly Asp Pro Gly Pro Pro Gly Ala Gln Gly Pro
                    405                 410                 415
Ala Gly Pro Gly Gly Ser Arg Gly Asp Pro Gly Pro Pro Gly Ala Gln
                420                 425                 430
Gly Pro Ala Gly Pro Gly Gly Ser Arg Gly Asp Pro Gly Pro Pro Gly
            435                 440                 445
Ala His Gly Pro Ala Gly Pro Lys Gly Ala His Gly Pro Ala Gly Pro
    450                 455                 460
Lys Gly Ala His Gly Pro Ala Gly Pro Lys Gly Ala His Gly Pro Ala
465                 470                 475                 480
Gly Pro Lys Gly Ala Gln Gly Pro Ala Gly Pro Gly Gly Ser Arg Gly
                    485                 490                 495
Asp Pro Gly Pro Pro Gly Ala Gln Gly Pro Ala Gly Pro Gly Gly Ser
                500                 505                 510
Arg Gly Asp Pro Gly Pro Pro Gly Ala Gln Gly Pro Ala Gly Pro Gly
            515                 520                 525
Gly Ser Arg Gly Asp Pro Gly Pro Pro Gly Ala Gln Gly Pro Ala Gly
        530                 535                 540
Pro Gly Gly Ser Arg Gly Asp Pro Gly Pro Pro Gly Ala Gln Gly Pro
545                 550                 555                 560
Ala Gly Pro Gly Gly Ser Arg Gly Asp Pro Gly Pro Pro Gly Ala Gln
                    565                 570                 575
Gly Pro Ala Gly Pro Gly Gly Ser Arg Gly Asp Pro Gly Pro Pro Gly
                580                 585                 590
Ala His Gly Pro Ala Gly Pro Lys Gly Ala His Gly Pro Ala Gly Pro
            595                 600                 605
Lys Gly Ala Met Asp Pro Gly Arg Tyr Gln Leu Ser Ala Gly Arg Tyr
```

|     | 610 |     |     |     | 615 |     |     |     | 620 |
| --- | --- | --- | --- | --- | --- | --- | --- | --- | --- |
| His | Tyr | Gln | Leu | Val | Trp | Cys | Gln | Lys |     |
| 625 |     |     |     |     | 630 |     |     |     |     |

( 2 ) INFORMATION FOR SEQ ID NO:74:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:74:

GTGCACAGGG ACCGGCGGGT CCAGGCGGTG CTCAAGGACC GGCAGGCCCT TAATTAAG 58

( 2 ) INFORMATION FOR SEQ ID NO:75:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:75:

GCACCTTAAT TAAGGGCCTG CCGGTCCTTG AGCACCGCCT GGACCCGCCG GTCCCTGT 58

( 2 ) INFORMATION FOR SEQ ID NO:76:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:76:

GCCCTGGTGG CGCTCAAGGT CCGGCTGGCC CAGGAGGCGC GCAGGGTCCG GCAGGTCCGG 60

GAG 63

( 2 ) INFORMATION FOR SEQ ID NO:77:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:77:

GCACCTCCCG GACCTGCCGG ACCCTGCGCG CCTCCTGGGC CAGCCGGACC TTGAGCGCCA 60

CCAG 64

( 2 ) INFORMATION FOR SEQ ID NO:78:

( i ) SEQUENCE CHARACTERISTICS:
        ( A ) LENGTH: 108 base pairs
        ( B ) TYPE: nucleic acid
        ( C ) STRANDEDNESS: double (D) TOPOLOGY: linear (ii) MOLECULE TYPE: other nucleic acid
  (A) DESCRIPTION: /desc = "synthetic"

(xi) SEQUENCE DESCRIPTION: SEQ ID NO:78:

```
GGTGCACAGG   GACCGGCGGG   TCCAGGCGGT   GCTCAAGGAC   CGGCAGGCCC   TGGTGGCGCT        60

CAAGGTCCGG   CTGGCCCAGG   AGGCGCGCAG   GGTCCGGCAG   GTCCGGGA                      108
```

(2) INFORMATION FOR SEQ ID NO:79:

(i) SEQUENCE CHARACTERISTICS:
    (A) LENGTH: 36 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:79:

```
Gly  Ala  Gln  Gly  Pro  Ala  Gly  Pro  Gly  Gly  Ala  Gln  Gly  Pro  Ala  Gly
1                  5                        10                       15

Pro  Gly  Gly  Ala  Gln  Gly  Pro  Ala  Gly  Pro  Gly  Gly  Ala  Gln  Gly  Pro
                20                       25                      30

Ala  Gly  Pro  Gly
            35
```

(2) INFORMATION FOR SEQ ID NO:80:

(i) SEQUENCE CHARACTERISTICS:
    (A) LENGTH: 1065 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:80:

```
Met  Asp  Pro  Val  Val  Leu  Gln  Arg  Arg  Asp  Trp  Glu  Asn  Pro  Gly  Val
1                  5                        10                       15

Thr  Gln  Leu  Asn  Arg  Leu  Ala  Ala  His  Pro  Pro  Phe  Ala  Ser  Asp  Pro
                20                       25                      30

Met  Gly  Ala  His  Gly  Pro  Ala  Gly  Pro  Lys  Gly  Ala  His  Gly  Pro  Ala
            35                       40                       45

Gly  Pro  Lys  Gly  Ala  Gln  Gly  Pro  Ala  Gly  Pro  Gly  Gly  Ala  Gln  Gly
       50                       55                       60

Pro  Ala  Gly  Pro  Gly  Gly  Ala  Gln  Gly  Pro  Ala  Gly  Pro  Gly  Gly  Ala
65                       70                       75                       80

Gln  Gly  Pro  Ala  Gly  Pro  Gly  Gly  Ala  Gln  Gly  Pro  Ala  Gly  Pro  Gly
                85                       90                       95

Gly  Ala  Gln  Gly  Pro  Ala  Gly  Pro  Gly  Gly  Ala  Gln  Gly  Pro  Ala  Gly
            100                      105                      110

Pro  Gly  Gly  Ala  Gln  Gly  Pro  Ala  Gly  Pro  Gly  Gly  Ala  Gln  Gly  Pro
            115                      120                      125

Ala  Gly  Pro  Gly  Gly  Ala  Gln  Gly  Pro  Ala  Gly  Pro  Gly  Gly  Ala  Gln
            130                      135                      140

Gly  Pro  Ala  Gly  Pro  Gly  Gly  Ala  Gln  Gly  Pro  Ala  Gly  Pro  Gly  Gly
145                      150                      155                      160

Ala  Gln  Gly  Pro  Ala  Gly  Pro  Gly  Gly  Ala  Gln  Gly  Pro  Ala  Gly  Pro
                165                      170                      175

Gly  Gly  Ala  Gln  Gly  Pro  Ala  Gly  Pro  Gly  Gly  Ala  Gln  Gly  Pro  Ala
```

```
                180                       185                       190
Gly  Pro  Gly  Gly  Ala  Gln  Gly  Pro  Ala  Gly  Pro  Gly  Gly  Ala  Gln  Gly
          195                       200                       205
Pro  Ala  Gly  Pro  Gly  Gly  Ala  Gln  Gly  Pro  Ala  Gly  Pro  Gly  Gly  Ala
     210                       215                       220
Gln  Gly  Pro  Ala  Gly  Pro  Gly  Gly  Ala  Gln  Gly  Pro  Ala  Gly  Pro  Gly
225                       230                       235                       240
Gly  Ala  Gln  Gly  Pro  Ala  Gly  Pro  Gly  Gly  Ala  Gln  Gly  Pro  Ala  Gly
               245                       250                            255
Pro  Gly  Gly  Ala  Gln  Gly  Pro  Ala  Gly  Pro  Gly  Gly  Ala  His  Gly  Pro
                    260                       265                       270
Ala  Gly  Pro  Lys  Gly  Ala  His  Gly  Pro  Ala  Gly  Pro  Lys  Gly  Ala  His
          275                       280                       285
Gly  Pro  Ala  Gly  Pro  Lys  Gly  Ala  His  Gly  Pro  Ala  Gly  Pro  Lys  Gly
     290                       295                       300
Ala  Gln  Gly  Pro  Ala  Gly  Pro  Gly  Gly  Ala  Gln  Gly  Pro  Ala  Gly  Pro
305                       310                       315                       320
Gly  Gly  Ala  Gln  Gly  Pro  Ala  Gly  Pro  Gly  Gly  Ala  Gln  Gly  Pro  Ala
               325                       330                       335
Gly  Pro  Gly  Gly  Ala  Gln  Gly  Pro  Ala  Gly  Pro  Gly  Gly  Ala  Gln  Gly
               340                       345                       350
Pro  Ala  Gly  Pro  Gly  Gly  Ala  Gln  Gly  Pro  Ala  Gly  Pro  Gly  Gly  Ala
          355                       360                       365
Gln  Gly  Pro  Ala  Gly  Pro  Gly  Gly  Ala  Gln  Gly  Pro  Ala  Gly  Pro  Gly
     370                       375                       380
Gly  Ala  Gln  Gly  Pro  Ala  Gly  Pro  Gly  Gly  Ala  Gln  Gly  Pro  Ala  Gly
385                       390                       395                       400
Pro  Gly  Gly  Ala  Gln  Gly  Pro  Ala  Gly  Pro  Gly  Gly  Ala  Gln  Gly  Pro
               405                       410                       415
Ala  Gly  Pro  Gly  Gly  Ala  Gln  Gly  Pro  Ala  Gly  Pro  Gly  Gly  Ala  Gln
               420                       425                       430
Gly  Pro  Ala  Gly  Pro  Gly  Gly  Ala  Gln  Gly  Pro  Ala  Gly  Pro  Gly  Gly
          435                       440                       445
Ala  Gln  Gly  Pro  Ala  Gly  Pro  Gly  Gly  Ala  Gln  Gly  Pro  Ala  Gly  Pro
     450                       455                       460
Gly  Gly  Ala  Gln  Gly  Pro  Ala  Gly  Pro  Gly  Gly  Ala  Gln  Gly  Pro  Ala
465                       470                       475                       480
Gly  Pro  Gly  Gly  Ala  Gln  Gly  Pro  Ala  Gly  Pro  Gly  Gly  Ala  Gln  Gly
               485                       490                       495
Pro  Ala  Gly  Pro  Gly  Gly  Ala  Gln  Gly  Pro  Ala  Gly  Pro  Gly  Gly  Ala
               500                       505                       510
Gln  Gly  Pro  Ala  Gly  Pro  Gly  Gly  Ala  His  Gly  Pro  Ala  Gly  Pro  Lys
          515                       520                       525
Gly  Ala  His  Gly  Pro  Ala  Gly  Pro  Lys  Gly  Ala  His  Gly  Pro  Ala  Gly
          530                       535                       540
Pro  Lys  Gly  Ala  His  Gly  Pro  Ala  Gly  Pro  Lys  Gly  Ala  Gln  Gly  Pro
545                       550                       555                       560
Ala  Gly  Pro  Gly  Gly  Ala  Gln  Gly  Pro  Ala  Gly  Pro  Gly  Gly  Ala  Gln
               565                       570                       575
Gly  Pro  Ala  Gly  Pro  Gly  Gly  Ala  Gln  Gly  Pro  Ala  Gly  Pro  Gly  Gly
               580                       585                       590
Ala  Gln  Gly  Pro  Ala  Gly  Pro  Gly  Gly  Ala  Gln  Gly  Pro  Ala  Gly  Pro
          595                       600                       605
```

```
Gly  Gly  Ala  Gln  Gly  Pro  Ala  Gly  Pro  Gly  Gly  Ala  Gln  Gly  Pro  Ala
     610                     615                      620
Gly  Pro  Gly  Gly  Ala  Gln  Gly  Pro  Ala  Gly  Pro  Gly  Gly  Ala  Gln  Gly
625                      630                      635                      640
Pro  Ala  Gly  Pro  Gly  Gly  Ala  Gln  Gly  Pro  Ala  Gly  Pro  Gly  Gly  Ala
                    645                      650                      655
Gln  Gly  Pro  Ala  Gly  Pro  Gly  Gly  Ala  Gln  Gly  Pro  Ala  Gly  Pro  Gly
               660                      665                      670
Gly  Ala  Gln  Gly  Pro  Ala  Gly  Pro  Gly  Gly  Ala  Gln  Gly  Pro  Ala  Gly
          675                      680                      685
Pro  Gly  Gly  Ala  Gln  Gly  Pro  Ala  Gly  Pro  Gly  Gly  Ala  Gln  Gly  Pro
     690                      695                      700
Ala  Gly  Pro  Gly  Gly  Ala  Gln  Gly  Pro  Ala  Gly  Pro  Gly  Gly  Ala  Gln
705                      710                      715                      720
Gly  Pro  Ala  Gly  Pro  Gly  Gly  Ala  Gln  Gly  Pro  Ala  Gly  Pro  Gly  Gly
                    725                      730                      735
Ala  Gln  Gly  Pro  Ala  Gly  Pro  Gly  Gly  Ala  Gln  Gly  Pro  Ala  Gly  Pro
               740                      745                      750
Gly  Gly  Ala  Gln  Gly  Pro  Ala  Gly  Pro  Gly  Gly  Ala  Gln  Gly  Pro  Ala
          755                      760                      765
Gly  Pro  Gly  Gly  Ala  His  Gly  Pro  Ala  Gly  Pro  Lys  Gly  Ala  His  Gly
     770                      775                      780
Pro  Ala  Gly  Pro  Lys  Gly  Ala  His  Gly  Pro  Ala  Gly  Pro  Lys  Gly  Ala
785                      790                      795                      800
His  Gly  Pro  Ala  Gly  Pro  Lys  Gly  Ala  Gln  Gly  Pro  Ala  Gly  Pro  Gly
                    805                      810                      815
Gly  Ala  Gln  Gly  Pro  Ala  Gly  Pro  Gly  Gly  Ala  Gln  Gly  Pro  Ala  Gly
               820                      825                      830
Pro  Gly  Gly  Ala  Gln  Gly  Pro  Ala  Gly  Pro  Gly  Gly  Ala  Gln  Gly  Pro
          835                      840                      845
Ala  Gly  Pro  Gly  Gly  Ala  Gln  Gly  Pro  Ala  Gly  Pro  Gly  Gly  Ala  Gln
     850                      855                      860
Gly  Pro  Ala  Gly  Pro  Gly  Gly  Ala  Gln  Gly  Pro  Ala  Gly  Pro  Gly  Gly
865                      870                      875                      880
Ala  Gln  Gly  Pro  Ala  Gly  Pro  Gly  Gly  Ala  Gln  Gly  Pro  Ala  Gly  Pro
                    885                      890                      895
Gly  Gly  Ala  Gln  Gly  Pro  Ala  Gly  Pro  Gly  Gly  Ala  Gln  Gly  Pro  Ala
               900                      905                      910
Gly  Pro  Gly  Gly  Ala  Gln  Gly  Pro  Ala  Gly  Pro  Gly  Gly  Ala  Gln  Gly
          915                      920                      925
Pro  Ala  Gly  Pro  Gly  Gly  Ala  Gln  Gly  Pro  Ala  Gly  Pro  Gly  Gly  Ala
     930                      935                      940
Gln  Gly  Pro  Ala  Gly  Pro  Gly  Gly  Ala  Gln  Gly  Pro  Ala  Gly  Pro  Gly
945                      950                      955                      960
Gly  Ala  Gln  Gly  Pro  Ala  Gly  Pro  Gly  Gly  Ala  Gln  Gly  Pro  Ala  Gly
                    965                      970                      975
Pro  Gly  Gly  Ala  Gln  Gly  Pro  Ala  Gly  Pro  Gly  Gly  Ala  Gln  Gly  Pro
               980                      985                      990
Ala  Gly  Pro  Gly  Gly  Ala  Gln  Gly  Pro  Ala  Gly  Pro  Gly  Gly  Ala  Gln
     995                      1000                     1005
Gly  Pro  Ala  Gly  Pro  Gly  Gly  Ala  Gln  Gly  Pro  Ala  Gly  Pro  Gly  Gly
1010                     1015                     1020
Ala  His  Gly  Pro  Ala  Gly  Pro  Lys  Gly  Ala  His  Gly  Pro  Ala  Gly  Pro
1025                     1030                     1035                     1040
```

```
          Lys  Gly  Ala  Met  Asp  Pro  Gly  Arg  Tyr  Gln  Leu  Ser  Ala  Gly  Arg  Tyr
                         1045                    1050                    1055

His  Tyr  Gln  Leu  Val  Trp  Cys  Cys  Lys
                         1060                    1065
```

( 2 ) INFORMATION FOR SEQ ID NO:81:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:81:

```
GCTATGTTTA  AACCACGTGT  TCGCGATCCG  GGTGCCGATC  CAGGCCTGCG  ATATCAGTAC         60

GTA                                                                            63
```

( 2 ) INFORMATION FOR SEQ ID NO:82:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:82:

```
          Ala  Met  Phe  Lys  Pro  Arg  Val  Arg  Asp  Pro  Gly  Ala  Asp  Pro  Gly  Leu
          1                   5                    10                   15

Arg  Tyr  Gln  Tyr  Val
                         20
```

( 2 ) INFORMATION FOR SEQ ID NO:83:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:83:

```
GTGCCCCTGG  CGCTCCGGGT  TCTCAAGGTG  CACCGGGTCT  GCAGAAAGGG  CTCG               54
```

( 2 ) INFORMATION FOR SEQ ID NO:84:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:84:

```
GCACCGAGCC  CTTTCTGCAG  ACCCGGTGCA  CCTTGAGAAC  CCGGAGCGCC  AGGG               54
```

( 2 ) INFORMATION FOR SEQ ID NO:85:

( i ) SEQUENCE CHARACTERISTICS:

(A) LENGTH: 52 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:85:

GGGTGCACCG GGAGCGCCAG GTAGCCAGGG TGCACCGGGA TTGCAGGGGG CT 52

(2) INFORMATION FOR SEQ ID NO:86:

(i) SEQUENCE CHARACTERISTICS:
(A) LENGTH: 52 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:86:

CCCTGCAATC CCGGTGCACC CTGGCTACCT GGCGCTCCCG GTGCACCCTG CA 52

(2) INFORMATION FOR SEQ ID NO:87:

(i) SEQUENCE CHARACTERISTICS:
(A) LENGTH: 49 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:87:

CCGGGTGCAC CAGGTAGCCA GGGAGCACCG GGTCTGCAAG GAGCACCGG 49

(2) INFORMATION FOR SEQ ID NO:88:

(i) SEQUENCE CHARACTERISTICS:
(A) LENGTH: 50 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:88:

GTGCTCCTTG CAGACCGCCT GCTCCCTGGC TACCTGGTCG ACCCGGAGCC 50

(2) INFORMATION FOR SEQ ID NO:89:

(i) SEQUENCE CHARACTERISTICS:
(A) LENGTH: 61 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic"

(x i) SEQUENCE DESCRIPTION: SEQ ID NO:89:

CAAACACCGG GTGCACCGGG ATCCCAGGGC GCTCCGGGCC TGCAAGGTGC CAGGCCTCGA 60
T 61

(2) INFORMATION FOR SEQ ID NO:90:

( i ) SEQUENCE CHARACTERISTICS:
  ( A ) LENGTH: 65 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:90:

```
TACGAGGCCT GGCACCTTGC AGGCCCGGAG CGCCCTGGGA TCCCGGTGCA CCCGGTGTTT        60
GAGCC                                                                    65
```

( 2 ) INFORMATION FOR SEQ ID NO:91:

( i ) SEQUENCE CHARACTERISTICS:
  ( A ) LENGTH: 168 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:91:

```
GGTGCCCCTG GCGCTCCGGG TTCTCAAGGT GCACCGGGTC TGCAGGGTGC ACCGGGAGCG        60
CCAGGTAGCC AGGGTGCACC GGGATTGCAG GGGGCTCCGG GTGCACCAGG TAGCCAGGGA       120
GCACCGGGTG CACCGGGATC CCAGGGCGCT CCGGGCCTGC AAGGTGCC                    168
```

( 2 ) INFORMATION FOR SEQ ID NO:92:

( i ) SEQUENCE CHARACTERISTICS:
  ( A ) LENGTH: 54 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:92:

```
Gly Ala Pro Gly Ala Pro Gly Ser Gln Gly Ala Pro Gly Leu Gln Gly
 1               5                  10                  15
Ala Pro Gly Ala Pro Gly Ser Gln Gly Ala Pro Gly Leu Gln Gly Ala
            20                  25                  30
Pro Gly Ala Pro Gly Ser Gln Gly Ala Pro Gly Ala Pro Gly Ser Gln
        35                  40                  45
Gly Ala Pro Gly Leu Gln
    50
```

( 2 ) INFORMATION FOR SEQ ID NO:93:

( i ) SEQUENCE CHARACTERISTICS:
  ( A ) LENGTH: 186 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc = "synthetic"

( x i ) SEQUENCE DESCRIPTION: SEQ ID NO:93:

```
GGTGCCCCTG GCGCTCCGGG TTCTCAAGGT GCACCGGGTC TGCAGGGTGC ACCGGGAGCG        60
CCAGGTAGCC AGGGTGCACC GGGATTGCAG GGGGCTCCGG GTGCACCAGG TAGCCAGGGA       120
GCACCGGGTC TGCAAGGAGC ACCGGGTGCA CCGGGATCCC AGGGCGCTCC GGGCCTGCAA       180
```

GGTGCC 186

( 2 ) INFORMATION FOR SEQ ID NO:94:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

```
Gly Ala Pro Gly Ala Pro Gly Ser Gln Gly Ala Pro Gly Leu Gln Gly
  1               5                  10                  15
Ala Pro Gly Ala Pro Gly Ser Gln Gly Ala Pro Gly Leu Gln Gly Ala
             20                  25                  30
Pro Gly Ala Pro Gly Ser Gln Gly Ala Pro Gly Leu Gln Gly Ala Pro
         35                  40                  45
Gly Ala Pro Gly Ser Gln Gly Ala Pro Gly Leu Gln
         50                  55                  60
```

( 2 ) INFORMATION FOR SEQ ID NO:95:

( i ) SEQUENCE CHARACTERISTICS:
        ( A ) LENGTH: 1077 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:95:

```
Met Asp Pro Val Val Leu Gln Arg Arg Asp Trp Glu Asn Pro Gly Val
  1               5                  10                  15
Thr Gln Leu Asn Arg Leu Ala Ala His Pro Pro Phe Ala Ser Asp Pro
             20                  25                  30
Met Gly Ala Pro Gly Ala Pro Gly Ser Gln Gly Ala Pro Gly Leu Gln
         35                  40                  45
Gly Ala Pro Gly Ala Pro Gly Ser Gln Gly Ala Pro Gly Leu Gln Gly
         50                  55                  60
Ala Pro Gly Ala Pro Gly Ser Gln Gly Ala Pro Gly Leu Gln Gly Ala
 65                  70                  75                  80
Pro Gly Ala Pro Gly Ser Gln Gly Ala Pro Gly Leu Gln Gly Ala Pro
             85                  90                  95
Gly Ala Pro Gly Ser Gln Gly Ala Pro Gly Leu Gln Gly Ala Pro Gly
            100                 105                 110
Ala Pro Gly Ser Gln Gly Ala Pro Gly Leu Gln Gly Ala Pro Gly Ala
         115                 120                 125
Pro Gly Ser Gln Gly Ala Pro Gly Leu Gln Gly Ala Pro Gly Ala Pro
         130                 135                 140
Gly Ser Gln Gly Ala Pro Gly Leu Gln Gly Ala Pro Gly Ala Pro Gly
145                 150                 155                 160
Ser Gln Gly Ala Pro Gly Leu Gln Gly Ala Pro Gly Ala Pro Gly Ser
                 165                 170                 175
Gln Gly Ala Pro Gly Leu Gln Gly Ala Pro Gly Ala Pro Gly Ser Gln
             180                 185                 190
Gly Ala Pro Gly Leu Gln Gly Ala Pro Gly Ala Pro Gly Ser Gln Gly
         195                 200                 205
```

```
Ala  Pro  Gly  Leu  Gln  Gly  Ala  Pro  Gly  Ala  Pro  Gly  Ser  Gln  Gly  Ala
     210                          215                 220

Pro  Gly  Leu  Gln  Gly  Ala  Pro  Gly  Ala  Pro  Gly  Ser  Gln  Gly  Ala  Pro
225                      230                      235                          240

Gly  Leu  Gln  Gly  Ala  Pro  Gly  Ala  Pro  Gly  Ser  Gln  Gly  Ala  Pro  Gly
                    245                      250                      255

Leu  Gln  Gly  Ala  Pro  Gly  Ala  Pro  Gly  Ser  Gln  Gly  Ala  Pro  Gly  Leu
               260                      265                      270

Gln  Gly  Ala  Pro  Gly  Ala  Pro  Gly  Ser  Gln  Gly  Ala  Pro  Gly  Leu  Gln
          275                      280                      285

Gly  Ala  Pro  Gly  Ala  Pro  Gly  Ser  Gln  Gly  Ala  Pro  Gly  Leu  Gln  Gly
     290                      295                      300

Ala  Pro  Gly  Ala  Pro  Gly  Ser  Gln  Gly  Ala  Pro  Gly  Leu  Gln  Gly  Ala
305                      310                      315                          320

Pro  Gly  Ala  Pro  Gly  Ser  Gln  Gly  Ala  Pro  Gly  Leu  Gln  Gly  Ala  Pro
                    325                      330                      335

Gly  Ala  Pro  Gly  Ser  Gln  Gly  Ala  Pro  Gly  Leu  Gln  Gly  Ala  Pro  Gly
               340                      345                      350

Ala  Pro  Gly  Ser  Gln  Gly  Ala  Pro  Gly  Leu  Gln  Gly  Ala  Pro  Gly  Ala
          355                      360                      365

Pro  Gly  Ser  Gln  Gly  Ala  Pro  Gly  Leu  Gln  Gly  Ala  Pro  Gly  Ala  Pro
     370                      375                      380

Gly  Ser  Gln  Gly  Ala  Pro  Gly  Leu  Gln  Gly  Ala  Pro  Gly  Ala  Pro  Gly
385                      390                      395                          400

Ser  Gln  Gly  Ala  Pro  Gly  Leu  Gln  Gly  Ala  Pro  Gly  Ala  Pro  Gly  Ser
                    405                      410                      415

Gln  Gly  Ala  Pro  Gly  Leu  Gln  Gly  Ala  Pro  Gly  Ala  Pro  Gly  Ser  Gln
               420                      425                      430

Gly  Ala  Pro  Gly  Leu  Gln  Gly  Ala  Pro  Gly  Ala  Pro  Gly  Ser  Gln  Gly
          435                      440                      445

Ala  Pro  Gly  Leu  Gln  Gly  Ala  Pro  Gly  Ala  Pro  Gly  Ser  Gln  Gly  Ala
     450                      455                      460

Pro  Gly  Leu  Gln  Gly  Ala  Pro  Gly  Ala  Pro  Gly  Ser  Gln  Gly  Ala  Pro
465                      470                      475                          480

Gly  Leu  Gln  Gly  Ala  Pro  Gly  Ala  Pro  Gly  Ser  Gln  Gly  Ala  Pro  Gly
                    485                      490                      495

Leu  Gln  Gly  Ala  Pro  Gly  Ala  Pro  Gly  Ser  Gln  Gly  Ala  Pro  Gly  Leu
               500                      505                      510

Gln  Gly  Ala  Pro  Gly  Ala  Pro  Gly  Ser  Gln  Gly  Ala  Pro  Gly  Leu  Gln
          515                      520                      525

Gly  Ala  Pro  Gly  Ala  Pro  Gly  Ser  Gln  Gly  Ala  Pro  Gly  Leu  Gln  Gly
     530                      535                      540

Ala  Pro  Gly  Ala  Pro  Gly  Ser  Gln  Gly  Ala  Pro  Gly  Leu  Gln  Gly  Ala
545                      550                      555                          560

Pro  Gly  Ala  Pro  Gly  Ser  Gln  Gly  Ala  Pro  Gly  Leu  Gln  Gly  Ala  Pro
                    565                      570                      575

Gly  Ala  Pro  Gly  Ser  Gln  Gly  Ala  Pro  Gly  Leu  Gln  Gly  Ala  Pro  Gly
               580                      585                      590

Ala  Pro  Gly  Ser  Gln  Gly  Ala  Pro  Gly  Leu  Gln  Gly  Ala  Pro  Gly  Ala
          595                      600                      605

Pro  Gly  Ser  Gln  Gly  Ala  Pro  Gly  Leu  Gln  Gly  Ala  Pro  Gly  Ala  Pro
     610                      615                      620

Gly  Ser  Gln  Gly  Ala  Pro  Gly  Leu  Gln  Gly  Ala  Pro  Gly  Ala  Pro  Gly
625                      630                      635                          640
```

```
Ser Gln Gly Ala Pro Gly Leu Gln Gly Ala Pro Gly Ala Pro Gly Ser
            645                 650                 655
Gln Gly Ala Pro Gly Leu Gln Gly Ala Pro Gly Ala Pro Gly Ser Gln
            660                 665                 670
Gly Ala Pro Gly Leu Gln Gly Ala Pro Gly Ala Pro Gly Ser Gln Gly
            675                 680                 685
Ala Pro Gly Leu Gln Gly Ala Pro Gly Ala Pro Gly Ser Gln Gly Ala
            690                 695                 700
Pro Gly Leu Gln Gly Ala Pro Gly Ala Pro Gly Ser Gln Gly Ala Pro
705                 710                 715                 720
Gly Leu Gln Gly Ala Pro Gly Ala Pro Gly Ser Gln Gly Ala Pro Gly
                725                 730                 735
Leu Gln Gly Ala Pro Gly Ala Pro Gly Ser Gln Gly Ala Pro Gly Leu
            740                 745                 750
Gln Gly Ala Pro Gly Ala Pro Gly Ser Gln Gly Ala Pro Gly Leu Gln
            755                 760                 765
Gly Ala Pro Gly Ala Pro Gly Ser Gln Gly Ala Pro Gly Leu Gln Gly
            770                 775                 780
Ala Pro Gly Ala Pro Gly Ser Gln Gly Ala Pro Gly Leu Gln Gly Ala
785                 790                 795                 800
Pro Gly Ala Pro Gly Ser Gln Gly Ala Pro Gly Leu Gln Gly Ala Pro
                805                 810                 815
Gly Ala Pro Gly Ser Gln Gly Ala Pro Gly Leu Gln Gly Ala Pro Gly
            820                 825                 830
Ala Pro Gly Ser Gln Gly Ala Pro Gly Leu Gln Gly Ala Pro Gly Ala
            835                 840                 845
Pro Gly Ser Gln Gly Ala Pro Gly Leu Gln Gly Ala Pro Gly Ala Pro
850                 855                 860
Gly Ser Gln Gly Ala Pro Gly Leu Gln Gly Ala Pro Gly Ala Pro Gly
865                 870                 875                 880
Ser Gln Gly Ala Pro Gly Leu Gln Gly Ala Pro Gly Ala Pro Gly Ser
                885                 890                 895
Gln Gly Ala Pro Gly Leu Gln Gly Ala Pro Gly Ala Pro Gly Ser Gln
            900                 905                 910
Gly Ala Pro Gly Leu Gln Gly Ala Pro Gly Ala Pro Gly Ser Gln Gly
            915                 920                 925
Ala Pro Gly Leu Gln Gly Ala Pro Gly Ala Pro Gly Ser Gln Gly Ala
            930                 935                 940
Pro Gly Leu Gln Gly Ala Pro Gly Ala Pro Gly Ser Gln Gly Ala Pro
945                 950                 955                 960
Gly Leu Gln Gly Ala Pro Gly Ala Pro Gly Ser Gln Gly Ala Pro Gly
                965                 970                 975
Leu Gln Gly Ala Pro Gly Ala Pro Gly Ser Gln Gly Ala Pro Gly Leu
            980                 985                 990
Gln Gly Ala Pro Gly Ala Pro Gly Ser Gln Gly Ala Pro Gly Leu Gln
            995                 1000                1005
Gly Ala Pro Gly Ala Pro Gly Ser Gln Gly Ala Pro Gly Leu Gln Gly
            1010                1015                1020
Ala Pro Gly Ala Pro Gly Ser Gln Gly Ala Pro Gly Leu Gln Gly Ala
            1025                1030                1035                1040
Pro Gly Ala Pro Gly Ser Gln Gly Ala Pro Gly Leu Gln Gly Ala Met
                1045                1050                1055
Asp Pro Gly Arg Tyr Gln Leu Ser Ala Gly Arg Tyr His Tyr Gln Leu
```

|  |  |  |
|---|---|---|
| 1060 | 1065 | 1070 |

Trp Val Cys Gln Lys
1075

( 2 ) INFORMATION FOR SEQ ID NO:96:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:96:

| | | | | | | |
|---|---|---|---|---|---|---|
| ATGGCAGCGA | AAGGGGACCG | GTGCCCCGGG | TACTCCTGGT | CCACAAGGTC | TGCCGGGAAG | 6 0 |
| CCCAGGGGCT | CCGGGTACTC | CAGGTCCGCA | AGGCCTGCCG | GGTTCACCGG | GTGCTCCGGG | 1 2 0 |
| AACTCCTGGC | CCGCAGGGCT | TGCCGGGATC | CCCAGGTGCA | CCAGGAACGC | CGGGACCTCA | 1 8 0 |
| GGGTCTTCCG | GGTAGCCCTG | GTGCCTTTCC | GCTAAAGTCC | TGCCGT | | 2 2 6 |

( 2 ) INFORMATION FOR SEQ ID NO:97:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:97:

AAGAAGGAGA TATCATATGG CAGCGAAAGG GGACC                        3 5

( 2 ) INFORMATION FOR SEQ ID NO:98:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:98:

CGCAGATCTT TAAATTACGG CAGGACTTTA GCGGAAA                    3 7

( 2 ) INFORMATION FOR SEQ ID NO:99:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:99:

| | | | | | | |
|---|---|---|---|---|---|---|
| GGTGCCCCGG | GTACTCCTGG | TCCACAAGGT | CTGCCGGGAA | GCCCAGGGGC | TCCGGGTACT | 6 0 |
| CCAGGTCCGC | AAGGCCTGCC | GGGTTCACCG | CCCCGAGGCC | CATGAGGTCC | AGGCGTTCCG | 1 2 0 |
| GACGGCCCAA | GTGGCGGTGC | TCCGGGAACT | CCTGGCCCGC | AGGGCTTGCC | GGGATCCCCA | 1 8 0 |
| GGTGCACCAG | GAACGCCGGG | ACCTCAGGGT | CTTCCGGGTA | GCCCTGGTGC | C | 2 3 1 |

( 2 ) INFORMATION FOR SEQ ID NO:100:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

```
Gly Ala Pro Gly Thr Pro Gly Pro Gln Gly Leu Pro Gly Ser Pro Gly
 1               5                  10                  15
Ala Pro Gly Thr Pro Gly Pro Gln Gly Leu Pro Gly Ser Pro Gly Ala
                20                  25                  30
Pro Gly Thr Pro Gly Pro Gln Gly Leu Pro Gly Ser Pro Gly Ala Pro
             35                  40                  45
Gly Thr Pro Gly Pro Gln Gly Leu Pro Gly Ser Pro Gly Ala
         50                  55                  60
```

( 2 ) INFORMATION FOR SEQ ID NO:101:

( i ) SEQUENCE CHARACTERISTICS:
        ( A ) LENGTH: 837 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:101:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
                20                  25                  30
Met Gly Ala Pro Gly Thr Pro Gly Pro Gln Gly Leu Pro Gly Ser Pro
             35                  40                  45
Gly Ala Pro Gly Thr Pro Gly Pro Gln Gly Leu Pro Gly Ser Pro Gly
         50                  55                  60
Ala Pro Gly Thr Pro Gly Pro Gln Gly Leu Pro Gly Ser Pro Gly Ala
 65                  70                  75                  80
Pro Gly Thr Pro Gly Pro Gln Gly Leu Pro Gly Ser Pro Gly Ala Pro
                 85                  90                  95
Gly Thr Pro Gly Pro Gln Gly Leu Pro Gly Ser Pro Gly Ala Pro Gly
             100                 105                 110
Thr Pro Gly Pro Gln Gly Leu Pro Gly Ser Pro Gly Ala Pro Gly Thr
         115                 120                 125
Pro Gly Pro Gln Gly Leu Pro Gly Ser Pro Gly Ala Pro Gly Thr Pro
     130                 135                 140
Gly Pro Gln Gly Leu Pro Gly Ser Pro Gly Ala Pro Gly Thr Pro Gly
145                 150                 155                 160
Pro Gln Gly Leu Pro Gly Ser Pro Gly Ala Pro Gly Thr Pro Gly Pro
                165                 170                 175
Gln Gly Leu Pro Gly Ser Pro Gly Ala Pro Gly Thr Pro Gly Pro Gln
            180                 185                 190
Gly Leu Pro Gly Ser Pro Gly Ala Pro Gly Thr Pro Gly Pro Gln Gly
        195                 200                 205
Leu Pro Gly Ser Pro Gly Ala Pro Gly Thr Pro Gly Pro Gln Gly Leu
    210                 215                 220
```

| | | | | | | | | | | | | | | |
|---|---|---|---|---|---|---|---|---|---|---|---|---|---|---|
| Pro | Gly | Ser | Pro | Gly | Ala | Pro | Gly | Thr | Pro | Gly | Pro | Gln | Gly | Leu | Pro |
| 225 | | | | 230 | | | | 235 | | | | | | 240 |
| Gly | Ser | Pro | Gly | Ala | Pro | Gly | Thr | Pro | Gly | Pro | Gln | Gly | Leu | Pro | Gly |
| | | | | 245 | | | | 250 | | | | | | 255 | |
| Ser | Pro | Gly | Ala | Pro | Gly | Thr | Pro | Gly | Pro | Gln | Gly | Leu | Pro | Gly | Ser |
| | | | 260 | | | | | 265 | | | | | | 270 | |
| Pro | Gly | Ala | Pro | Gly | Thr | Pro | Gly | Pro | Gln | Gly | Leu | Pro | Gly | Ser | Pro |
| | | 275 | | | | | | 280 | | | | | 285 | | |
| Gly | Ala | Pro | Gly | Thr | Pro | Gly | Pro | Gln | Gly | Leu | Pro | Gly | Ser | Pro | Gly |
| | 290 | | | | | | 295 | | | | | 300 | | | |
| Ala | Pro | Gly | Thr | Pro | Gly | Pro | Gln | Gly | Leu | Pro | Gly | Ser | Pro | Gly | Ala |
| 305 | | | | | 310 | | | | | 315 | | | | | 320 |
| Pro | Gly | Thr | Pro | Gly | Pro | Gln | Gly | Leu | Pro | Gly | Ser | Pro | Gly | Ala | Pro |
| | | | | 325 | | | | | 330 | | | | | 335 | |
| Gly | Thr | Pro | Gly | Pro | Gln | Gly | Leu | Pro | Gly | Ser | Pro | Gly | Ala | Pro | Gly |
| | | | 340 | | | | | 345 | | | | | 350 | | |
| Thr | Pro | Gly | Pro | Gln | Gly | Leu | Pro | Gly | Ser | Pro | Gly | Ala | Pro | Gly | Thr |
| | | 355 | | | | | 360 | | | | | 365 | | | |
| Pro | Gly | Pro | Gln | Gly | Leu | Pro | Gly | Ser | Pro | Gly | Ala | Pro | Gly | Thr | Pro |
| | 370 | | | | | 375 | | | | | 380 | | | | |
| Gly | Pro | Gln | Gly | Leu | Pro | Gly | Ser | Pro | Gly | Ala | Pro | Gly | Thr | Pro | Gly |
| 385 | | | | | 390 | | | | | 395 | | | | | 400 |
| Pro | Gln | Gly | Leu | Pro | Gly | Ser | Pro | Gly | Ala | Pro | Gly | Thr | Pro | Gly | Pro |
| | | | | 405 | | | | | 410 | | | | | 415 | |
| Gln | Gly | Leu | Pro | Gly | Ser | Pro | Gly | Ala | Pro | Gly | Thr | Pro | Gly | Pro | Gln |
| | | | 420 | | | | | 425 | | | | | 430 | | |
| Gly | Leu | Pro | Gly | Ser | Pro | Gly | Ala | Pro | Gly | Thr | Pro | Gly | Pro | Gln | Gly |
| | | 435 | | | | | 440 | | | | | 445 | | | |
| Leu | Pro | Gly | Ser | Pro | Gly | Ala | Pro | Gly | Thr | Pro | Gly | Pro | Gln | Gly | Leu |
| | 450 | | | | | 455 | | | | | 460 | | | | |
| Pro | Gly | Ser | Pro | Gly | Ala | Pro | Gly | Thr | Pro | Gly | Pro | Gln | Gly | Leu | Pro |
| 465 | | | | 470 | | | | 475 | | | | | | 480 | |
| Gly | Ser | Pro | Gly | Ala | Pro | Gly | Thr | Pro | Gly | Pro | Gln | Gly | Leu | Pro | Gly |
| | | | | 485 | | | | 490 | | | | | | 495 | |
| Ser | Pro | Gly | Ala | Pro | Gly | Thr | Pro | Gly | Pro | Gln | Gly | Leu | Pro | Gly | Ser |
| | | | 500 | | | | | 505 | | | | | | 510 | |
| Pro | Gly | Ala | Pro | Gly | Thr | Pro | Gly | Pro | Gln | Gly | Leu | Pro | Gly | Ser | Pro |
| | | 515 | | | | | | 520 | | | | | 525 | | |
| Gly | Ala | Pro | Gly | Thr | Pro | Gly | Pro | Gln | Gly | Leu | Pro | Gly | Ser | Pro | Gly |
| | 530 | | | | | 535 | | | | | | 540 | | | |
| Ala | Pro | Gly | Thr | Pro | Gly | Pro | Gln | Gly | Leu | Pro | Gly | Ser | Pro | Gly | Ala |
| 545 | | | | | 550 | | | | | 555 | | | | | 560 |
| Pro | Gly | Thr | Pro | Gly | Pro | Gln | Gly | Leu | Pro | Gly | Ser | Pro | Gly | Ala | Pro |
| | | | | 565 | | | | | 570 | | | | | 575 | |
| Gly | Thr | Pro | Gly | Pro | Gln | Gly | Leu | Pro | Gly | Ser | Pro | Gly | Ala | Pro | Gly |
| | | | 580 | | | | | 585 | | | | | 590 | | |
| Thr | Pro | Gly | Pro | Gln | Gly | Leu | Pro | Gly | Ser | Pro | Gly | Ala | Pro | Gly | Thr |
| | | 595 | | | | | 600 | | | | | 605 | | | |
| Pro | Gly | Pro | Gln | Gly | Leu | Pro | Gly | Ser | Pro | Gly | Ala | Pro | Gly | Thr | Pro |
| | 610 | | | | | 615 | | | | | 620 | | | | |
| Gly | Pro | Gln | Gly | Leu | Pro | Gly | Ser | Pro | Gly | Ala | Pro | Gly | Thr | Pro | Gly |
| 625 | | | | | 630 | | | | | 635 | | | | | 640 |
| Pro | Gln | Gly | Leu | Pro | Gly | Ser | Pro | Gly | Ala | Pro | Gly | Thr | Pro | Gly | Pro |

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 645 |     |     |     |     | 650 |     |     |     |     | 655 |
| Gln | Gly | Leu | Pro | Gly | Ser | Pro | Gly | Ala | Pro | Gly | Thr | Pro | Gly | Pro | Gln |
|     |     |     | 660 |     |     |     |     | 665 |     |     |     |     | 670 |     |
| Gly | Leu | Pro | Gly | Ser | Pro | Gly | Ala | Pro | Gly | Thr | Pro | Gly | Pro | Gln | Gly |
|     |     | 675 |     |     |     |     | 680 |     |     |     |     | 685 |     |     |
| Leu | Pro | Gly | Ser | Pro | Gly | Ala | Pro | Gly | Thr | Pro | Gly | Pro | Gln | Gly | Leu |
|     | 690 |     |     |     |     | 695 |     |     |     |     | 700 |     |     |     |
| Pro | Gly | Ser | Pro | Gly | Ala | Pro | Gly | Thr | Pro | Gly | Pro | Gln | Gly | Leu | Pro |
| 705 |     |     |     |     | 710 |     |     |     |     | 715 |     |     |     |     | 720 |
| Gly | Ser | Pro | Gly | Ala | Pro | Gly | Thr | Pro | Gly | Pro | Gln | Gly | Leu | Pro | Gly |
|     |     |     |     | 725 |     |     |     |     | 730 |     |     |     |     | 735 |     |
| Ser | Pro | Gly | Ala | Pro | Gly | Thr | Pro | Gly | Pro | Gln | Gly | Leu | Pro | Gly | Ser |
|     |     |     | 740 |     |     |     |     | 745 |     |     |     |     | 750 |     |     |
| Pro | Gly | Ala | Pro | Gly | Thr | Pro | Gly | Pro | Gln | Gly | Leu | Pro | Gly | Ser | Pro |
|     |     | 755 |     |     |     |     | 760 |     |     |     |     | 765 |     |     |     |
| Gly | Ala | Pro | Gly | Thr | Pro | Gly | Pro | Gln | Gly | Leu | Pro | Gly | Ser | Pro | Gly |
|     | 770 |     |     |     |     | 775 |     |     |     |     | 780 |     |     |     |     |
| Ala | Pro | Gly | Thr | Pro | Gly | Pro | Gln | Gly | Leu | Pro | Gly | Ser | Pro | Gly | Ala |
| 785 |     |     |     |     | 790 |     |     |     |     | 795 |     |     |     |     | 800 |
| Pro | Gly | Thr | Pro | Gly | Pro | Gln | Gly | Leu | Pro | Gly | Ser | Pro | Gly | Ala | Met |
|     |     |     |     | 805 |     |     |     |     | 810 |     |     |     |     | 815 |     |
| Asp | Pro | Gly | Arg | Tyr | Gln | Leu | Ser | Ala | Gly | Arg | Tyr | His | Tyr | Gln | Leu |
|     |     |     | 820 |     |     |     |     | 825 |     |     |     |     | 830 |     |     |
| Val | Trp | Cys | Gln | Lys |     |     |     |     |     |     |     |     |     |     |     |
|     |     | 835 |     |     |     |     |     |     |     |     |     |     |     |     |     |

( 2 ) INFORMATION FOR SEQ ID NO:102:

( i ) SEQUENCE CHARACTERISTICS:
        ( A ) LENGTH: 417 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:102:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Pro | Val | Val | Leu | Gln | Arg | Arg | Asp | Trp | Glu | Asn | Pro | Gly | Val |
| 1   |     |     |     | 5   |     |     |     |     | 10  |     |     |     |     | 15  |     |
| Thr | Gln | Leu | Asn | Arg | Leu | Ala | Ala | His | Pro | Pro | Phe | Ala | Ser | Asp | Pro |
|     |     |     | 20  |     |     |     |     | 25  |     |     |     |     | 30  |     |     |
| Met | Gly | Ala | Pro | Gly | Thr | Pro | Gly | Pro | Gln | Gly | Leu | Pro | Gly | Ser | Pro |
|     |     | 35  |     |     |     |     | 40  |     |     |     |     | 45  |     |     |     |
| Gly | Ala | Pro | Gly | Thr | Pro | Gly | Pro | Gln | Gly | Leu | Pro | Gly | Ser | Pro | Gly |
|     | 50  |     |     |     |     | 55  |     |     |     |     | 60  |     |     |     |     |
| Ala | Pro | Gly | Thr | Pro | Gly | Pro | Gln | Gly | Leu | Pro | Gly | Ser | Pro | Gly | Ala |
| 65  |     |     |     |     | 70  |     |     |     |     | 75  |     |     |     |     | 80  |
| Pro | Gly | Thr | Pro | Gly | Pro | Gln | Gly | Leu | Pro | Gly | Ser | Pro | Gly | Ala | Pro |
|     |     |     |     | 85  |     |     |     |     | 90  |     |     |     |     | 95  |     |
| Gly | Thr | Pro | Gly | Pro | Gln | Gly | Leu | Pro | Gly | Ser | Pro | Gly | Ala | Pro | Gly |
|     |     |     | 100 |     |     |     |     | 105 |     |     |     |     | 110 |     |     |
| Thr | Pro | Gly | Pro | Gln | Gly | Leu | Pro | Gly | Ser | Pro | Gly | Ala | Pro | Gly | Thr |
|     |     | 115 |     |     |     |     | 120 |     |     |     |     | 125 |     |     |     |
| Pro | Gly | Pro | Gln | Gly | Leu | Pro | Gly | Ser | Pro | Gly | Ala | Pro | Gly | Thr | Pro |
|     | 130 |     |     |     |     | 135 |     |     |     |     | 140 |     |     |     |     |
| Gly | Pro | Gln | Gly | Leu | Pro | Gly | Ser | Pro | Gly | Ala | Pro | Gly | Thr | Pro | Gly |
| 145 |     |     |     |     | 150 |     |     |     |     | 155 |     |     |     |     | 160 |

Pro Gln Gly Leu Pro Gly Ser Pro Gly Ala Pro Gly Thr Pro Gly Pro
                165                 170                 175

Gln Gly Leu Pro Gly Ser Pro Gly Ala Pro Gly Thr Pro Gly Pro Gln
            180                 185                 190

Gly Leu Pro Gly Ser Pro Gly Ala Pro Gly Thr Pro Gly Pro Gln Gly
        195                 200                 205

Leu Pro Gly Ser Pro Gly Ala Pro Gly Thr Pro Gly Pro Gln Gly Leu
    210                 215                 220

Pro Gly Ser Pro Gly Ala Pro Gly Thr Pro Gly Pro Gln Gly Leu Pro
225                 230                 235                 240

Gly Ser Pro Gly Ala Pro Gly Thr Pro Gly Pro Gln Gly Leu Pro Gly
                245                 250                 255

Ser Pro Gly Ala Pro Gly Thr Pro Gly Pro Gln Gly Leu Pro Gly Ser
            260                 265                 270

Pro Gly Ala Pro Gly Thr Pro Gly Pro Gln Gly Leu Pro Gly Ser Pro
        275                 280                 285

Gly Ala Pro Gly Thr Pro Gly Pro Gln Gly Leu Pro Gly Ser Pro Gly
    290                 295                 300

Ala Pro Gly Thr Pro Gly Pro Gln Gly Leu Pro Gly Ser Pro Gly Ala
305                 310                 315                 320

Pro Gly Thr Pro Gly Pro Gln Gly Leu Pro Gly Ser Pro Gly Ala Pro
                325                 330                 335

Gly Thr Pro Gly Pro Gln Gly Leu Pro Gly Ser Pro Gly Ala Pro Gly
            340                 345                 350

Thr Pro Gly Pro Gln Gly Leu Pro Gly Ser Pro Gly Ala Pro Gly Thr
        355                 360                 365

Pro Gly Pro Gln Gly Leu Pro Gly Ser Pro Gly Ala Pro Gly Thr Pro
    370                 375                 380

Gly Pro Gln Gly Leu Pro Gly Ser Pro Gly Ala Met Asp Pro Gly Arg
385                 390                 395                 400

Tyr Gln Leu Ser Ala Gly Arg Tyr His Tyr Gln Leu Val Trp Cys Gln
                405                 410                 415

Lys ( 2 ) INFORMATION FOR SEQ ID NO:103:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:103:

Val Leu Ser Leu Ser Gln Ser Lys Val Leu Pro Val Pro Glu
1               5               10

( 2 ) INFORMATION FOR SEQ ID NO:104:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:104:

Gly Glu Gly Gln Gln His His Leu Gly Gly Ala Lys Gln Ala Gly Asp
1               5                       10                      15

Val (2) INFORMATION FOR SEQ ID NO:105:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Gly Glu Gly Gln Gln His His Leu Gly Gly Ala Arg Gln Ala Gly Asp
1               5                       10                      15

Val (2) INFORMATION FOR SEQ ID NO:106:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Gly Gly Ala Lys Gln Ala Gly Asp Val
1               5

(2) INFORMATION FOR SEQ ID NO:107:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Gly Ala Pro Gly Thr Pro Gly Pro Gln Gly Leu Pro Gly Ser Pro
1               5                       10                      15

(2) INFORMATION FOR SEQ ID NO:108:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

Gly Ala Pro Gly Thr Pro Gly Pro Gln Gly Leu Pro Gly Ser Pro Gly
1               5                       10                      15

Ala Pro Gly Thr Pro Gly Pro Gln Gly Leu Pro Gly Ser Pro Gly Ala
                20                      25                      30

Pro Gly Thr Pro Gly Pro Gln Gly Leu Pro Gly Ser Pro Gly Ala Pro
            35                      40                      45

Gly Thr Pro Gly Glu Gly Gln Gln His His Leu Gly Gly Ala Lys Gln
        50                      55                      60

```
        Ala  Gly  Asp  Val  Gly  Ser  Pro
         65                 70
```

( 2 ) INFORMATION FOR SEQ ID NO:109:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:109:

```
ATGGCAGCGA  AAGGGGACCG  TGCACCAGGA  ACGCCGGGAG  AAGGTCAACA  GCACCATCTT      60
GGTGGAGCGA  AACAGGCAGG  CGACGTCGGT  AGCCCTGGTG  CCTTTCCGCT  AAAGTCCTGC     120
CGT                                                                       123
```

( 2 ) INFORMATION FOR SEQ ID NO:110:

( i ) SEQUENCE CHARACTERISTICS:
        ( A ) LENGTH: 219 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "synthetic"

( x i ) SEQUENCE DESCRIPTION: SEQ ID NO:110:

```
GGTGCCCCGG  GTACTCCTGG  TCCACAAGGT  CTGCCGGGAA  GCCCAGGGGC  TCCGGGTACT      60
CCAGGTCCGC  AAGGCCTGCC  GGGTTCACCG  GGTGCTCCGG  GAACTCCTGG  CCCGCAGGGC     120
TTGCCGGGAT  CCCCAGGTGC  ACCAGGAACG  CCGGGAGAAG  GTCAACAGCA  CCATCTTGGT     180
GGAGCGAAAC  AGGCAGGCGA  CGTCGGTAGC  CCTGGTGCC                              219
```

( 2 ) INFORMATION FOR SEQ ID NO:111:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:111:

```
Gly  Ala  Pro  Gly  Thr  Pro  Gly  Pro  Gln  Gly  Leu  Pro  Gly  Ser  Pro  Gly
 1                    5                     10                        15
Ala  Pro  Gly  Thr  Pro  Gly  Pro  Gln  Gly  Leu  Pro  Gly  Ser  Pro  Gly  Ala
                    20                     25                        30
Pro  Gly  Thr  Pro  Gly  Pro  Gln  Gly  Leu  Pro  Gly  Ser  Pro  Gly  Ala  Pro
          35                     40                        45
Gly  Thr  Pro  Gly  Glu  Gly  Gln  Gln  His  His  Leu  Gly  Gly  Ala  Lys  Gln
     50                     55                        60
Ala  Gly  Asp  Val  Gly  Ser  Pro  Gly  Ala
 65                 70
```

( 2 ) INFORMATION FOR SEQ ID NO:112:

( i ) SEQUENCE CHARACTERISTICS:
        ( A ) LENGTH: 32 base pairs
        ( B ) TYPE: nucleic acid
        ( C ) STRANDEDNESS: single -continued ( D ) TOPOLOGY: linear ( i i ) MOLECULE TYPE: other nucleic acid
    ( A ) DESCRIPTION: /desc = "synthetic"

( x i ) SEQUENCE DESCRIPTION: SEQ ID NO:112:

GATCTTCGAT CTCATCACCA TCACCATCAC TA          32

( 2 ) INFORMATION FOR SEQ ID NO:113:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic"

( x i ) SEQUENCE DESCRIPTION: SEQ ID NO:113:

AGCTTAGTGA TGGTGATGGT GATGAGATCG AA          32

( 2 ) INFORMATION FOR SEQ ID NO:114:

( i ) SEQUENCE CHARACTERISTICS:
    ( A ) LENGTH: 762 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:114:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
                20                  25                  30
Met Gly Ala Pro Gly Thr Pro Gly Pro Gln Gly Leu Pro Gly Ser Pro
            35                  40                  45
Gly Ala Pro Gly Thr Pro Gly Pro Gln Gly Leu Pro Gly Ser Pro Gly
        50                  55                  60
Ala Pro Gly Thr Pro Gly Pro Gln Gly Leu Pro Gly Ser Pro Gly Ala
65                  70                  75                  80
Pro Gly Thr Pro Gly Glu Gly Gln Gln His His Leu Gly Gly Ala Lys
                85                  90                  95
Gln Ala Gly Asp Val Gly Ser Pro Gly Ala Pro Gly Thr Pro Gly Pro
            100                 105                 110
Gln Gly Leu Pro Gly Ser Pro Gly Ala Pro Gly Thr Pro Gly Pro Gln
        115                 120                 125
Gly Leu Pro Gly Ser Pro Gly Ala Pro Gly Thr Pro Gly Pro Gln Gly
        130                 135                 140
Leu Pro Gly Ser Pro Gly Ala Pro Gly Thr Pro Gly Glu Gly Gln Gln
145                 150                 155                 160
His His Leu Gly Gly Ala Lys Gln Ala Gly Asp Val Gly Ser Pro Gly
                165                 170                 175
Ala Pro Gly Thr Pro Gly Pro Gln Gly Leu Pro Gly Ser Pro Gly Ala
            180                 185                 190
Pro Gly Thr Pro Gly Pro Gln Gly Leu Pro Gly Ser Pro Gly Ala Pro
        195                 200                 205
Gly Thr Pro Gly Pro Gln Gly Leu Pro Gly Ser Pro Gly Ala Pro Gly
        210                 215                 220
```

```
Thr  Pro  Gly  Glu  Gly  Gln  Gln  His  His  Leu  Gly  Gly  Ala  Lys  Gln  Ala
225                 230                      235                      240

Gly  Asp  Val  Gly  Ser  Pro  Gly  Ala  Pro  Gly  Thr  Pro  Gly  Pro  Gln  Gly
                    245                      250                      255

Leu  Pro  Gly  Ser  Pro  Gly  Ala  Pro  Gly  Thr  Pro  Gly  Pro  Gln  Gly  Leu
                    260                      265                      270

Pro  Gly  Ser  Pro  Gly  Ala  Pro  Gly  Thr  Pro  Gly  Pro  Gln  Gly  Leu  Pro
               275                      280                      285

Gly  Ser  Pro  Gly  Ala  Pro  Gly  Thr  Pro  Gly  Glu  Gly  Gln  Gln  His  His
          290                      295                      300

Leu  Gly  Gly  Ala  Lys  Gln  Ala  Gly  Asp  Val  Gly  Ser  Pro  Gly  Ala  Pro
305                      310                      315                      320

Gly  Thr  Pro  Gly  Pro  Gln  Gly  Leu  Pro  Gly  Ser  Pro  Gly  Ala  Pro  Gly
                    325                      330                      335

Thr  Pro  Gly  Pro  Gln  Gly  Leu  Pro  Gly  Ser  Pro  Gly  Ala  Pro  Gly  Thr
                    340                      345                      350

Pro  Gly  Pro  Gln  Gly  Leu  Pro  Gly  Ser  Pro  Gly  Ala  Pro  Gly  Thr  Pro
          355                      360                      365

Gly  Glu  Gly  Gln  Gln  His  His  Leu  Gly  Gly  Ala  Lys  Gln  Ala  Gly  Asp
     370                      375                      380

Val  Gly  Ser  Pro  Gly  Ala  Pro  Gly  Thr  Pro  Gly  Pro  Gln  Gly  Leu  Pro
385                      390                      395                      400

Gly  Ser  Pro  Gly  Ala  Pro  Gly  Thr  Pro  Gly  Pro  Gln  Gly  Leu  Pro  Gly
                    405                      410                      415

Ser  Pro  Gly  Ala  Pro  Gly  Thr  Pro  Gly  Pro  Gln  Gly  Leu  Pro  Gly  Ser
               420                      425                      430

Pro  Gly  Ala  Pro  Gly  Thr  Pro  Gly  Glu  Gly  Gln  Gln  His  His  Leu  Gly
          435                      440                      445

Gly  Ala  Lys  Gln  Ala  Gly  Asp  Val  Gly  Ser  Pro  Gly  Ala  Pro  Gly  Thr
     450                      455                      460

Pro  Gly  Pro  Gln  Gly  Leu  Pro  Gly  Ser  Pro  Gly  Ala  Pro  Gly  Thr  Pro
465                      470                      475                      480

Gly  Pro  Gln  Gly  Leu  Pro  Gly  Ser  Pro  Gly  Ala  Pro  Gly  Thr  Pro  Gly
                    485                      490                      495

Pro  Gln  Gly  Leu  Pro  Gly  Ser  Pro  Gly  Ala  Pro  Gly  Thr  Pro  Gly  Glu
               500                      505                      510

Gly  Gln  Gln  His  His  Leu  Gly  Gly  Ala  Lys  Gln  Ala  Gly  Asp  Val  Gly
          515                      520                      525

Ser  Pro  Gly  Ala  Pro  Gly  Thr  Pro  Gly  Pro  Gln  Gly  Leu  Pro  Gly  Ser
     530                      535                      540

Pro  Gly  Ala  Pro  Gly  Thr  Pro  Gly  Pro  Gln  Gly  Leu  Pro  Gly  Ser  Pro
545                      550                      555                      560

Gly  Ala  Pro  Gly  Thr  Pro  Gly  Pro  Gln  Gly  Leu  Pro  Gly  Ser  Pro  Gly
                    565                      570                      575

Ala  Pro  Gly  Thr  Pro  Gly  Glu  Gly  Gln  Gln  His  His  Leu  Gly  Gly  Ala
                    580                      585                      590

Lys  Gln  Ala  Gly  Asp  Val  Gly  Ser  Pro  Gly  Ala  Pro  Gly  Thr  Pro  Gly
          595                      600                      605

Pro  Gln  Gly  Leu  Pro  Gly  Ser  Pro  Gly  Ala  Pro  Gly  Thr  Pro  Gly  Pro
          610                      615                      620

Gln  Gly  Leu  Pro  Gly  Ser  Pro  Gly  Ala  Pro  Gly  Thr  Pro  Gly  Pro  Gln
625                      630                      635                      640

Gly  Leu  Pro  Gly  Ser  Pro  Gly  Ala  Pro  Gly  Thr  Pro  Gly  Glu  Gly  Gln
                    645                      650                      655
```

Gln  His  His  Leu  Gly  Gly  Ala  Lys  Gln  Ala  Gly  Asp  Val  Gly  Ser  Pro
                           660                 665                      670

Gly  Ala  Pro  Gly  Thr  Pro  Gly  Pro  Gln  Gly  Leu  Pro  Gly  Ser  Pro  Gly
                      675                      680                      685

Ala  Pro  Gly  Thr  Pro  Gly  Pro  Gln  Gly  Leu  Pro  Gly  Ser  Pro  Gly  Ala
                 690                      695                      700

Pro  Gly  Thr  Pro  Gly  Pro  Gln  Gly  Leu  Pro  Gly  Ser  Pro  Gly  Ala  Pro
            705                      710                 715                           720

Gly  Thr  Pro  Gly  Glu  Gly  Gln  Gln  His  His  Leu  Gly  Gly  Ala  Lys  Gln
                           725                      730                      735

Ala  Gly  Asp  Val  Gly  Ser  Pro  Gly  Ala  Met  Asp  Pro  Gly  Arg  Tyr  Gln
                           740                      745                      750

Asp  Leu  Arg  Ser  His  His  His  His  His  His
                           755                      760

( 2 ) INFORMATION FOR SEQ ID NO:115:

( i ) SEQUENCE CHARACTERISTICS:
                ( A ) LENGTH: 71 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:115:

Gly  Ala  Pro  Gly  Thr  Pro  Gly  Pro  Gln  Gly  Leu  Pro  Gly  Ser  Pro  Gly
            1                   5                   10                       15

Ala  Pro  Gly  Thr  Pro  Gly  Pro  Gln  Gly  Leu  Pro  Gly  Ser  Pro  Gly  Ala
                           20                       25                      30

Pro  Gly  Thr  Pro  Gly  Pro  Gln  Gly  Leu  Pro  Gly  Ser  Pro  Gly  Ala  Pro
                      35                       40                      45

Gly  Thr  Pro  Gly  Glu  Gly  Gln  Gln  His  His  Leu  Gly  Gly  Ala  Arg  Gln
                      50                       55                      60

Ala  Gly  Asp  Val  Gly  Ser  Pro
            65                       70

( 2 ) INFORMATION FOR SEQ ID NO:116:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "synthetic"

( x i ) SEQUENCE DESCRIPTION: SEQ ID NO:116:

GTGGAGCTCG CCAGGCAGGC GACGT                                                                              25

( 2 ) INFORMATION FOR SEQ ID NO:117:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "synthetic"

( x i ) SEQUENCE DESCRIPTION: SEQ ID NO:117:

CGCCTGCCTG GCGAGCTCCA CGAAG 25

(2) INFORMATION FOR SEQ ID NO:118:

(i) SEQUENCE CHARACTERISTICS:
　　　　(A) LENGTH: 219 base pairs
　　　　(B) TYPE: nucleic acid
　　　　(C) STRANDEDNESS: double
　　　　(D) TOPOLOGY: linear (ii) MOLECULE TYPE: other nucleic acid
　　　　(A) DESCRIPTION: /desc = "synthetic"

(xi) SEQUENCE DESCRIPTION: SEQ ID NO:118:

GGTGCCCCGG GTACTCCTGG TCCACAAGGT CTGCCGGGAA GCCCAGGGGC TCCGGGTACT 60

CCAGGTCCGC AAGGCCTGCC GGGTTCACCG GGTGCTCCGG GAACTCCTGG CCCGCAGGGC 120

TTGCCGGGAT CCCCAGGTGC ACCAGGAACG CCGGGAGAAG GTCAACAGCA CCATCTTGGT 180

GGAGCTCGCC AGGCAGGCGA CGTCGGTAGC CCTGGTGCC 219

(2) INFORMATION FOR SEQ ID NO:119:

(i) SEQUENCE CHARACTERISTICS:
　　　　(A) LENGTH: 73 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:119:

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Glu Gly Gln Gln His His Leu Gly Gly Ala Arg Gln
    50                  55                  60

Ala Gly Asp Val Gly Ser Pro Gly Ala
65                  70

(2) INFORMATION FOR SEQ ID NO:120:

(i) SEQUENCE CHARACTERISTICS:
　　　　(A) LENGTH: 762 amino acids
　　　　(B) TYPE: amino acid
　　　　(C) STRANDEDNESS: single
　　　　(D) TOPOLOGY: linear (ii) MOLECULE TYPE: protein (xi) SEQUENCE DESCRIPTION: SEQ ID NO:120:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Pro Gly Thr Pro Gly Pro Gln Gly Leu Pro Gly Ser Pro
            35                  40                  45

Gly Ala Pro Gly Thr Pro Gly Pro Gln Gly Leu Pro Gly Ser Pro Gly
        50                  55                  60

Ala Pro Gly Thr Pro Gly Pro Gln Gly Leu Pro Gly Ser Pro Gly Ala
65                  70                  75                  80

```
Pro Gly Thr Pro Gly Glu Gly Gln Gln His His Leu Gly Gly Ala Arg
                85                      90                      95
Gln Ala Gly Asp Val Gly Ser Pro Gly Ala Pro Gly Thr Pro Gly Pro
            100             105                     110
Gln Gly Leu Pro Gly Ser Pro Gly Ala Pro Gly Thr Pro Gly Pro Gln
            115             120                     125
Gly Leu Pro Gly Ser Pro Gly Ala Pro Gly Thr Pro Gly Pro Gln Gly
    130             135                     140
Leu Pro Gly Ser Pro Gly Ala Pro Gly Thr Pro Gly Glu Gly Gln Gln
145             150                     155                 160
His His Leu Gly Gly Ala Arg Gln Ala Gly Asp Val Gly Ser Pro Gly
            165                     170                 175
Ala Pro Gly Thr Pro Gly Pro Gln Gly Leu Pro Gly Ser Pro Gly Ala
            180                     185                 190
Pro Gly Thr Pro Gly Pro Gln Gly Leu Pro Gly Ser Pro Gly Ala Pro
            195             200                 205
Gly Thr Pro Gly Pro Gln Gly Leu Pro Gly Ser Pro Gly Ala Pro Gly
    210                 215                 220
Thr Pro Gly Glu Gly Gln Gln His His Leu Gly Gly Ala Arg Gln Ala
225             230                 235                     240
Gly Asp Val Gly Ser Pro Gly Ala Pro Gly Thr Pro Gly Pro Gln Gly
            245                     250                 255
Leu Pro Gly Ser Pro Gly Ala Pro Gly Thr Pro Gly Pro Gln Gly Leu
            260                     265                 270
Pro Gly Ser Pro Gly Ala Pro Gly Thr Pro Gly Pro Gln Gly Leu Pro
        275                     280                 285
Gly Ser Pro Gly Ala Pro Gly Thr Pro Gly Glu Gly Gln Gln His His
    290                     295                 300
Leu Gly Gly Ala Arg Gln Ala Gly Asp Val Gly Ser Pro Gly Ala Pro
305                     310                 315                 320
Gly Thr Pro Gly Pro Gln Gly Leu Pro Gly Ser Pro Gly Ala Pro Gly
            325                     330                 335
Thr Pro Gly Pro Gln Gly Leu Pro Gly Ser Pro Gly Ala Pro Gly Thr
            340                     345                 350
Pro Gly Pro Gln Gly Leu Pro Gly Ser Pro Gly Ala Pro Gly Thr Pro
        355                     360                 365
Gly Glu Gly Gln Gln His His Leu Gly Gly Ala Arg Gln Ala Gly Asp
    370                 375                     380
Val Gly Ser Pro Gly Ala Pro Gly Thr Pro Gly Pro Gln Gly Leu Pro
385                 390                     395                 400
Gly Ser Pro Gly Ala Pro Gly Thr Pro Gly Pro Gln Gly Leu Pro Gly
            405                     410                 415
Ser Pro Gly Ala Pro Gly Thr Pro Gly Pro Gln Gly Leu Pro Gly Ser
            420                     425                 430
Pro Gly Ala Pro Gly Thr Pro Gly Glu Gly Gln Gln His His Leu Gly
        435                     440                 445
Gly Ala Arg Gln Ala Gly Asp Val Gly Ser Pro Gly Ala Pro Gly Thr
        450                     455                 460
Pro Gly Pro Gln Gly Leu Pro Gly Ser Pro Gly Ala Pro Gly Thr Pro
465                 470                     475                 480
Gly Pro Gln Gly Leu Pro Gly Ser Pro Gly Ala Pro Gly Thr Pro Gly
                485                     490                 495
Pro Gln Gly Leu Pro Gly Ser Pro Gly Ala Pro Gly Thr Pro Gly Glu
            500                     505                 510
```

```
Gly  Gln  Gln  His  His  Leu  Gly  Gly  Ala  Arg  Gln  Ala  Gly  Asp  Val  Gly
          515                 520                      525

Ser  Pro  Gly  Ala  Pro  Gly  Thr  Pro  Gly  Pro  Gln  Gly  Leu  Pro  Gly  Ser
     530                 535                      540

Pro  Gly  Ala  Pro  Gly  Thr  Pro  Gly  Pro  Gln  Gly  Leu  Pro  Gly  Ser  Pro
545                      550                      555                      560

Gly  Ala  Pro  Gly  Thr  Pro  Gly  Pro  Gln  Gly  Leu  Pro  Gly  Ser  Pro  Gly
               565                           570                 575

Ala  Pro  Gly  Thr  Pro  Gly  Glu  Gly  Gln  Gln  His  His  Leu  Gly  Gly  Ala
               580                 585                           590

Arg  Gln  Ala  Gly  Asp  Val  Gly  Ser  Pro  Gly  Ala  Pro  Gly  Thr  Pro  Gly
          595                      600                      605

Pro  Gln  Gly  Leu  Pro  Gly  Ser  Pro  Gly  Ala  Pro  Gly  Thr  Pro  Gly  Pro
     610                      615                      620

Gln  Gly  Leu  Pro  Gly  Ser  Pro  Gly  Ala  Pro  Gly  Thr  Pro  Gly  Pro  Gln
625                      630                      635                      640

Gly  Leu  Pro  Gly  Ser  Pro  Gly  Ala  Pro  Gly  Thr  Pro  Gly  Glu  Gly  Gln
                    645                      650                      655

Gln  His  His  Leu  Gly  Gly  Ala  Arg  Gln  Ala  Gly  Asp  Val  Gly  Ser  Pro
               660                      665                      670

Gly  Ala  Pro  Gly  Thr  Pro  Gly  Pro  Gln  Gly  Leu  Pro  Gly  Ser  Pro  Gly
          675                      680                      685

Ala  Pro  Gly  Thr  Pro  Gly  Pro  Gln  Gly  Leu  Pro  Gly  Ser  Pro  Gly  Ala
     690                      695                      700

Pro  Gly  Thr  Pro  Gly  Pro  Gln  Gly  Leu  Pro  Gly  Ser  Pro  Gly  Ala  Pro
705                      710                      715                      720

Gly  Thr  Pro  Gly  Glu  Gly  Gln  Gln  His  His  Leu  Gly  Gly  Ala  Arg  Gln
                    725                      730                      735

Ala  Gly  Asp  Val  Gly  Ser  Pro  Gly  Ala  Met  Asp  Pro  Gly  Arg  Tyr  Gln
               740                      745                      750

Asp  Leu  Arg  Ser  His  His  His  His  His  His
          755                 760
```

( 2 ) INFORMATION FOR SEQ ID NO:121:

( i ) SEQUENCE CHARACTERISTICS:
( A ) LENGTH: 63 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:121:

```
Gly  Ala  Pro  Gly  Thr  Pro  Gly  Pro  Gln  Gly  Leu  Pro  Gly  Ser  Pro  Gly
1                   5                   10                      15

Ala  Pro  Gly  Thr  Pro  Gly  Pro  Gln  Gly  Leu  Pro  Gly  Ser  Pro  Gly  Ala
               20                      25                      30

Pro  Gly  Thr  Pro  Gly  Pro  Gln  Gly  Leu  Pro  Gly  Ser  Pro  Gly  Ala  Pro
          35                      40                      45

Gly  Thr  Pro  Gly  Gly  Ala  Lys  Gln  Ala  Gly  Asp  Val  Gly  Ser  Pro
     50                      55                      60
```

( 2 ) INFORMATION FOR SEQ ID NO:122:

( i ) SEQUENCE CHARACTERISTICS:
( A ) LENGTH: 61 base pairs
( B ) TYPE: nucleic acid (C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:122:

```
TGCACCAGGA ACGCCGGGAG GTGCTAAACA AGCAGGAGAC GTCGGTAGCC CTGGTGCCTT    60
T                                                                    61
```

(2) INFORMATION FOR SEQ ID NO:123:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:123:

```
AAAGGCACCA GGGCTACCGA CGTCTCCTGC TTGTTTAGCA CCTCCCGGCG TTCCTGG       57
```

(2) INFORMATION FOR SEQ ID NO:124:

(i) SEQUENCE CHARACTERISTICS:
(A) LENGTH: 195 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic"

(xi) SEQUENCE DESCRIPTION: SEQ ID NO:124:

```
GGTGCCCCGG GTACTCCTGG TCCACAAGGT CTGCCGGGAA GCCCAGGGGC TCCGGGTACT    60
CCAGGTCCGC AAGGCCTGCC GGGTTCACCG GGTGCTCCGG GAACTCCTGG CCCGCAGGGC    120
TTGCCGGGAT CCCCAGGTGC ACCAGGAACG CCGGGAGGTG CTAAACAAGC AGGAGACGTC    180
GGTAGCCCTG GTGCC                                                     195
```

(2) INFORMATION FOR SEQ ID NO:125:

(i) SEQUENCE CHARACTERISTICS:
(A) LENGTH: 65 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:125:

```
Gly Ala Pro Gly Thr Pro Gly Pro Gln Gly Leu Pro Gly Ser Pro Gly
 1               5                  10                  15
Ala Pro Gly Thr Pro Gly Pro Gln Gly Leu Pro Gly Ser Pro Gly Ala
                20                  25                  30
Pro Gly Thr Pro Gly Pro Gln Gly Leu Pro Gly Ser Pro Gly Ala Pro
            35                  40                  45
Gly Thr Pro Gly Gly Ala Lys Gln Ala Gly Asp Val Gly Ser Pro Gly
        50                  55                  60
Ala
65
```

(2) INFORMATION FOR SEQ ID NO:126:

(i) SEQUENCE CHARACTERISTICS:
        (A) LENGTH: 682 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:126:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
            20                  25                  30
Met Gly Ala Pro Gly Thr Pro Gly Pro Gln Gly Leu Pro Gly Ser Pro
        35                  40                  45
Gly Ala Pro Gly Thr Pro Gly Pro Gln Gly Leu Pro Gly Ser Pro Gly
    50                  55                  60
Ala Pro Gly Thr Pro Gly Pro Gln Gly Leu Pro Gly Ser Pro Gly Ala
65                  70                  75                  80
Pro Gly Thr Pro Gly Gly Ala Lys Gln Ala Gly Asp Val Gly Ser Pro
                85                  90                  95
Gly Ala Pro Gly Thr Pro Gly Pro Gln Gly Leu Pro Gly Ser Pro Gly
            100                 105                 110
Ala Pro Gly Thr Pro Gly Pro Gln Gly Leu Pro Gly Ser Pro Gly Ala
        115                 120                 125
Pro Gly Thr Pro Gly Pro Gln Gly Leu Pro Gly Ser Pro Gly Ala Pro
    130                 135                 140
Gly Thr Pro Gly Gly Ala Lys Gln Ala Gly Asp Val Gly Ser Pro Gly
145                 150                 155                 160
Ala Pro Gly Thr Pro Gly Pro Gln Gly Leu Pro Gly Ser Pro Gly Ala
                165                 170                 175
Pro Gly Thr Pro Gly Pro Gln Gly Leu Pro Gly Ser Pro Gly Ala Pro
            180                 185                 190
Gly Thr Pro Gly Pro Gln Gly Leu Pro Gly Ser Pro Gly Ala Pro Gly
        195                 200                 205
Thr Pro Gly Gly Ala Lys Gln Ala Gly Asp Val Gly Ser Pro Gly Ala
    210                 215                 220
Pro Gly Thr Pro Gly Pro Gln Gly Leu Pro Gly Ser Pro Gly Ala Pro
225                 230                 235                 240
Gly Thr Pro Gly Pro Gln Gly Leu Pro Gly Ser Pro Gly Ala Pro Gly
                245                 250                 255
Thr Pro Gly Pro Gln Gly Leu Pro Gly Ser Pro Gly Ala Pro Gly Thr
            260                 265                 270
Pro Gly Gly Ala Lys Gln Ala Gly Asp Val Gly Ser Pro Gly Ala Pro
        275                 280                 285
Gly Thr Pro Gly Pro Gln Gly Leu Pro Gly Ser Pro Gly Ala Pro Gly
    290                 295                 300
Thr Pro Gly Pro Gln Gly Leu Pro Gly Ser Pro Gly Ala Pro Gly Thr
305                 310                 315                 320
Pro Gly Pro Gln Gly Leu Pro Gly Ser Pro Gly Ala Pro Gly Thr Pro
                325                 330                 335
Gly Gly Ala Lys Gln Ala Gly Asp Val Gly Ser Pro Gly Ala Pro Gly
            340                 345                 350
Thr Pro Gly Pro Gln Gly Leu Pro Gly Ser Pro Gly Ala Pro Gly Thr
        355                 360                 365
```

```
Pro Gly Pro Gln Gly Leu Pro Gly Ser Pro Gly Ala Pro Gly Thr Pro
    370             375             380

Gly Pro Gln Gly Leu Pro Gly Ser Pro Gly Ala Pro Gly Thr Pro Gly
385             390             395                         400

Gly Ala Lys Gln Ala Gly Asp Val Gly Ser Pro Gly Ala Pro Gly Thr
            405             410                         415

Pro Gly Pro Gln Gly Leu Pro Gly Ser Pro Gly Ala Pro Gly Thr Pro
            420             425             430

Gly Pro Gln Gly Leu Pro Gly Ser Pro Gly Ala Pro Gly Thr Pro Gly
        435             440             445

Pro Gln Gly Leu Pro Gly Ser Pro Gly Ala Pro Gly Thr Pro Gly Gly
    450             455             460

Ala Lys Gln Ala Gly Asp Val Gly Ser Pro Gly Ala Pro Gly Thr Pro
465             470             475                         480

Gly Pro Gln Gly Leu Pro Gly Ser Pro Gly Ala Pro Gly Thr Pro Gly
            485             490             495

Pro Gln Gly Leu Pro Gly Ser Pro Gly Ala Pro Gly Thr Pro Gly Pro
        500             505             510

Gln Gly Leu Pro Gly Ser Pro Gly Ala Pro Gly Thr Pro Gly Gly Ala
    515             520             525

Lys Gln Ala Gly Asp Val Gly Ser Pro Gly Ala Pro Gly Thr Pro Gly
    530             535             540

Pro Gln Gly Leu Pro Gly Ser Pro Gly Ala Pro Gly Thr Pro Gly Pro
545             550             555                         560

Gln Gly Leu Pro Gly Ser Pro Gly Ala Pro Gly Thr Pro Gly Pro Gln
            565             570             575

Gly Leu Pro Gly Ser Pro Gly Ala Pro Gly Thr Pro Gly Gly Ala Lys
        580             585             590

Gln Ala Gly Asp Val Gly Ser Pro Gly Ala Pro Gly Thr Pro Gly Pro
        595             600             605

Gln Gly Leu Pro Gly Ser Pro Gly Ala Pro Gly Thr Pro Gly Pro Gln
    610             615             620

Gly Leu Pro Gly Ser Pro Gly Ala Pro Gly Thr Pro Gly Pro Gln Gly
625             630             635                         640

Leu Pro Gly Ser Pro Gly Ala Pro Gly Thr Pro Gly Gly Ala Lys Gln
            645             650                         655

Ala Gly Asp Val Gly Ser Pro Gly Ala Met Asp Pro Gly Arg Tyr Gln
            660             665                         670

Asp Leu Arg Ser His His His His His
        675             680
```

( 2 ) INFORMATION FOR SEQ ID NO:127:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:127:

```
Gly Ala Pro Gly Thr Pro Gly Pro Gln Gly Leu Pro Gly Ser Pro Gly
1               5               10              15

Ala Pro Gly Thr Pro Gly Pro Gln Gly Leu Pro Gly Ser Pro Gly Ala
        20              25              30
```

|   |   |   |   |   |   |   |   |   |   |   |   |   |   |   |
|---|---|---|---|---|---|---|---|---|---|---|---|---|---|---|
| Thr | Arg | Trp<br>35 | Tyr | Ser | Met | Lys | Lys<br>40 | Thr | Thr | Met | Lys | Ile<br>45 | Ile | Pro | Phe |
| Asn | Arg<br>50 | Leu | Thr | Ile | Gly | Glu<br>55 | Gly | Gln | Gln | His | His<br>60 | Leu | Gly | Gly | Ala |
| Arg<br>65 | Gln | Ala | Gly | Asp | Val<br>70 | Gly | Ser | Pro |

( 2 ) INFORMATION FOR SEQ ID NO:128:

( i ) SEQUENCE CHARACTERISTICS:
      ( A ) LENGTH: 126 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic"

( x i ) SEQUENCE DESCRIPTION: SEQ ID NO:128:

| | | | | | |
|---|---|---|---|---|---|
| ATGGCAGCGA | AAGGGGACCA | CCGGGTGCTA | CCCGTTGGTA | TTCTATGAAA | AAGACTACCA | 60 |
| TGAAAATCAT | TCCGTTTAAC | CGCCTGACCA | TTGGCGAAGG | TCAACTTTCC | GCTAAAGTCC | 120 |
| TGCCGT | | | | | | 126 |

( 2 ) INFORMATION FOR SEQ ID NO:129:

( i ) SEQUENCE CHARACTERISTICS:
      ( A ) LENGTH: 225 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "synthetic"

( x i ) SEQUENCE DESCRIPTION: SEQ ID NO:129:

| | | | | | |
|---|---|---|---|---|---|
| GGTGCCCCGG | GTACTCCTGG | TCCACAAGGT | CTGCCGGGAA | GCCCAGGGGC | TCCGGGTACT | 60 |
| CCAGGTCCGC | AAGGCCTGCC | GGGTTCACCG | GGTGCTACCC | GTTGGTATTC | TATGAAAAAG | 120 |
| ACTACCATGA | AAATCATTCC | GTTTAACCGC | CTGACCATTG | GCGAAGGTCA | ACAGCACCAT | 180 |
| CTTGGTGGAG | CTCGCCAGGC | AGGCGACGTC | GGTAGCCCTG | GTGCC | | 225 |

( 2 ) INFORMATION FOR SEQ ID NO:130:

( i ) SEQUENCE CHARACTERISTICS:
      ( A ) LENGTH: 75 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:130:

|   |   |   |   |   |   |   |   |   |   |   |   |   |   |   |   |
|---|---|---|---|---|---|---|---|---|---|---|---|---|---|---|---|
| Gly<br>1 | Ala | Pro | Gly | Thr<br>5 | Pro | Gly | Pro | Gln | Gly<br>10 | Leu | Pro | Gly | Ser | Pro<br>15 | Gly |
| Ala | Pro | Gly | Thr<br>20 | Pro | Gly | Pro | Gln<br>25 | Gly | Leu | Pro | Gly | Ser<br>30 | Pro | Gly | Ala |
| Thr | Arg | Trp<br>35 | Tyr | Ser | Met | Lys | Lys<br>40 | Thr | Thr | Met | Lys | Ile<br>45 | Ile | Pro | Phe |
| Asn | Arg<br>50 | Leu | Thr | Ile | Gly | Glu<br>55 | Gly | Gln | Gln | His | His<br>60 | Leu | Gly | Gly | Ala |
| Arg<br>65 | Gln | Ala | Gly | Asp | Val<br>70 | Gly | Ser | Pro | Gly | Ala<br>75 |

( 2 ) INFORMATION FOR SEQ ID NO:131:

( i ) SEQUENCE CHARACTERISTICS:
      ( A ) LENGTH: 198 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:131:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Pro Gly Thr Pro Gly Pro Gln Gly Leu Pro Gly Ser Pro
        35                  40                  45

Gly Ala Pro Gly Thr Pro Gly Pro Gln Gly Leu Pro Gly Ser Pro Gly
    50                  55                  60

Ala Thr Arg Trp Tyr Ser Met Lys Lys Thr Thr Met Lys Ile Ile Pro
65                  70                  75                  80

Phe Asn Arg Leu Thr Ile Gly Glu Gly Gln Gln His His Leu Gly Gly
                85                  90                  95

Ala Arg Gln Ala Gly Asp Val Gly Ser Pro Gly Ala Pro Gly Thr Pro
                100                 105                 110

Gly Pro Gln Gly Leu Pro Gly Ser Pro Gly Ala Pro Gly Thr Pro Gly
            115                 120                 125

Pro Gln Gly Leu Pro Gly Ser Pro Gly Ala Thr Arg Trp Tyr Ser Met
            130                 135                 140

Lys Lys Thr Thr Met Lys Ile Ile Pro Phe Asn Arg Leu Thr Ile Gly
145                 150                 155                 160

Glu Gly Gln Gln His His Leu Gly Gly Ala Arg Gln Ala Gly Asp Val
                165                 170                 175

Gly Ser Pro Gly Ala Met Asp Pro Gly Arg Tyr Gln Asp Leu Arg Ser
            180                 185                 190

His His His His His His
            195
```

( 2 ) INFORMATION FOR SEQ ID NO:132:

( i ) SEQUENCE CHARACTERISTICS:
      ( A ) LENGTH: 829 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:132:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Ala
            20                  25                  30

Pro Gly Thr Pro Gly Glu Gly Gln Gln His His Leu Gly Gly Ala Lys
        35                  40                  45

Gln Ala Gly Asp Val Gly Ser Pro Gly Ala Pro Gly Thr Pro Gly Pro
    50                  55                  60

Gln Gly Leu Pro Gly Ser Pro Gly Ala Pro Gly Thr Pro Gly Pro Gln
65                  70                  75                  80

Gly Leu Pro Gly Ser Pro Gly Ala Pro Gly Thr Pro Gly Pro Gln Gly
```

|     |     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- | --- |
| Leu | Pro | Gly | Ser | Pro | Gly | Ala | Pro | Gly | Thr | Pro | Gly | Pro | Gln | Gly | Leu |
|     |     |     | 100 |     |     |     |     | 105 |     |     |     |     | 110 |     |     |
| Pro | Gly | Ser | Pro | Gly | Ala | Pro | Gly | Thr | Pro | Gly | Pro | Gln | Gly | Leu | Pro |
|     |     | 115 |     |     |     |     | 120 |     |     |     |     | 125 |     |     |     |
| Gly | Ser | Pro | Gly | Ala | Pro | Gly | Thr | Pro | Gly | Pro | Gln | Gly | Leu | Pro | Gly |
|     | 130 |     |     |     |     | 135 |     |     |     |     | 140 |     |     |     |     |
| Ser | Pro | Gly | Ala | Pro | Gly | Thr | Pro | Gly | Pro | Gln | Gly | Leu | Pro | Gly | Ser |
| 145 |     |     |     |     | 150 |     |     |     |     | 155 |     |     |     |     | 160 |
| Pro | Gly | Ala | Pro | Gly | Thr | Pro | Gly | Pro | Gln | Gly | Leu | Pro | Gly | Ser | Pro |
|     |     |     |     | 165 |     |     |     |     | 170 |     |     |     |     | 175 |     |
| Gly | Ala | Pro | Gly | Thr | Pro | Gly | Pro | Gln | Gly | Leu | Pro | Gly | Ser | Pro | Gly |
|     |     |     | 180 |     |     |     |     | 185 |     |     |     |     | 190 |     |     |
| Ala | Pro | Gly | Thr | Pro | Gly | Pro | Gln | Gly | Leu | Pro | Gly | Ser | Pro | Gly | Ala |
|     |     | 195 |     |     |     |     | 200 |     |     |     |     | 205 |     |     |     |
| Pro | Gly | Thr | Pro | Gly | Pro | Gln | Gly | Leu | Pro | Gly | Ser | Pro | Gly | Ala | Pro |
|     | 210 |     |     |     |     | 215 |     |     |     |     | 220 |     |     |     |     |
| Gly | Thr | Pro | Gly | Pro | Gln | Gly | Leu | Pro | Gly | Ser | Pro | Gly | Ala | Pro | Gly |
| 225 |     |     |     |     | 230 |     |     |     |     | 235 |     |     |     |     | 240 |
| Thr | Pro | Gly | Pro | Gln | Gly | Leu | Pro | Gly | Ser | Pro | Gly | Ala | Pro | Gly | Thr |
|     |     |     |     | 245 |     |     |     |     | 250 |     |     |     |     | 255 |     |
| Pro | Gly | Pro | Gln | Gly | Leu | Pro | Gly | Ser | Pro | Gly | Ala | Pro | Gly | Thr | Pro |
|     |     |     | 260 |     |     |     |     | 265 |     |     |     |     | 270 |     |     |
| Gly | Pro | Gln | Gly | Leu | Pro | Gly | Ser | Pro | Gly | Ala | Pro | Gly | Thr | Pro | Gly |
|     |     | 275 |     |     |     |     | 280 |     |     |     |     | 285 |     |     |     |
| Pro | Gln | Gly | Leu | Pro | Gly | Ser | Pro | Gly | Ala | Pro | Gly | Thr | Pro | Gly | Pro |
|     | 290 |     |     |     |     | 295 |     |     |     |     | 300 |     |     |     |     |
| Gln | Gly | Leu | Pro | Gly | Ser | Pro | Gly | Ala | Pro | Gly | Thr | Pro | Gly | Pro | Gln |
| 305 |     |     |     |     | 310 |     |     |     |     | 315 |     |     |     |     | 320 |
| Gly | Leu | Pro | Gly | Ser | Pro | Gly | Ala | Pro | Gly | Thr | Pro | Gly | Pro | Gln | Gly |
|     |     |     |     | 325 |     |     |     |     | 330 |     |     |     |     | 335 |     |
| Leu | Pro | Gly | Ser | Pro | Gly | Ala | Pro | Gly | Thr | Pro | Gly | Pro | Gln | Gly | Leu |
|     |     |     | 340 |     |     |     |     | 345 |     |     |     |     | 350 |     |     |
| Pro | Gly | Ser | Pro | Gly | Ala | Pro | Gly | Thr | Pro | Gly | Pro | Gln | Gly | Leu | Pro |
|     |     | 355 |     |     |     |     | 360 |     |     |     |     | 365 |     |     |     |
| Gly | Ser | Pro | Gly | Ala | Pro | Gly | Thr | Pro | Gly | Pro | Gln | Gly | Leu | Pro | Gly |
|     | 370 |     |     |     |     | 375 |     |     |     |     | 380 |     |     |     |     |
| Ser | Pro | Gly | Ala | Pro | Gly | Thr | Pro | Gly | Pro | Gln | Gly | Leu | Pro | Gly | Ser |
| 385 |     |     |     |     | 390 |     |     |     |     | 395 |     |     |     |     | 400 |
| Pro | Gly | Ala | Pro | Gly | Thr | Pro | Gly | Pro | Gln | Gly | Leu | Pro | Gly | Ser | Pro |
|     |     |     |     | 405 |     |     |     |     | 410 |     |     |     |     | 415 |     |
| Gly | Ala | Pro | Gly | Thr | Pro | Gly | Pro | Gln | Gly | Leu | Pro | Gly | Ser | Pro | Gly |
|     |     |     | 420 |     |     |     |     | 425 |     |     |     |     | 430 |     |     |
| Ala | Pro | Gly | Thr | Pro | Gly | Pro | Gln | Gly | Leu | Pro | Gly | Ser | Pro | Gly | Ala |
|     |     | 435 |     |     |     |     | 440 |     |     |     |     | 445 |     |     |     |
| Pro | Gly | Thr | Pro | Gly | Pro | Gln | Gly | Leu | Pro | Gly | Ser | Pro | Gly | Ala | Pro |
|     | 450 |     |     |     |     | 455 |     |     |     |     | 460 |     |     |     |     |
| Gly | Thr | Pro | Gly | Pro | Gln | Gly | Leu | Pro | Gly | Ser | Pro | Gly | Ala | Pro | Gly |
| 465 |     |     |     |     | 470 |     |     |     |     | 475 |     |     |     |     | 480 |
| Thr | Pro | Gly | Pro | Gln | Gly | Leu | Pro | Gly | Ser | Pro | Gly | Ala | Pro | Gly | Thr |
|     |     |     |     | 485 |     |     |     |     | 490 |     |     |     |     | 495 |     |
| Pro | Gly | Pro | Gln | Gly | Leu | Pro | Gly | Ser | Pro | Gly | Ala | Pro | Gly | Thr | Pro |
|     |     |     | 500 |     |     |     |     | 505 |     |     |     |     | 510 |     |     |

```
Gly  Pro  Gln  Gly  Leu  Pro  Gly  Ser  Pro  Gly  Ala  Pro  Gly  Thr  Pro  Gly
          515                      520                     525

Pro  Gln  Gly  Leu  Pro  Gly  Ser  Pro  Gly  Ala  Pro  Gly  Thr  Pro  Gly  Pro
     530                      535                     540

Gln  Gly  Leu  Pro  Gly  Ser  Pro  Gly  Ala  Pro  Gly  Thr  Pro  Gly  Pro  Gln
545                      550                     555                          560

Gly  Leu  Pro  Gly  Ser  Pro  Gly  Ala  Pro  Gly  Thr  Pro  Gly  Pro  Gln  Gly
               565                      570                     575

Leu  Pro  Gly  Ser  Pro  Gly  Ala  Pro  Gly  Thr  Pro  Gly  Pro  Gln  Gly  Leu
               580                      585                     590

Pro  Gly  Ser  Pro  Gly  Ala  Pro  Gly  Thr  Pro  Gly  Pro  Gln  Gly  Leu  Pro
          595                      600                     605

Gly  Ser  Pro  Gly  Ala  Pro  Gly  Thr  Pro  Gly  Pro  Gln  Gly  Leu  Pro  Gly
          610                      615                     620

Ser  Pro  Gly  Ala  Pro  Gly  Thr  Pro  Gly  Pro  Gln  Gly  Leu  Pro  Gly  Ser
625                      630                     635                          640

Pro  Gly  Ala  Pro  Gly  Thr  Pro  Gly  Pro  Gln  Gly  Leu  Pro  Gly  Ser  Pro
                    645                     650                     655

Gly  Ala  Pro  Gly  Thr  Pro  Gly  Pro  Gln  Gly  Leu  Pro  Gly  Ser  Pro  Gly
               660                     665                     670

Ala  Pro  Gly  Thr  Pro  Gly  Pro  Gln  Gly  Leu  Pro  Gly  Ser  Pro  Gly  Ala
          675                     680                     685

Pro  Gly  Thr  Pro  Gly  Pro  Gln  Gly  Leu  Pro  Gly  Ser  Pro  Gly  Ala  Pro
          690                     695                     700

Gly  Thr  Pro  Gly  Pro  Gln  Gly  Leu  Pro  Gly  Ser  Pro  Gly  Ala  Pro  Gly
705                     710                     715                          720

Thr  Pro  Gly  Pro  Gln  Gly  Leu  Pro  Gly  Ser  Pro  Gly  Ala  Pro  Gly  Thr
                    725                     730                     735

Pro  Gly  Pro  Gln  Gly  Leu  Pro  Gly  Ser  Pro  Gly  Ala  Pro  Gly  Thr  Pro
               740                     745                     750

Gly  Pro  Gln  Gly  Leu  Pro  Gly  Ser  Pro  Gly  Ala  Pro  Gly  Thr  Pro  Gly
          755                     760                     765

Pro  Gln  Gly  Leu  Pro  Gly  Ser  Pro  Gly  Ala  Met  Asp  Pro  Gly  Arg  Tyr
     770                     775                     780

His  Met  Ala  Ala  Lys  Gly  Asp  Arg  Ala  Pro  Gly  Thr  Pro  Gly  Glu  Gly
785                      790                     795                          800

Gln  Gln  His  His  Leu  Gly  Gly  Ala  Lys  Gln  Ala  Gly  Asp  Val  Gly  Ser
                    805                     810                     815

Pro  Asp  Gln  Asp  Leu  Arg  Ser  His  His  His  His  His  His
               820                     825
```

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:133:

```
Gly  Ala  Pro  Gly  Pro  Ala  Gly  Pro  Pro
1                    5
```

(2) INFORMATION FOR SEQ ID NO:134:

(i) SEQUENCE CHARACTERISTICS:

-continued

```
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:134:

Gly  Ala  Pro  Gly  Pro  Ala  Gly  Pro  Pro  Gly  Ser  Arg  Gly  Asp  Pro  Gly
 1                    5                        10                        15

Pro  Pro (2) INFORMATION FOR SEQ ID NO:135:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:135:

Gly  Ala  Gln  Gly  Pro  Ala  Gly  Pro  Gly  Gly  Ser  Arg  Gly  Asp  Pro  Gly
 1                    5                        10                        15

Pro  Pro
```

HIGH MOLECULAR WEIGHT COLLAGEN-LIKE PROTEIN POLYMERS

CROSS-REFERENCE TO RELATED APPLICATIONS

This application is a continuation-in-part of application Ser. No. 08/577,046, filed Dec. 22, 1995, which application is a continuation of 07/972,032 filed Nov. 5, 1992, now U.S. Pat. No. 5,496,712 issued Mar. 5, 1996, which application is a continuation-in-part of application Ser. No. 07/791,960, filed Nov. 12, 1991, now abandoned, which application is a continuation-in-part of application Ser. No. 07/609,716, filed Nov. 6, 1990, now U.S. Pat. No. 5,514,581 issued May 7, 1996, which application is a continuation-in-part of application Ser. No. 07/269,429, filed Nov. 9, 1988, now abandoned, which application is a continuation-in-part of application Ser. No. 07/114,618, filed Oct. 29, 1987, now U.S. Pat. No. 5,243,038 issued Sep. 7, 1993, which application is a continuation-in-part of application Ser. No. 06/927,258, filed Nov. 4, 1986, now abandoned.

TECHNICAL FIELD

The field of this invention is the production of collagen-like polymers using recombinant techniques.

BACKGROUND

Collagen, a naturally occurring protein, finds wide application in industry. Chemically hydrolyzed natural collagen can be denatured and renatured by heating and cooling to produce gelatin, which is used in photographic and medical applications, among other applications. The chain property of collagen responsible for this phenomenon is its ability to spontaneously form interchain aggregates having a conformation designated as a triple helix. The helices are stabilized by weak interactions between chains, arising from the close proximity of the peptide backbone at locations every third residue occupied by glycine and kinks provided by proline and hydroxyproline at the two positions between glycine. The geometry of the three kinked chains allows for hydrogen bonding within the triple helix. The structure is loose and is readily accessible to interaction with water, small organic and inorganic molecules, other proteins, and cells. Although collagen consists of many different amino acid sequences, one of the more structurally stable segments exists at the amino and carboxyl terminal ends of the processed collagen Type I chains. These ends consist to a large degree of the repeating tripeptide sequence GPP (the second P is often hydroxylated).

With the advent of recombinant technology, the opportunity arose to produce collagen-like polymers, where the advantageous properties of collagen could be selectively retained, while new capabilities and characteristics could be introduced. By contrast with natural forms of collagen, recombinantly-produced collagen-like polymers may consist exclusively of a single repeating tripeptide sequence selected from a wide variety of GXY sequences, where X and Y can be any amino acid, whether derived from known natural sequences or not. Recombinant collagen-like polymers can also consist of different tripeptide sequences, which are repeated as blocks in the final polymer. Dissimilar blocks can also be used in a repeating fashion to create block copolymers in order to provide additional chemical or biological functionality.

The uniqueness of collagen, the repetitive tripeptide, is a challenge for recombinant technology in light of the high repetitiveness of the sequence and the frequent utility of the amino acids glycine and proline in the composition. Genes encoding proteins with high levels of glycine and proline are by necessity composed of high levels of the nucleotides guanidine and cytidine in self complementary sequences. Thus, as one synthesizes the gene, there is substantial opportunity for strands to loop out, single-stranded DNA to be excised, recombination events to occur which can result in loss of segments of the gene, and inefficient transcription and/or translation. Thus, there is substantial interest in developing techniques and compositions which provide the advantageous properties of collagen, while at the same time allow for stable expression of high molecular weight collagen-like proteins of at least about 30 kDal.

Relevant Literature

WO 88/05082 and Goldberg, et al. Gene (Amst.) 80:305-314 (1989) describe the preparation of relatively low molecular weight collagen analog proteins. See also PCT/US87/03360 and PCT[US 89/05016 which describe structural protein polymers.

SUMMARY OF THE INVENTION

High molecular weight, unnatural collagen-like polymers are provided wherein a major proportion of the amino acids of the polymers are present as triads having glycine as the first amino acid, where at least 40 number % of the triads comprise at least one proline and the total proline content of the triads, usually the entire polymer, is less than 45 number %. Also provided are genes encoding the subject polymers. The genes are prepared by synthesizing sequences having a plurality of tripeptide units, ligating the sequences together to provide multimers, cloning the multimers, and finally joining the multimers to provide for genes encoding the subject collagen-like polymers, which may be expressed, for the most part, in unicellular organisms.

DESCRIPTION OF THE SPECIFIC EMBODIMENTS

Methods and compositions are provided for producing high molecular weight collagen-like polymers, where a major proportion of the amino acids of the polymers are present as triads having glycine as the first amino acid, where at least 40 number % of the triads comprise at least one proline and the total proline content of the triads, usually the entire polymer, is less than 45 number %. The subject polymers may be varied in a variety of ways, having a single repeating unit, having alternating repeating units, or having blocks of different repeating units. In addition to the repetitive sequences or units of triads, intervening functional sequences may also be present in the subject polymers, and sequences which will usually be present at the 5' and 3' termini that will contribute fewer than about 20 number %, more usually fewer then about 10 number % of the amino acids of the polymers. Also provided are genes encoding the subject collagen-like polymers and methods for their expression, isolation and purification. The subject collagen-like polymers find use in a variety of applications.

The collagen-like polymers of this invention will be characterized by having a molecular weight of at least about 30 kD (kiloDaltons), more usually at least about 40 kD and preferably at least about 50 kD, usually not exceeding about 150 kD, more usually not exceeding about 125 kD and frequently not exceeding about 100 kD. Being like collagen, the polymers will be further characterized in being capable of: providing helices; denaturation and renaturation; forming gels; etc. A major proportion of tripeptide triad or repetitive sequences of the subject polymers will preferably be triad sequences found in natural collagens, particularly mammalian collagen, where triad refers to a 3 amino acid peptide unit. Thus, usually at least 40%, more usually at least 50%, frequently at least 80% of the triads will be triads found in natural collagen, particularly mammalian collagen.

The subject polymers may be modified in a variety of ways, by introducing various functional units, where depending upon the functional units, they may be a part of the design, providing for the uniform alternating glycine at every third position or interrupting the uniformity, or may be present at the end of a block of repetitive units. While any of the 20 amino acids may be present, charged amino acids will usually be present in fewer than 30%, frequently in fewer than 15%, by number in the repetitive sequences.

The subject collagen-like polymers can be widely varied as to their repeating units or triads, the pattern of repeating units, the insertion of interrupting sequences, and the like. A major proportion of the amino acids present in the subject collagen-like polymers will be present as triads. As a major proportion of the amino acids are present as triads, generally at least 50 weight percent, usually at least 60 weight percent, more usually at least 80 weight percent, frequently at least 85 weight percent, of the amino acids will be present as triads (tripeptides with glycine as the first amino acid). The total number of triads in the subject polymers will usually be at least about 100, more usually at least about 150, and usually not more than about 500, more usually not more than about 400.

In the triads found in the subject polymers, glycine will be the first amino acid and the other two amino acids may vary, but will be selected so as to reduce the total proline content of the polymer between the glycines, i.e. the non-glycine two-thirds of the triads, to less than about 60 number %, usually to less than about 40 number %, but usually more than about 20 number %.

The compositions of this invention will now be described by formulae, where each capital letter indicates an amino acid, where the one letter description for an amino acid indicates that particular amino acid and where a letter which is not within the one letter description is used to symbolize any amino acid or a designated group of amino acids. The superscripts indicate that where there are a plurality of triads, the letter symbolic of amino acids may symbolize the same or different amino acid in each of the triads. Subscripts always intend the number of repeats of the symbol or formula to which the subscript relates.

For the most part, the polymers will be characterized by having, as a motif present at least twice in the collagen-like polymer, either contiguous or non-contiguous, a sequence having the following formula:

wherein X and O are any amino acids except that X and O are selected to have a proline content of the repetitive or triad sequences of the motif, usually the entire polymer, of less than about 45% by number, usually of less than about 40% by number, and may be less than 30% by number, but at least about 10% by number, usually at least about 15% by number.

Ω has from 0 to 50 amino acids, more usually from 0 to 30 amino acids, frequently from 0 to 15, and will usually be a sequence having functional capability and will be other than a repetitive glyXO motif;

n will be at least 4 and not more than about 100, more usually not more than about 75, frequently not more than about 50; and m will be at least 1, may be 2, usually at least about 3 and not more than about 20, usually not more than about 12, where particularly m is smaller as n becomes larger.

Usually, the total number of different triads in the motif will be at least 2, more usually at least 3, and not more than about 24, more usually not more than about 16 and frequently not more than about 12. The total number of different amino acids in the motif will usually be not more than about 15, more usually not more than about 10.

The number of triads including proline will usually be at least 40 number percent, more usually at least 60 number percent, although all of the triads may include one proline.

One type of collagen-like polymer will for the most part have the following motif, as a repetitive motif

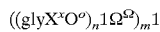

wherein X and 0 are as defined previously; x and o are the same number and will be in the range of 2 to 10, usually 3 to 8 and often 4 to 6, particularly 2, 3, 5 or 10, which intends that there will be up to and including that many different triads present in the sequence; Ω has been defined previously; Ω is 1 to $m^1$ usually not greater than 3, frequently 1 to 2, preferably 1 where Ω intends different Ω groups, similar to the 1 5 definition of x, and $m^1$ is at least 1, may be 2, usually at least about 3, and not more than about 20, usually not more than about 12, particularly as $n^1$ becomes larger; and $n^1$ is at least about 2 and not more than about 100, usually not more than about 75, more usually not more than about 50, generally not more than about 30.

For example, where x is 3, Ω is 0 amino acids, and ml is 1, one would have the formula:

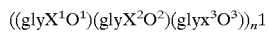

where $X^1$ is a particular amino acid, $X^2$ could be the same or different amino acid, etc., and similarly for O; and $n^1$ will generally be at least about 2, more usually about 4, and not greater than about 33, usually not greater than about 25.

One technique for synthesis of the subject compounds lends itself to a particular motif of the formula:

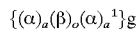

wherein:

α has from 1 to 9 triads, usually 2 to 6 triads, preferably 2 to 4 triads, more preferably 3 triads, usually at least 1 triad having a proline, more usually at least 2 triads having a proline;

β has from 1 to 24 triads, usually 2 to 18 triads, more usually 3 to 9 triads;

e will be at least 3, usually at least 6, and not more than about 50, usually not more than about 36;

g is at least 1 and not more than about 20, usually not more than about 10, more usually not more than about 8;

a and $a^1$ may be the same or different; a will be at least 1 and not more than about 6, usually not more than about 3, except that a or $a^1$ may be 0.

It will be understood that the greater the number of triads present, the lower the number of repeats required to provide the desired molecular weight.

In a preferred embodiment, these extended motifs will have, for the most part, the following formula:

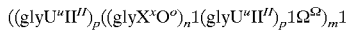

wherein:

$X^x$, $O^o$, $\Omega^\Omega$, $m^1$ and $n^1$ have all been defined previously:

U and II are any amino acids, frequently there being a proline present in at least one of the triads (see also the definitions for X and 0, which are included herein);

u and n have analogous meaning to x and o, indicating the same or different amino acids in the different triad (tripeptide) units; and p and $p^1$ will be 1 to 6, more usually 2 to 4, and the two p's may be the same or different, usually the same except that p may also be 0;

The amino acids of particular interest other than glycine will include alanine (A), isoleucine (I), leucine (L), valine (V), serine (S), threonine (T), asparagine (N), glutamine (Q), lysine (K), arginine (R), aspartic acid (D), glutamic acid (E), histidine (H), and proline (P), preferably there being at least one of a neutral polar amino acid, e.g., S or T, or a neutral aliphatic amino acid, e.g., A, I, L, or V. Usually, the aromatic hydrophobic amino acids will be avoided, e.g., F, Y and W, and the aliphatic hydrophobic amino acids (L, V, I), will usually be used only when a proline is present. For structural considerations, triad sequences containing proline, alanine, valine, serine, threonine, glutamine, or asparagine in the X or O positions form more stable triple helices. Increased stability is also conferred by triads containing hydroxyproline in the o position. For higher order assembly of triple helices, triads containing glutamic acid or aspartic acid at either the X or O positions, but especially at the X position, and triads containing lysine or arginine, at either the X or O position, but especially at the O position, are preferred.

Of particular interest is where at least one triad has proline at a second position, more preferably that two triads have proline at second positions or at least one triad has proline at a third position, sometimes having two triads having proline at a third position, there frequently being at least two triads having a proline at either the first or second position. For the most part, at least 30%, more usually at least 50% of the triads in the motifs will have proline at a second or third position and there may be some triads with proline at both positions, usually not more than 35 number percent.

The choice of triads utilized in a recombinant collagen like polymer are chosen in order to affect properties such as helix stability, hydration, solubility, gel point, adhesion, ability to cross-link, binding to metal ions, e.g. silver halides, biodegradation, and immunogenicity. For example, in order to minimize immunogenicity, triads are utilized consisting of amino acids with simple side chains such as glycine, alanine, serine, valine, and proline. When more complex amino acids are required, they can be incorporated by utilizing hexapeptide, nonapeptide, or longer triad sequences from natural collagen chains that contain these amino acids.

To a great extent, many of the polymers of the subject invention may be depicted by the following formula:

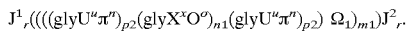

wherein all of the symbols have been described previously, except for:

$J^1$ and $J^2$ which are the same or different and are amino acid sequences of from about 1 to 40 amino acids, more usually from about 1 to 30 amino acids, and may be any sequence of convenience;

the two r subscripts are the same or different and are 0 or 1;

the two $p^2$ subscripts are the same or different, and are 0 or $p^1$.

A variety of repetitive sequences indicated by one letter amino acid designation defining the motifs may be illustrated by the following sequences: GAPGPAGPK (SEQ ID NO:01); GAPGPAGPPGAH (SEQ ID NO:02); GSPGAPGPA (SEQ ID NO:03); GAPGPAGSRGDPGPA (SEQ ID NO:04); GANGAPGPAGPAGAPGPP (SEQ ID NO:05); GAQGPAGPGGAPGPAGPG (SEQ ID NO:06); GAPGPAGAS (SEQ ID NO:07); GPAGAPGSRGDPGAPGPP (SEQ ID NO:08); GVSGPRGPAGAPGPP (SEQ ID NO:09); GAQGPAGPG (SEQ ID NO:10); GAPGPAGPP (SEQ ID NO: 133); GAPGPAGPPGSRGDPGPP (SEQ ID NO: 134) and GAQGPAGPGGSRGDPGPP (SEQ ID NO: 135).

Although any triad may be incorporated into the subject collagen like polymers, the triads will generally be those triads found in naturally occurring collagens, particularly mammalian collagens, more particularly human collagens. A large number of human collagens have been sequenced, which sequences are known in the art, see e.g., Seyer and Kang, "Covalent Structure of Collagen: Amino Acid Sequence of α1(III)-CB9 from Type III Collagen of Human Liver," Biochemistry (1981) 20: 2621-2627; Bernard et al., "Nucleotide Sequences of Complementary Deoxyribonucleic Acids for the Pro Alpha 1 Chain of Human Type I Procollagen," Biochemistry (1983) 22:5213-5223; Muragaki et al., Eur. J. Biochem (1990) 192:703-708; Kimura et al., Eur. J. Biochem. (1989) 179:71-78; Christiano et al., J. Biol. Chem. (1994) 269:20256-20262; Christiano et al., Hum. Mol. Genet. (1992) 1:475-475; Parente et al., Proc. Natl. Acad. Sci. USA (1991) 88: 6931-6935; Gammon et al., J. Invest. Dermatol. (1992) 99:691-696; Tanaka et al., Biochem. Biphys. Res. Commun. (1992) 183:958-963; Greenspan, D.S., Hum. Mol. Genet. (1993) 2:273-278; Christiano et al., Nat. Genet. (1993) 4:62-66; Soininen et al., J. Biol. Chem. (1989) 264:13565-13571; Soininen et al., FEBS Lett. (1987) 225:188-194; Brazel et al., Eur. J. Biochem. (1987) 168:529-536; Glanville et al., Eur. J. Biochem. (1985) 152:213-219; Babel et al., Eur. J. Biochem. (1984) 143:545-556; Pihlajaniemi et al., J. Biol. Chem. (1985) 260:7681-7687; Brinker et al., Proc. Nati. Acad. Sci. USA (1985) 82:3649-3653; Soinenen et al., J. Biol. Chem. (1988) 263:17217-17220; Hostikka et al., J. Biol. Chem. (1988) 263:19488-19493; Takahara et al., J. Biol. Chem. (1991) 266: 13124-13129; and Woodberry et al., J. Biol. Chem. (1989) 264:2735-2738. Triads of particular interest include GAP, GPA, GPP, GAS, GPG, GPS, GAQ, GSP, GSQ, GLQ, GPR, GPK, GAK, GAR, GER, GDR, GEP, GDA, GAH and GEA, where combinations of these triads with other triads are of particular interest, there being at least about 30 number percent, usually at least about 50 number percent of the triads, more usually at least about 60 number percent, frequently at least 80 number percent, coming within the indicated triads. In addition, while the number of triads in any one repetitive sequence or unit may vary widely, desirably the number will be 3, 5 or a multiple thereof Sequences defining the glyUII sequences indicated by one letter amino acid designation include:

GAHGPAGPK (SEQ ID NO: 11); GAHGPAGPR (SEQ ID NO: 12); GAVGAPGPK (SEQ ID NO:13); GPAGAPGEP(SEQ ID NO: 14); and GVSGPRGAP (SEQ ID NO:15)

In addition to the repeating sequences or units of triads, the subject polymers may further comprise intervening sequences or groups, where the intervening groups will be from about 1 to 50, usually from about 1 to 30, more usually from about 3 to 30 amino acids. Intervening sequences or groups of interest will be other than a repetitive unit, normally having a chemically reactive functionality, e.g. C, S, T, D, E, K or R, a physiologically active functionality, a chelating functionality, a crystal nucleating functionality, a grouping which modifies the conformational structure of the protein, or the like.

For the intervening oligomers or turns between strands of a polymer, (where by "strands" is intended an ordered sequence capable of alignment with a second strand or sequence having substantially the same or a complementary sequence, e.g. hydrophobic aligns with hydrophobic and hydrophilic aligns with hydrophilic) various sequences may be used, depending upon the desired purpose of the polymer. Thus, the intervening sequence may be unaligned, flexible, accessible, functional or combinations thereof Thus, the intervening sequence in association with the strand sequence can be designed to provide a wide variety of products which may be formed, fabricated, extruded, spun, woven, coated, or the like. The intervening sequence may provide for a ligand, which may serve to bind to antibodies, naturally occurring receptors, non-amino-acid molecules, or the like. In this way, the polymeric structures may be used to specifically bind a wide variety of molecules serving as affinity columns, photographic film, use in diagnosis, sensors, cell separation, device coatings having, for example, antithrombogenic properties, cell substrates, and the like.

The intervening sequence may provide chemically active amino acids for chemical crosslink sites, which may serve to covalently attach functional peptides, synthetic or natural polymers or proteins, non-amino acid molecules, and the like. The intervening sequence may be a naturally occurring sequence or a modified naturally occurring sequence. Specific intervening sequences of interest are listed in application Serial No. 07/609,716, now U.S. Pat. No. 5,514,581, the disclosure of which is herein incorporated by reference.

The genes may be synthesized with the method described in PCT/US87/02822 and PCT/US89/05616, the disclosures of which are herein incorporated by reference. Particularly, the genes are synthesized in accordance with the following protocol. Relatively short oligonucleotide strands are synthesized generally coding for at least 12 amino acids, and usually not more than about 60 amino acids. The complementary strands are annealed, cloned, and sequenced to establish that the correct sequences have been obtained. The ends may be blunt or staggered, usually staggered. A second approach depends on the synthesis of a single strand of the monomer. Synthetic techniques allow reasonably accurate oligonucleotide synthesis of 300 bases or more. For the most part the single strand will be in the range of about 100 to 300 bases, usually in the range of about 100 to 250 bases. The single strand is then used to produce a complementary strand, conveniently using the polymerase chain reaction ("PCR") and the resulting dsDNA cloned, purified and sequenced to ensure that it has the correct sequence. Appropriate primers may be employed, which may serve to extend the termini for multimerization by introducing a new restriction site consensus sequence, introduce intervening sequences, or the like. The monomer prepared this way will have the same limitations as to size and the number of amino acid repeating units which are encoded as the monomer prepared by the sequential or simultaneous cloning of dsDNA segments. The sequences are then multimerized and ligated and inserted into a cloning vector. After transforming into an appropriate host, the clones are analyzed for the oligomerization of the units and appropriate sized units are selected and used for expression. When flanking repetitive units of different sequences are desired, the sequence encoding the motif may be inserted at an appropriate restriction site between the flanking repetitive units, so that subsequently the gene may be excised with the appropriate flanking units. The resulting sequence encoding the motif with the flanking units may then be excised, oligomerized, and, as before, cloned and identified as to having the desired sequence and size.

The subject proteins are produced by transforming an appropriate unicellular host, such as *E coli, B subtilis,* yeast, *S. pombe, S. cerevisiae,* etc., fungi, *Neurospora, Aspergillus,* etc. A wide variety of expression vectors have been described in the literature and need not be exemplified here. The expression vector may provide for an inducible or constitutive promoter, whereby the subject proteins may be constitutively expressed or expressed only after induction. Numerous expression vectors have appropriate promoters, termination sequences, and polylinkers between the initiation and termination sequences, so that one may conveniently insert the desired gene into the polylinker to be under the transcriptional control of the promoter. In addition, the vectors may have one or more markers, which allow for selection in the transformed host. The vector may also allow for extrachromosomal maintenance or integration into the genome. The markers may provide for resistance to a toxin, e.g. an antibiotic, or complementation of an auxotrophic host to prototrophy. The choice of expression vector will depend upon on a number of factors, such as the host, economy, ease of manipulation, and the like.

Once the expression vector has been cloned, it will normally be analyzed to ensure that the gene is present and has not undergone any modification. The expression host can then be grown up in an expression media and after sufficient time, the cells lysed and the protein isolated. In some cases, the protein will be relatively insoluble and, therefore, may be separated from cellular debris by various convenient means, e.g. centrifugation. Depending on the degree of purity, the protein may be used as is, or may be further purified by extraction using a variety of solvents to extract out the impurities, while leaving the desired product in insoluble form. If desired, dilute acid solution may be used for solubilizing the protein and then precipitating the protein by dialysis. The conditions employed will vary with the particular protein produced, its solubility, the nature of the host, the nature of the contaminants, the ultimate use, and the like.

Small peptides may be prepared which include small segments of the collagen-like polymers, e.g., 15 to 36 amino acids. These segments may be used as haptens, by conjugating the segment to an appropriate immunogen, and the resulting immunogen used for production of antisera or monoclonal antibodies specific for the sequence. Thus, antibodies may be produced which specifically bind to the collagen-like polymers of the subject invention. Depending on the solubility of the subject polymers, the antibodies may be used for affinity purification, identification of the polymers on Western blots, or non-covalently crosslinking of the polymers to produce novel structures and the like.

The subject compositions may find use for a variety of applications, including medicine, research, industry, and the like. The subject collagen-like polymers are useful in the formulation of materials, such as fibers, membranes, films, hydrogels, colloid suspensions and molded articles, where the materials find use as coatings, structural materials, and the like, imparting unique characteristics to these materials and to a variety of surfaces from either naturally occurring or synthetic sources, the characteristics usually being associated with water absorption, biocompatibility, or interaction with non-protein compounds of either organic or inorganic nature, e.g. silver halide, dyes, etc. Coatings of 1 to 100 mm may find use, with adherency to a variety of surfaces from naturally occurring and synthetic sources. Distinctive properties of these polymers are their thermal reversible gelation at specific temperatures, their inherent biocompatibility and their bioresorption. Therefore, the subject polymers may find application in photographic films, as wound dressings allowing for neovascularization (see Peters, "Biological Dressings in Burns—A Review", Ann. Plas. Surg. (1980) 4:133-137), eye medications, bone cements, matrices and coatings for artificial organs (See Hilbert et al., "Tissue-Derived Biomaterials and their Use in Cardiovascular Prosthetic Devices," Med. Prog. Techol. (1988) 14: 115-163, Lane & Sandhu, "Current Approaches to Experimental Bone Grafting," Orthrop. Clin. North Am. (1987) 18:213-225, Alsbjorn, "In Search of the Ideal Skin Substitute," Scand. J. Plast. Reconstr. Surg. (1984) 18:127-133), plastice surgergy (See Flaguel & Halimi, "Injectable Collagen: An Evaluation After 10 Years Use as a Complement in Plastic Surgery", Ann. Chir. Plast. Esthet (1994) 39:765-771; Elson, "Soft Tissue Augmentation," Dermatol. Surg. (1995) 21:491-500), membranes, matrices and coatings for growing and/or studying cultures (See Visconti et al., Use of Reconstituted Basal Membranes for the Study of Invasion of Human Tumor Cells: Current Status and Future Prospects, "Boll. Soc. Ital. Biol. Sper." (1990) 66:365-372; Boswell & Swan, "Mononuclear Phagocytes and Collagen Matrices--A Review," Scan. Electron. Microsc. (1984) 4:2045-2058), implantable or injectable drug delivery systems (See Sadler & Horsey, "The New Gelatins . . . ," Anaesthesia (1987) 42:998-1004), and the like.

Furthermore, since natural collagen is cross-linked it cannot be redissolved for spinning, shaping, etc. without digestion and molecular weight reduction. Thus, the collagen-like polymers retain the desired collagen characteristics and are capable of being processed.

The following examples are offered by way of illustration and not by way of limitation.

EXPERIMENTAL

EXAMPLE 1

DNA Preparation Methods

1. Preparation of plasmid DNA from E. coli.
A. Small scale. Plasmid DNA was prepared from 1.5 ml cultures by either the boiling procedure or the alkaline lysis method (Maniatis et al., Molecular Cloning: A Laboratory Manual, Cold Spring Harbor Laboratory, Cold Spring Harbor, (1982).
B. Large scale. A plasmid-carrying strain was grown overnight in 1 liter of Luria broth with the appropriate antibiotic. The cells were collected by centrifugation at 10,000×g for 5 minutes and resuspended in 10 ml of ice cold TE (10 mM Tris-HCl pH 8, 1 mM EDTA). The cells were centrifuged again, resuspended in 4 ml of TES (TE and 25 % w/v sucrose) and homogenized by vortexing. The samples were kept on ice for the following steps. Lysozyme (1 ml of 10 mg/ml) was added to the cell suspension and incubated for 5 minutes before the addition of 2 ml of 0.5 M EDTA pH 8. After 10 minutes incubation, 50 ml of proteinase K (40 mg/ml) were added followed 10 minutes later with 15 ml of lysing buffer (0.1% Triton X-100, 1 mM EDTA, 50 mM Tris-HCl pH 8). After 15–20 minutes, the cell lysate was centrifuged at 35,000xg for 90–120 minutes. The supernatant (19.8 ml) was transferred to a plastic tube with 20 mg of CsCl and 400 $\mu$l of ethidium bromide (10 mg/ml). After dissolution, the mixture was divided into two polyallomer ultracentrifuge tubes, sealed with heat and centrifuged in a Beckman Ti 65 rotor at 60,000 rpm for 24 hours. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Deproteinization.
Phenol extraction was performed on a convenient volume of DNA sample, typically between 100 $\mu$g[1] to 10 ml. The DNA sample was diluted in 0.01 M Tris-HCl pH 7.5, 1 mM EDTA and an equal volume of water-saturated phenol was added. The sample was vortexed briefly and placed on ice for 3 minutes. After centrifugation for 3 minutes in a microfuge, the aqueous layer was removed to a new tube and extracted once with an equal volume of chloroform:isoamylalcohol (24:1).

3. Ethanol precipitation.
DNA in an aqueous buffer was concentrated by ethanol precipitation. To the DNA sample was added 1/10 volume of 3 M sodium acetate pH 7.5 and 2–3 volumes of cold ethanol. The DNA was precipitated for 30 minutes at −70° C. or overnight at −20° C. and then pelleted by centrifugation in the microfuge for 15 minutes at 4° C. The pellet was washed once with 200 $\mu$l of cold 80 % ethanol and precipitated again for 10 minutes at 4° C. After air drying or lyophilization, the pellets were resuspended in the appropriate buffer.

4. Phosphatase treatment of DNA.
A. Phosphatase treatment of DNA was performed by adding 1 $\mu$l (25 units) of calf intestinal phosphatase (Boehringer Mannheim) directly to the restriction enzyme digestion reaction and continuing the incubation for 30 minutes at 37° C. The phosphatase was inactivated for 60 minutes at 65° C. prior to deproteinization by phenol extraction.
B. Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 $\mu$g/ml. Shrimp Alkaline Phosphatase (SAP) was added at 2 U/$\mu$g of DNA and the mixture was incubated at 37° C. for one hour, heat inactivated for 20 minutes at 65° C. and then passed through a Probind filter (Millipore) and subsequently a Bio-Spin column. The DNA was then ethanol precipitated and resuspended in suitable buffer.

5. Phosphorylation of DNA.
Phosphorylation before annealing was performed by using Polynucleotide Kinase 3'-phosphatase-free (Boehringer Mannheim). The reaction was carried out at 37° C. for 30 minutes in a 50 $\mu$l reaction volume containing: 12.5 $\mu$g DNA, 5 $\mu$l 10x kinase buffer (0.5M Tris pH 7.5, 10 mM Spermidine, 0.1 M $MgCl_2$, 150 mM DTr, 1 mM EDTA), and 2 $\mu$l Polynucleotide Kinase (10 U/$\mu$l). After phosphorylation, salts and glycerol were removed from the DNA strands using a Bio-Spin 6 column (BioRad) equilibrated in TEAB.

6. Fill-in reaction with DNA polymerase I.
DNA was resuspended in buffer containing 50 mM Tris-HCl pH 7.4, 50 mM KCl, 5 mM $MgCl_2$, and 400 $\mu$M each of the four deoxynucleotide triphosphates. Ten units of Klenow DNA polymerase (BRL) were added, and the reaction was allowed to proceed for 15 minutes at room temperature. The DNA was then phenol extracted and ethanol precipitated.

7. Digestion with restriction endonucleases.

DNA was digested with restriction endonucleases (REN) in 1×"AA" buffer [10×AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 µg/25 µl. Incubation was at 37° C. for 1–4 hours for most restriction endonucleases except for Ball, Banl and Nael digestions which were incubated overnight.

8. Analytical agarose gel electrophoresis of DNA.

To DNA samples for gel analysis was added 0.2 volumes of loading buffer (5×electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1×TAC or ½×TBE. The 1×TAC is 40 mM Tris-base, 10 mM EDTA, adjusted to pH 7.8 with acetic acid. The ½×TBE is 0.045 M Tris-base, 0.045 M boric acid, 1 mM EDTA, pH 8. The gel was run at 40–50 V for 18 hours, then removed and stained with 0.5 ag/ml ethidium bromide for 30 minutes. The DNA bands were visualized on a long wavelength UV transilluminator.

9. Preparative agarose gel electrophoresis.

The procedures and materials are the same as for the analytical agarose gel electrophoresis. The only difference is the use of low melting point (LMP) agarose, ranging in concentration from 0.5 to 2.5 % (w/v) depending on the size of the DNA fragment to be purified. DNA restriction fragments were excised from the LMP agarose gels after visualization with ethidium bromide. For agarose ligation the buffer used was 1×TAE (50 mM Tris Acetate pH 7.8).

10. NACS purification.

Gel fragments containing DNA were melted at 70° C. for 5 minutes and diluted approximately 5 fold with TE1 (10 mM Tris-HCl pH 7.5, 0.2 M NaCl). The gel solution was applied to a NACS column (BRL). The column was washed with 5 ml of the same buffer. The bound DNA was eluted with 300 ,ul of either TE2 (10 mM Tris-HCl pH 7.5, 1.0 M NaCi) for DNA fragments smaller than 1000 bp or TE3 (10 mM Tris-HCl pH 7.5, 2 M NaCl) for larger fragments. The eluted DNA was concentrated by ethanol precipitation.

11. DNA ligation.

Reactions for ligating cohesive ends contained: 1 µg DNA, 1×AA buffer (see step 7, above) 1 mM ATP and 20 units of T4 DNA ligase (BRL) in a 20 µl final reaction volume. The ligation was allowed to proceed for 16–18 hours at 15° C. or 1–2 hours at room temperature. For blunt-ended ligations the reactions contained 1 µg DNA, 25 mM Tris-HCl pH 7.5, 5 mM MgCl$_2$, 5 mM DTT, 0.25 mM spermidine, 200 mg BSA, 1 mM hexamine cobalt chloride (HCC), 0.5 mM ATP and 400 units T4 DNA ligase (NEB) in a 20 µl reaction volume. The ligation was allowed to proceed for 30 minutes to 1 hour at room temperature.

12. Agarose DNA ligation.

The agarose was melted at 65° C., the temperature was then lowered to 37° C. and ligation buffer (5X=100 mM Tris-HCl, pH 7.5, 50 mM MgCl$_2$, 50 mM DTT, 1 mM ATP) was added; the tube was then placed at room temperature and ligase was added (1000 units T4 DNA ligase (NEB)), the reaction volume was usually 50 µl. The reaction was incubated at 15° C. for 16–18 hours.

13. Use of Filters and Columns for DNA Purification.

A. Ultrafree®-Probind filter unit ("Probind", Millipore): the DNA containing solution was applied to the filter unit and spun at 12,000 RPM for 30 seconds in a Sorvall Microspin 24S.

B. Microcon-30 filter (Amicon): the DNA containing solution was washed by applying to the filter and exchanging twice with H$_2$O by spinning at 12,000 RPM for 6 min in a microfuge.

C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

14. Agarose DNA Purification Using Ultrafree®O-MC Filter Unit.

This procedure can be used for agarose slices up to 400 µl in size. After agarose gel electrophoresis the DNA is visualized by ethidium bromide staining and the agarose block containing the DNA band of interest is excised. The agarose is then frozen at −20° C. for 1 hour; then quickly thawed at 37° C. for 5 minutes. The agarose is then thoroughly macerated. The pieces are then transferred into the sample cup of the filter unit and spun at 5,000×g in a standard microfuge for 20 minutes. The agarose is then resuspended in 200 µl of Tris-EDTA, or other buffer, and incubated at room temperature for 30 min to allow for elution of additional DNA from the gel. The mixture is then centrifuged for an additional 20 min at 10,000 RPM. The DNA is, at this point, in the filtrate tube separated from the agarose fragments and ready for subsequent DNA manipulations.

mRNA Methods

1. Preparation of mRNA.

Summers, W. C. (Anal. Biochem. 33:459–463 (1970). Cells were grown at 30° C. or 42° C. in LB medium supplemented with kanamycin (50 µg/ml). 10 ml of cells at OD$_{600}$ 1.0 were spun and the cell pellet was resuspended in 10 ml of protoplasting buffer (15 mM Tris-HCl pH 8.0, 0.45 M sucrose, 8 mM EDTA); 80 µl of lysozyme at 50 mglml were added and the mixture was then incubated on ice for 15 minutes. The cell suspension was spun for 5 minutes at 7,000 RPM in an SS-34 rotor using an RC-SB centrifuge. The pellet was resuspended in 0.5 ml of lysing buffer (10 mM Tris-HCl pH 8.0, 10 mM NaCl, 1 mM Na-Citrate, 1.5% w/v SDS) and 15 µl of DEPC. The suspension was mixed gently and then transferred to a 1.5 ml Eppendorf tube, incubated at 37° C. for 5 minutes and then chilled on ice. 250 µl of saturated NaCl (40% w/v) were added, mixed gently, and the incubation, on ice, was prolonged for an additional 10 minutes. The slurry was spun at 4° C. for 15 minutes. The supernatant was placed in two 1.5 ml tubes and 1 ml of 100% ethanol was added to each. The RNA was precipitated in the cold and then spun at 4° C. for 20 minutes. The pellets were rinsed in 70% ethanol and dried. The RNA was then resuspended in 0.1 ml H$_2$O and OD$_{260}$ and OD$_{280}$ were taken to measure the recovery and purity of the RNA. The average recovery of total RNA (5 % mRNA, 95% tRNA+ rRNA), from 10 ml of growing cells, was between 0.5 and 1.0 mg.

2. Northern blot analysis.

The RNA, purified as described above, was run on agarose gel and transferred to nitrocellulose following the procedure described in Maniatis et al., Molecular Cloning: A Laboratory Manual, Cold Spring Harbor Laboratory, Cold Spring Harbor (1982), pp 202–203, using 1OX SSC as transfer buffer. The ECL gene detection system kit (Amersham) was used for labelling of the probe, hybridization conditions and detection. The procedures were executed as described in: ECL gene detection system RPN2101, version 2, Amersham International plc.

Bacterial Transformation Methods

1. Preparation of transformation-competent E. coli cells.

A culture of 200 ml of sterile L broth was inoculated with a small loopful of E. coli cells. This was incubated with shaking at 37° C. until the $OD_{600}$ was approximately 0.5. The culture was placed on ice for 10 minutes and centrifuged at 6,000×g for 10 minutes. The cell pellet was resuspended in 100 ml of ice-cold 0.1 M $MgCl_2$, kept on ice for 30–40 minutes and centrifuged again. The pellet was resuspended in 2 ml of ice-cold 100 mM $CaCl_2$, transferred to a sterile test tube and incubated on ice for 24 hours. The competent cells were then aliquoted and stored at −70° C.

2. Transformation of E. coli.

An aliquot of frozen competent cells was thawed on ice. To 50 μl of cells, 0.1 to 1 μg of DNA was added and the mixture was incubated on ice for 30 minutes. The tube was removed from ice and placed in a 42° C. bath for 2 minutes. L broth (1 ml) was added and the transformation mix incubated with shaking at the desired temperature (usually 30° C. or 37° C.) for 2 hours. Then one-tenth of the transformation was plated on L broth plates containing the appropriate antibiotic and, when necessary, XGAL and IPTG were added.

Antibody Production, Protein Chemistry and Electrophoresis of Proteins

1. Preparation of antibody to artificially synthesized Peptides.

A synthetic peptide of sequence GAHGPAGPKGAHGPAGPKGAPGPAGPPGAPGPA-GPP (SEQ ID NO:16) (SequenceD-$C_2A_2$) where $C_2A_2$ defines an amino acid sequence motif indicated by one letter amino acid designation was coupled to keyhole limpet hemocyanin for use as an immunogen. The material was sent to Antibodies, Inc. for preparation of antibodies in rabbits. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microfiter RIA using the synthetic peptide as antigen. Kagen and Glick (1979), in Methods of Radioimmunoassay, Jaffe and Berman (eds.), Academic Press, p 328. Antisera was obtained that reacted with synthetic peptides of the SequenceD1 and SequenceD2 sequences.

Following the procedure described above an additional peptide was synthesized having the sequence (GAPGPAGPPGSRGDPGPP)$_2$ (SEQ ID NO: 17) (SequenceD-(AB)$_2$), which was also coupled to keyhole limpet hemocyanin for use as an immunogen. Polyclonal antisera were then prepared as described above, which bound to the synthetic peptide of the SequenceD3 sequence.

Following the procedure described above an additional peptide was synthesized having the sequence (GAPGAPGSQGAPGLQ)$_2$ YMK (SEQ ID NO: 18) which was also coupled to keyhole limpet hemocyanin for use as an immunogen. Polyclonal antisera were then prepared as described above, which bound to the synthetic peptide of the CLP 3. 1, CLP 3.7 and PPAS sequences described below.

2. Polyacrylamide gel electrophoresis of proteins.

Approximately $10^9$ E. coli cells from growing cultures were pelleted by centrifugation at 10,000×g for 5 minutes. The cell pellets were resuspended in 100 to 500 μl of 2X sample buffer (100 mM Tris-HCl pH 6.8, 4% SDS, 10% β-mercaptoethanol, 60% glycerol or sucrose) and sonicated for 30 seconds using a Tekmar sonic disrupter. Samples were boiled for approximately 5 minutes and 20 to 100 μl of the cell lysates were loaded on an SDS-polyacrylamide gel (7.5 to 16% w/v). The gels were prepared following the procedure of Laemmli, U.K.(1970), Nature (London), 2:680–685. The proteins in the gels were stained with 2% Coomassie brilliant blue in 10% methanol, 7.5% acetic acid for 1 hour and destained in 10% methanol, 7.5% acetic acid overnight.

3. Protein expression analysis.

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 300C. When the culture reached an $OD_{600}$ of 0.8, 40 ml were transferred to a new flask prewarmed at 42° C. and incubated at the same temperature for approximately 2 hours. The cultures (30° C. and 42° C.) were chilled on ice and $OD_{600}$ was taken. Cells were collected by centrifugation and then divided in $OD_{600}$ aliquots and used to perform western analysis using the appropriate antibodies.

4. Immunoblotting of proteins in gels.

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM1 1307) was saturated with transfer buffer and laid on the gel. Air bubbles between the filter and the gel were removed. The gel and nitrocellulose filter were placed in the transfer unit as specified by the manufacturer (Bio-Rad). Transfer was allowed to proceed at 200 mA for 3–4 hours. Then the nitrocellulose filter was removed and stained with Amido-Schwartz for 3 minutes (0.05% Amido black, 45% deionized $H_2O$, 45% methanol, 10% acetic acid) and destained in $H_2O$. The filter was incubated for at least 10 minutes at room temperature in "BLOT0O" (5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5X Blotto (2.5% nonfat dry milk, 50 mM Tris-HCl pH 7.4, 0.9% NaCl, 0.2% sodium azide) and was gently agitated for approximately 16 hours at room temperature. The filter was washed for 1 hour with 5 changes of TSA (50 mM Tris-HCl pH 7.4, 0.9% NaCl, 0.2% sodium azide). The blot was placed in 15 ml of 0.5X BLOTTO solution containing 1×$10^7$ cpm of $^{125}$I-protein A and gently agitated for 2 hours at room temperature. The filter was washed for 2 hours with a minimum of 7 changes of TSA, rinsed once with deionized H20 and air dried. The blot was covered with Saran® wrap and autoradiographed.

An alternative to the $^{125}$1I-Protein A detection method was also used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, CA. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 minutes with 3 changes of TSA (50 mM Tris-HCl pH 7.4, 0.9% NaCl, 0.2% sodium azide). The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1 % Tween 20. The blot was then washed three times for 5 minutes each in TBS with 0.3% Tween 20 and then three times for 5 minutes each in TBS with 0.1 % Tween 20. The blot was then incubated for 1 minute with gentle agitation in 12 ml of development solutions #1 an #2 (Amersham) equally mixed. The blot was removed from the development solution and autoradiographed.

5. Amino Acid Analysis.

Amino acid compositions were determined by the PTC derivatization procedure of Henrickson and Meredith (1984). Protein samples were hydrolysed with 5.7 N constant boiling HCl at 108° C. for 24 hours in vacuo. After reaction with PITC, amino acid derivatives were detected at 254 nm by HPLC reverse phase chromatography using a Hewlett Packard 1090 or Waters 600E system and a Supelco C18 column (4.6 mm×25 cm) with a linear gradient of 0–50% acetonitrile in 0.1 M $NH_4OAc$ pH 6.78 as a mobile base. Henrickson, R. L. and Meredith, S. C. (1984) Amino Analysis by Reverse Phase High Performance Liquid Chromatography., *Anal. Biochem.* 137:65-74.

6. Peptide Synthesis.

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, (1984)). Crude peptides were desalted by chromatography over Sephadex G-50. Sarin, V.K., Kent, S. B. H., Tam, J. P. and Merrifield, R. B. (1981) *Anal. Biochem.* 237:927-936. Stewart, J. M. and Young, J. D. (1984) Solid Phase Peptide Synthesis, Pierce Chemical Company, Rockford, II pp 85–89.

Synthetic DNA Methods

1. In vitro DNA synthesis.

The N,N-diisopropyl phosphoramidites or β-cyanoethyl phosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A or 381A DNA synthesizer using a 10-fold excess of protected phosphoramidites and 1 μmole or 0.2 μmole of nucleotide bound to the synthesis support column. The chemistries used for synthesis are the standard protocols recommended for use with the synthesizer and have been described (Matteucci et al., *J. Amer. Chem. Soc.*, 103:3185-3319 (1981)). Deprotection and cleavage of the oligomers from the solid support were performed according to standard procedures as described by McBride et al., *Tetrahedron Letters*, 24:245-248 (1983). The repetitive yield of the synthesis as measured by the optical density of the removed protecting group as recommended by Applied Biosystems (1984) was greater than 97.5 %.

The crude oligonucleotide mixture was purified by preparative gel electrophoresis as described by the Applied Biosystems protocols of Nov. 9, 1984 (User Bulletin No. 13) and as updated in 1992. The acrylamide gel concentration varied from 10 to 20% depending upon the length of the oligomer. If necessary, the purified oligomer was identified by UV shadowing, excised from the gel and extracted by the crush and soak procedure (Smith, *Methods in Enzymology* :371-379 (1980)).

For DNA synthesis of oligonucleotides longer than 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001 %) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2x to 3x over the recommended time. The time allocated for the capping was also increased to limit truncated failure sequences. After the synthesis the deprotection was done at 550C for 6 hours. After desalting the synthesized DNA was amplified using PCR.

2. Sequencing of DNA.

DNA sequences were determined by the following methods. Fragments containing the region of interest were cloned into the multiple cloning site of M13mpl8 or M13mpl9 (Maniatis et al., 1982, and Norrander et al. 1983. *Gene*, 6:101-106). Single-stranded DNA was prepared and sequenced by the primer extension method (Sanger et al. 1977 *Proc. Natl. Acad. Sci USA*, 14:5463-5467 and Biggin et al., 1983. *Proc. Natl. Acad. Sci.USA*. 80:3963-3965) using 35S-deoxyadenosine 5'-(alpha-thio)-triphosphate (New England Nuclear) as label. In some cases, reverse transcriptase (Molecular Genetics) was used to extend the primer, using the dideoxy:deoxynucleoside triphosphate ratios utilized by Zagursky et al. *Gene Anal. Techn.* (1985) 2:89-94. Deoxyadenosine triphosphate labeled with either $^{32}P$ or $^{35}S$ was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 μM instead. In the other mixes, the concentration of dideoxyGTP in the G reaction was 0.5 mM. All sequences were run on 6 or 8% polyacrylamide gels containing 8 M urea (Sanger et al. 1978, *FEBS Letters*, 87:107-110.). Primers used for sequencing were purchased from P-L Biochemicals. Storage and analysis of data utilized software from both DNAstar and International Biotechnologies, Inc for IBM personal computer and DNA Strider, DNA Inspection IIe or DNAid for Apple Macintosh personal computer.

3. Dideoxy DNA sequencing of double stranded plasmid DNA.

Plasmid DNA was prepared as described previously (Preparation of plasmid DNA from E. coli, Small scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

4. PCR amplification:

The PCR reaction was performed in a 100 $\mu$l volume in a Perkin Elmer thin-walled Gene Amp™ reaction tube. Approximately 1 $\mu$l of each primer DNA (corresponding to a 0.1 $\mu$M final concentration) was added to 1×PCR buffer (supplied by Perkin Elmer as 10×solution), 200 $\mu$M of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by Agarose Gel Electrophoresis using 1.5% Low Melting Point agarose in 0.5×TA buffer. The reaction mixtures that gave the desired band were pooled and spun through an Ultrafree-Probind filter unit (Millipore) at 12,000 rpm for 30 seconds in a Sorvall Microspin 24S to remove the AmpliTaq enzyme. The buffer was then exchanged with $H_2O$ two times, using a Microcon-30 filter (Amicon) by spinning at 12,000 RPM for 6 min in a microfuge. Salts and glycerol were removed from the amplified dsDNA using a Bio-Spin 6 column (BioRad) equilibrated in TEAB, in a Sorvall RC5B centrifuge using an HB4 rotor at 2,500 RPM for 4 min. The DNA was then concentrated in vacuo.

Fermentation Conditions

The fermentor is a 15 L Chemap, 10 L working volume. The culture conditions are: temperature=30° C., pH 6.8; NaOH 2.5 M is used for pH regulation. The headspace pressure is below 0.1 bar. The dissolved oxygen is regulated at 50%. The air flow varies from 0.5 L/min to 20 L/min. The agitation rate varies between 200 to 1500 rpm. The fermentor is inoculated with a 10% (v/v) inoculum grown in medium A for 15 hours at 30° C. under agitation.

Medium B, C or D was the fermentor medium. The starting volume in the case of 10 liter fermentation is no less than 3 L, and in the case of a 1 liter fermentation, is no less than 0.5 liters.

If the fermentor starting volume is less than the final volume desired, then when the carbon source concentration reaches 1 %, a concentrated solution (5x) of medium B,C, or D, respectively, is added to the fermentor in order to keep the carbon source concentration approximately 1 %.

When the culture reached an $OD_{600}$ of 60.0, the temperature was increased to 42° C. for 10 min, then lowered to 39° C. or 40° C. for 2 to 3 hours. The cells were then harvested by centrifugation and frozen at −70° C. until processed.

Other fermentors used for the expression of protein polymers were usually a 15 1 MBR, 10 1 working volume, or a 13 1 Braun Biostat E, 8.5 1 working volume. The choice of the fermentor and its size is not critical. Any media used for the growth of E. coli can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in E. coli was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., *Chem. Eng. Commun.* (1986), 45: 229-240. Seo, J. H.; Bailey, J. E., *Biotechnol. Bioeng.* (1986), 2: 1590–1594.

TABLE 1

MEDIUM TABLE

| Constituent | g/L |
|---|---|
| Medium A: LB Medium | |
| NaCl | 10 |
| tryptone | 10 |
| yeast extract | 5 |
| kanamycin | $5 \times 10^{-3}$ |
| Medium B | |
| $NH_4Cl$ | 4.5 |
| $KH_2PO_4$ | 0.76 |
| $MgSO_4 \cdot 7H_2O$ | 0.18 |
| $K_2SO_4$ | 0.09 |
| $CaCl_2$ | $24 \times 10^{-3}$ |
| $FeSO_4 \cdot 7H_2O$ | $7.6 \times 10^{-3}$ |
| TE | 0.5 ml |
| casamino acids | 25 |
| yeast extract | 5 |
| glucose | 20 |
| kanamycin | $5 \times 10^3$ |
| Medium C | |
| yeast extract | 20 |
| casamino acids | 20 |
| peptone | 20 |
| gelatin peptone | 20 |
| $KH_2PO_4$ | 2 |
| $K_2HPO_4$ | 2 |
| $Na_2HPO_4 \cdot 7H_2O$ | 2 |
| glucose | 2 |
| ampicillin | 0.1 |
| Medium D | |
| $(NH_4)SO_4$ | 5.6 |
| $K_2HPO_4$ | 6.7 |
| $MgSO_4 \cdot 7H_2O$ | 7.8 |
| $NaH_2PO_4 \cdot H_2O$ | 3.8 |
| EDTA | 0.98 |
| Trace Elements | 50 |
| Glucose or glycerol | 20 |
| Kanamycin or ampicillin | $5 \times 10^{-3}$ |

EXAMPLE 2

CLP AND CLP-CB

The design of a collagen-like polymer with thermoreversible gelation character.

The collagen-like polymer CLP was designed predominantly of repeating GPP tripeptides (8 within each monomer segment). Other tripeptides were included in order to decrease the overall repetitiveness of the gene and to allow the use of additional codons which could be used to better manipulate the DNA. These were GAP (twice), GPA, GPV, and GSP. All of these triplets occur in natural collagen although never in the sequence and context used in CLP. The properties of CLP were designed to yield a protein polymer that would undergo thermoreversible gelatin at high temperatures, as well as being nonimmunogenic. The high stability of the helices should create high tensile strength in fibers or membranes formulated from CLP. These chain properties should allow the creation of hydrogel colloids in aqueous solutions which when applied to hard substrates should act as soft coatings. Because of the simple sequence of CLP, its optical absorbance should be minimal in all wavelengths down to 220 nm.

The design of a soft coating material with cell attachment function.

The versatile formulation properties of collagen-like polymers makes them ideal as biomaterials used in implantable devices. Either as a coating on the surface of prostheses or as a structural component of the device itself, CLP could promote tissue integration by providing improved blood and cellular interaction. The latter function is mediated in natural collagen by a specific amino acid sequence which acts as a ligand for a cellular receptor. In order to create a CLP polymer with cell attachment activity, the sequence GLPG-PKGDRGDAGPKGADGSP (SEQ ID NO: 19) was included within the CLP monomer sequence (CLP-CB). In contrast to the hydrophobic GPP collagen-like flanking sequences, this block of 21 highly charged hydrophilic amino acids should form a destabilized flexible helical region accessible for interaction with cells. Promotion of epithelialization of the surface of an implanted device will improve the compatibility and rejection characteristics increasing its lifetime and safety. The subject compositions may find use as wound dressings, allowing for neovascularization, eye applications, matrices for artifical organs and the like.

Construction of CLP monomer.

The CLP (Collagen-Like Protein) synthetic gene was assembled from smaller parts. First, three double-stranded sections of DNA ranging from 40 to 60 bp in length were chemically synthesized as described above.

multiple cloning site of the acceptor plasmid) were cloned separately into plasmid pUC19 (See United States Biochemical Life Science Research Products, 1994–1995 Catalogue, p 365) that had been digested with the appropriate REN. The DNA sequence was verified and two plasmids were selected pPTO 1 1 and pPTO1 12, carrying the correct sequence. Section B was ligated into PTO1 1 1 that had been digested with BanII and SmaI RENs. Plasmid pPTO1 13 was sequenced and found correct.

Plasmids pPTO1 12 and pPTO1 13 were digested with the appropriate RENs to release section C and Sections A+B, respectively. After purification, these DNA fragments were ligated into pSY937 (described in U.S. Pat. No. 5,243,038) previously digested with BanI and EcoRV RENs. The product of the ligation reaction was transformed into E. coli strain HB101. Plasmid DNA from transformants was purified and digested with BanI; clones containing inserts of the correct size were sequenced. Plasmid pPT0116 contained the desired sequence shown for section A+B+C (see Table 2). This plasmid was digested with BanI REN, and the digestion mixture was diluted and ligated with T4 DNA Ligase. E. coli HB 101 competent cells were transformed and screened for loss of the CLP insert; one plasmid, pPT0125, was selected to be used as the acceptor vector for subsequent constructions.

```
A
        EcoRI      BanI                                          BanII    (Asp718)
1) AATTCGGTGCCCCTGGTCCGCCTGGTCCGCCTGGTCCACCGGGTCCTCCGGGGCTC
2)     GCCACGGGGACCAGGCGGACCAGGCGGACCAGGTGGCCCAGGAGGCCCCCGAGCATG
(SEQ ID NOS: 20&21)

B
    BanII                                    SmaI
3)     CCGGGTCCTCCAGGACCGCCAGGTCCGCCTGGTCCCCC
4)  CCGAGGCCCAGGAGGTCCTGGCGGTCCAGGCGGACCAGGGGG
(SEQ ID NOS: 22&23)

C
    SmaI                                BanI      FspI       EcoRV   SalI
5) GGGTCCTGCAGGTCCAGTAGGTAGCCCCGGTGCCATGTGTGCGCATCGATATC
6) CCCAGGACGTCCAGGTCATCCATCGGGGCCACGGTACACACGCGTAGCTATAGAGCT
(SEQ ID NOS: 24&25)
```

Sections A and C (the sequence of section C after the BanI REN site is not coding for CLP but is a modification of the

TABLE 2

```
    G   A   P   G   P   P   G   P   P   G   P   P   G   P   P   G   A
5'-GGTGCCCCTGGTCCGCCTGGTCCGCCTGGTCCACCGGGTCCTCCGGGGGCT
3'-CCACGGGGACCAGGCGGACCAGGCGGACCAGGTGGCCCAGGAGGCCCCGCA

P   G   P   P   G   P   P   G   P   P   G   P   P   G   P   A   G   P
CCGGGTCCTCCAGGACCGCCAGGTCCGCCTGGTCCCCCGGGTCCTGCAGGTCCA
GGCCCAGGAGGTCCTGGCGGTCCAGGCGGACCAGGGGGCCCAGGACGTCCAGGT

V   G   S   P   G   A
GTAGGTAGCCCCGGTGCC-3'
CATCCATCGGGGCCACGG-5'
(SEQ ID NO: 26 & 27)
```

Construction of CLP-CB monomer.

Two oligonucleotide strands were synthesized as described in Example 1.

```
      AvaI                         PvuI                                          AvaI
i)  CCGGGACTGCCAGGCCCGAAAGGCGATCGTGGCGACGCCGGTCCTAAAGGCGCAGATGGCAGC
ii) GGCCCTGACGGTCCGGGCTTTCCGCTAGCACCGCTGCGGCCAGGATTTCCGCGTCTACCGTCGGGCC
(SEQ ID NOS: 28 & 29)
```

The two oligonucleotide strands were annealed and ligated with the DNA of plasmid pPT0116 (CLP monomer in pSY937) which had been digested with AvaI REN.

The products of this ligation reaction were transformed into F. DQii strain HB101. Plasmid DNA from transformants was purified and digested with BanI; clones containing inserts of the correct size were digested with PstI and BglI RENs for the determination of orientation. Plasmid DNA from correct clones was sequenced. Plasmid pPT0117 (shown in Table 3) contained the desired CLP-CB monomer sequence, olignonucleotides (i) and (ii) are shown below in bold and underlined.

0.5 kbp to 3.5 kbp. One clone pPT0190, with an insert of approximately 0.9 kbp was chosen for expression and protein analysis.

CLP-CB

Plasmid DNA from pPTO1 17 was digested with BanI REN and the digestion fragments were separated by agarose gel electrophoresis. The CLP-CB gene fragment, 180 bp, was excised and purified by NACS column (see Example 1). The purified fragment was ligated with plasmid pSY1261 which had been digeted with REN BanI. The product of this ligation reaction was transformed into E. c strain HB101. Transformants were selected for resistance to kanamycin. Plasmid DNA from individual transformants was purified and analyzed for increased size due to CLP-CB multiple DNA insertion. Several clones were obtained ranging in size

TABLE 3

```
    G   A   P   G   P   P   G   P   P   G   P   P   G   P   P   G   A
5'-GGTGCCCCTGGTCCGCCTGGTCCGCCTGGTCCACCGGGTCCTCCGGGGGCT
3'-CCACGGGGACCAGGCGGACCAGGCGGACCAGGTGGCCCAGGAGGCCCCGCA

P   G   P   P   G   P   P   G   P   P   G   L   P   G   P
CCGGGTCCTCCAGGACCGCCAGGTCCGCCTGGTCCCCCGGGACTGCCAGGCCCG
GGCCCAGGAGGTCCTGGCGGTCCAGGCGGACCAGGGGGCCTGACGGTCCGGGC

K   G   D   R   G   D   A   G   P   K   G   A   D   G   S   P
AAAGGCGATCGTGGCGACGCCGGTCCTAAAGGCGCAGATGGCAGCCCG
TTTCCGCTAGCACCGCTGCGGCCAGGATTTCCGCGTCTACCGTCGGGC

G   P   A   G   P   V   G   S   P   G   A
GGTCCTGCAGGTCCAGTAGGTAGCCCCGGTGCC-3'
CCAGGACGTCCAGGTCATCCATCGGGGCCACGG-5'
(SEQ ID NO: 30&31)
```

CLP and CLP-CB Polymer Construction.

CLP

Plasmid DNA from pPT0116 was digested with BanI REN and the digestion fragments were separated by agarose gel electrophoresis. The CLP gene fragment, 117 bp, was excised and purified by NACS column (see Example 1). The purified fragment was ligated with plasmid pSY1262 which had been digested with REN BanI. The product of this ligation reaction was transformed into E. MU strain HB101. Transformants were selected for resistance to kanamycin. Plasmid DNA from individual transformants was purified and analyzed for increased size due to CLP multiple DNA insertion. Several clones were obtained ranging in size from from 0.5 kbp to 3.5 kbp. One clone pPT0129, with an insert of approximately 1.1 kbp was chosen for expression and protein analysis.

Analysis

E. coli strain HB101 containing plasmid pPT0190 or pPT0129 were grown as described above. The proteins produced by these cells were analyzed by SDS-PAGE for detection of reactivity to CLP antibodies (see Example 1). In both analyses, a strong reactive band was observed of an apparent molecular weight of 45 kD and 60 kD, respectively.

pPT0190　　　　　　　CLP　　Protein　　　　330 AA　　　MW 29,000

MDPVVLQRRDWENPGVTQLNRLAAHPPFASDPM
{[GAP (GPP)$_4$]$_2$GPAGPVGSP}$_7$
GAMCAHRYQLSAGRYHYQLVWCQK
(SEQ ID NO:32)

pPT0129　　　　　　　CLP-CB　Protein　　　357 AA　　　MW 47,000

MDPVVLQRRDWENPGVTQLNRLAAHPPFASDPM
{[GAP (GPP)$_4$]$_2$ (GLPGPKGDRGDAGPKGADGSP) GPAGPVGSP}$_5$
GAMCAHRYQLSAGRYHYQLVWCQK
(SEQ ID NO:33)

EXAMPLE 3

TABLE 4

STRUCTURE OF SequenceD 1, 2 & 3

| | |
|---|---|
| SequenceD1 | $(C_2A_{24}C_2)_4$ |
| SequenceD2 | $(C_2A_{12}C_2)_8$ |
| SequenceD3 | $(C_2(AB)_{12}C_2)_4$ | where:

A=GAPGPAGPP (SEQ ID NO:34)
B=GSRGDPGPP (SEQ ID NO:35)
C=GAHGPAGPK (SEQ ID NO:11)

DNA DESIGN

Due to the complexity of the SequenceD polymer structures the design of the gene monomers was as follows:

1. design and synthesis of $C_2$ units (5' and 3')
2. design and synthesis of A units
3. design and synthesis of AB units

PLASMID pPT 0134 CONSTRUCTION

The acceptor vector pPT0134 was designed and constructed specifically to accommodate the construction requirements of the SequenceD polymer genes. This vector contains two recognition sites for FokI REN in its MCS (multiple cloning site).

Two oligonucleotide strands containing these sites were synthesized and purified as described in Example 1.

```
              FokI                              FokI      ScaI
O.A) 5'-GTGCTGCGGATGCTCGAGATGGTGCATGCATGTACATCCGAGTACTTCGAT
O.B) 3'-      ACGCCTACGAGCTCTACCACGTACGTACATGTAGGCTCATGAAGCTA
(SEQ ID NOS: 36 & 37)
```

After annealing, the two oligonucleotide strands were ligated with pSY937 which had been digested with BanI and EcoRV RENs. The product of the ligation mixture was transformed into E. coli and selected on bacterial plates containing the antibiotic chloramphenicol. Plasmid DNA from individual colonies was analyzed on agarose gel electrophoresis after digestion with ScaI and StuI RENs. One plasmid pPT0124 contained the expected DNA fragment.

The new MCS was then moved to plasmid pSY1367. This plasmid is a derivative of pSY1299 (see U.S. Pat. No. 5,243,038). Plasmid pSY1299 was digested with NciI REN and the large DNA fragment was purified by agarose gel electrophoresis and NACS purification. The purified DNA fragment was treated with DNA Polymerase (see Example 1), ligated, then digested with FokI prior to transformation in E- coii strain HB101. Plasmid DNA from single colonies was purified and analyzed by restriction digests. One plasmid, pSY1366, was found to be correct and lacking the only FokI site present in pSY1299.

Two oligonucleotide strands were synthesized and purified as described in Example 1:

```
        (BanII)                    FokI
1.A) 5'-      CTACATGTGTTACACATCCCGTGC
1.B) 3'-CCGAGATGTACACAATGTGTAGGGCACG
(SEQ ID NO: 38 & 39)
```

Oligonucleotide strands 1.A and 1.B were annealed and ligated with the DNA of plasmid pSY1366 which had been digested with BanII and FspI RENs. The products of this ligation reaction were transformed into a []Qi strain HB101. Plasmid DNA from transformed colonies was purified and digested with FokI. Clones which linearized with FokI were sequenced. Plasmid pSY1367 contained the desired MCS sequence and was chosen for subsequent constructions.

Plasmids pPT0124 and pSY1367 were digested with NruI and NcoI and the DNA fragments were purified by agarose gel electrophoresis and NACS purification. The small fragment (approximately 500 bp) from pPT0124 was ligated with the large fragment from pSY1367. The product of the ligation mixture was transformed into a coli. Plasmid DNA from single colonies was purified and analyzed by restriction digests and DNA sequencing. One plasmid, pPT0134, contained the desired sequence and was used as the acceptor vector for the SequenceD constructions.

SYNTHESIS AND ASSEMBLY OF THE C UNITS

Four oligonucleotide strands were synthesized and purified as described in Example 1. Each pair of oligonucleotide strands encodes a $C_2$ unit, either the 5' or 3' $C_2$ unit.

2.A) 5'-GTGCTCACGGCCCAGCAGGTCCGAAGGGCGCGCATGGCCCAGCAGGCCCGAAAGGTGCC

-continued

2.B) 3'-      AGTGCCGGGTCGTCCAGGCTTCCCGCGCGTACCGGGTCGTCCGGGCTTTCCACGGCACG
(SEQ ID NOS: 40 & 41)

2.C) 5'-GTGCCCATGGCCCAGCAGGACCGAAAGGAGCTCACGGTCCGGCAGGTCCGAAAG
2.D) 3'-      GTACCGGGTCGTCCTGGCTTTCCTCGAGTGCCAGGCCGTCCAGGCTTTCCACG
(SEQ ID NOS: 42 & 43)

Oligonucleotide strands 2.A and 2.B were annealed and ligated with the DNA of plasmid pPT0134 which had been digested with FoId REN. The products of this ligation reaction were transformed into E. coli strain HB101. Plasmid DNA from transformed colonies was purified and digested with Sfil. Clones which linearized with Sfil were sequenced. Plasmid pPT0135 contained the desired $C_2$ sequence and was chosen for subsequent constructions.

Strands 2.C and 2.D were annealed, ligated, and transformed as were strands 2.A and 2.B. Plasmid DNA from transformed colonies was purified and digested with Banll REN. Clones which linearized with Banll were sequenced. Plasmids pPT0137 and pPT0138 contained the correct $C_2$ DNA sequence.

Plasmid pPT0135 and pPT0137 were digested with Banl and StuI RENs. The large fragment from pPT0135, containing the $C_2$ (strands A+B), was ligated with the small fragment of pPT0137 containing the $C_2$ fragment (strands C+D). The ligation products were transformed into E. coli strain HB101. Plasmid DNA from transformants was purified and two digestions were performed, Sfil-StuI and Banll-StuI RENs, respectively. Clones that released a DNA fragment of approximately 800 bp in both digestions were sequenced. Plasmid pPT0140 contained the correct $C_2C_2$ sequence, as shown in Table 5, and was used for SequenceD gene monomer constructions.

agarose gel electrophoresis and purified using a NACS column (see Example 1). The DNA fragment was self-ligated and the products of the ligation were ligated with pPT0134 previously digested with FokI REN. The products of the ligation mixture were transformed into E. coli strain HB101. Plasmid DNA from transformants was purified and digested with FokI REN. Clones containing DNA inserts of 162 bp corresponding to $A_6$ were selected for sequence analysis. Plasmid pPT0144 had the expected DNA sequence and was selected for subsequent constructions. Plasmid DNA from pPT0144 was digested with FokI REN and the two DNA fragments generated by the digestion were separated using agarose gel electrophoresis. The smaller DNA fragment was purified using a NACS column (see Example 1). The DNA fragment carrying the $A_6$ coding sequence was ligated with plasmid DNA pPT0140 previously digested with FoId. The products of the ligation were transformed into E. coli strain HB101. Plasmid DNA from individual colonies was analyzed for inserts containing multiple $A_6$ DNA fragments by digestion with FoId. Several size inserts were found ranging from $A_6$ to $A_{24}$. One clone, pPT0147 (shown in Table 6) was identified to contain the desired SequenceD2 gene monomer sequence $C_2A_{12}C_2$ and was used for further constructions.

The clone containing the SequenceD1 gene monomer sequence $C_2A_{24}C_2$ (shown in Table 7), necessary to construct the SequenceD1 polymer gene, was found to be highly

TABLE 5

GGTGCTCACGGCCCAGCAGGTCCGAAGGGCGCGCATGGCCCAGCAGGCCCGAAA
CCAGCAGTGCCGGGTCGTCCAGGCTTCCCGCGCGTACCGGGTCGTCCGGGCTTT
G  A  H  G  P  A  G  P  K  G  A  H  G  P  A  G  P  K

Ban 1
GGTGCCCATGGCCCAGCAGGACCGAAAGGAGCTCACGGTCCGGCAGGTCCGAAA
CCACGGGTACCGGGTCGTCCTGGCTTTCCTCGAGTGCCAGGCCGTCCAGGCTTT
G  A  H  G  P  A  G  P  K  G  A  H  G  P  A  G  P  K
SEQ ID NOS: 44 & 45)

SequenceD 1 and 2 GENE MONOMER CONSTRUCTIONS

Two oligonucleotide strands were synthesized and purified as described in Example 1.

3.A) 5'-GTGCGCCTGGACCGGCTGGTCCACCGGGTGCTCCGGGACCTGCAGGCCCGCCAG
3.B) 3'-      CGGACCTGGCCGACCAGGTGGCCCACGAGGCCCTGGACGTCCGGGCGGTCCACG
(SEQ ID NOS: 46 & 47)

The two oligonucleotide strands encoding $A_2$ (3A & 3B) were annealed and ligated with plasmid DNA pPT0134 previously digested with FokI REN. The products of the ligation mixture were transformed into E. coli strain HB101. Plasmid DNA from transformants was digested with PstI REN and clones that were linearized were sequenced. Plasmid pPT0142 was found to be correct and used for the multimerization of $A_2$ units.

Plasmid DNA from pPT0142 was digested with FokI REN and the fragment containing the $A_2$ unit was isolated by unstable during subsequent passages. This instability was attributed to the high copy number of the acceptor plasmid. For this reason, the gene monomer from this plasmid was recloned into pBR322 (F. Bolivar, et al. (1977) Gene 2:95-113). The plasmid DNA containing the $C_2A_{24}C_2$ gene fragment was isolated from the plasmid by digestion with NruI and EcoRV RENs, agarose gel electrophoresis, and purified on a NACS column. This DNA fragment was ligated with plasmid pBR322 DNA digested with EcoRV and NruI RENs (see agarose ligation in Example 1). The products of this ligation were transformed into E. coli strain HB101 and selected on bacterial plates containing the antibiotic ampicillin at 100 μg/ml. Plasmid DNA from individual colonies was analyzed by agarose gel electrophoresis. Clones containing the insert were further analyzed by digestion with several RENs and one, pPT0153, was chosen for the construction of the SequenceD1 polymer gene. This plasmid was stable.

described in Example 1. By northern blot analysis (see Example 1), the SequenceD specific mRNA from all clones, using as a probe the SequenceD2 monomer sequence, was

TABLE 6

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
 G   A   H   G   P   A   G   P   K   G   A   H   G   P   A   G   P   K

[GGTGCGCCTGGACCGGCTGGTCCACCGGGTGCTCCGGGACCTGCAGGCCCGCCA]
[CCACGCGGACCTGGCCGACCAGGTGGCCCACGAGGCCCTGGACGTCCGGGCGGT]
[ G   A   P   G   P   A   G   P   P   G   A   P   G   P   A   G   P   P ]_6

Ban I
GGTGCCCATGGCCCAGCAGGACCGAAAGGAGCTCACGGTCCGGCAGGTCCGAAA
CCACGGGTACCGGGTCGTCCTGGCTTTCCTCGAGTGCCAGGCCGTCCAGGCTTT
 G   A   H   G   P   A   G   P   K   G   A   H   G   P   A   G   P   K
```

(SEQ ID NOS: 48 & 49)

TABLE 7

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
 G   A   H   G   P   A   G   P   K   G   A   H   G   P   A   G   P   K

[GGTGCGCCTGGACCGGCTGGTCCACCGGGTGCTCCGGGACCTGCAGGCCCGCCA]
[CCACGCGGACCTGGCCGACCAGGTGGCCCACGAGGCCCTGGACGTCCGGGCGGT]
[ G   A   P   G   P   A   G   P   P   G   A   P   G   P   A   G   P   P ]_{12}

Ban I
GGTGCCCATGGCCCAGCAGGACCGAAAGGAGCTCACGGTCCGGCAGGTCCGAAA
CCACGGGTACCGGGTCGTCCTGGCTTTCCTCGAGTGCCAGGCCGTCCAGGCTTT
 G   A   H   G   P   A   G   P   K   G   A   H   G   P   A   G   P   K
```

(SEQ ID NOS: 50 & 51)

Plasmid from DNA pPT0153 was digested with AcyI REN and subsequently with FokI REN. The DNA fragment containing the SequenceD1 gene monomer, 756 bp, was isolated by agarose gel electrophoresis and purified using a NACS column (see Example 1). The monomer gene fragment was ligated with pSY1262 (see U.S. Pat. No. 5,243,038) which had been digested with BanI REN. The ligation product was transformed into E. coli strain HB101 and selected for growth on bacterial plates containing the antibiotic kanamycin. Plasmid DNA from individual colonies was analyzed for inserts containing multiple SequenceD1 monomer fragments by digestion with BamHI and PvuII RENs and electrophoresis on agarose gel. One clone, pPT0164, contained the gene monomer (756 bp); another, pPT0165, a slightly larger fragment (approximately 1200 bp); and a third, pPT0166, a gene dimer (1512 bp).

SequenceD1 PROTEIN EXPRESSION ANALYSIS.

E. coli strain HB101 containing plasmid pPT0164, pPT0165 or pPT0166 was grown as described above. The proteins produced by these cells were analyzed by western blot analysis for novel protein bands which reacted with SequenceD-$C_2A_2$ peptide antisera. A band with an apparent molecular weight of approximately 45 kD was observed in the culture containing the plasmid pPT0164. A band of 68 kD was observed with pPT0165 and a light smear of bands with pPT0166.

Because of the low level of detectable expression in the strain containing pPT0166, the mRNA produced by the SequenceD1 clones was analyzed. mRNA was prepared as shown to be full length and synthesized at approximately the same level regardless of the SequenceD gene size.

SequenceD1 pPT0166 561 Amino Acids MW: 46,409 Dalton
MDPVVLQRRDWENPGVTQLNRLAAHPPFASDPM
[(GAHGPAGPK)$_2$ (GAPGPAGPP)$_{24}$ (GAHGPAGPK)$_2$]$_2$
GAMDPGRYQLSAGRYHYQLVWCQK (SEQ ID NO: 52)

SequenceD2 POLYMER GENE CONSTRUCTION.

Plasmid DNA from pPT0147 was digested with FokI REN and the digestion fragments were separated by agarose gel electrophoresis. The SequenceD2 gene fragment of 432 bp was excised and purified by NACS column (see Example 1). The purified fragment was ligated with pSY1262 which had been digested with BanI REN. The products of this ligation were transformed into E coli strain HB101 and the transformants were selected for growth on bacterial plates containing the antibiotic kanamycin. Plasmid DNA from individual colonies was purified and analyzed for multiple insertions of the SequenceD2 gene monomer fragment. Several clones were obtained ranging in size from 500 to 3,000 bp. See Table 8 for the results.

SequenceD2 PROTEIN EXPRESSION ANALYSTS.

E. coli strain HB101 containing plasmids pPT0155 to pPT0163 were grown as described above. The proteins produced by these cells were analyzed by western blot analysis for a protein band reactive with SequenceD-$C_2A_2$ peptide specific antisera. See Table 8 for the results.

TABLE 8

| SequenceD2 Expression clones | # of repeats | Gene size (in bp) | # of amino acids | Protein band observed (in kD) |
|---|---|---|---|---|
| pPT 155 | 1 | 603 | 201 | no detection |
| pPT 156 | 2 | 1035 | 345 | 40 |
| pPT 157 | 3 | 1467 | 489 | 60 |
| pPT 158 | 4 | 1899 | 633 | 80 |
| pPT 159 | 5 | 2331 | 777 | 100 |
| pPT 160 | 6 | 2763 | 921 | smear |
| pPT 161 | 7 | 3195 | 1065 | no detection |
| pPT 162 | 7+ | 3240 | 1080 | no detection |
| pPT 163 | 7+ | 3420 | 1140 | no detection |

SequenceD2  pPT0159  777 Amino Acids  MW: 64,094 Dalton
MDPVVLQRRDWENPGVTQLNRLAAHPPFASDPM
[(GAHGPAGPK)$_2$ (GAPGPAGPP)$_{12}$ (GAHGPAGPK)$_2$]$_5$
GAMDPGRYQLSAGRYHYQLVWCQK
(SEQ ID NO:53)

SequenceD3 MONOMER CONSTRUCTION.

Four oligonucleotide strands encoding (AB)$_2$ were synthesized and purified as previously described.

4.A) 5'-GTGCTCCGGGACCTGCAGAATATTATTCTAGAGGTGACCCAGGACCGCCTG    -3'
4.B) 3'-        AGGCCCTGGACGTCTTATAATAAGATCTCCACTGGGTCCTGGCGCACCACG-5'
(SEQ ID NOS: 54 & 55)

4.C & 4.D
5'-        GGCCCACCGGGTAGCCGTGGCGATCCGGGACCACCGGGTGCACCTGGCCCAGCGGGTCCGCCTGGAT
3'-ACGTCCGGGTGGCCCATCGGCACCGCTAGGCCCTGGTGGCCCACGTGGACCGGGTCGCCCAGGCGGACCTAGATC
(SEQ ID NOS: 56 & 57)

Oligonucleotide strands 4.A and 4.B were annealed and ligated with the DNA plasmid pPT0134 (see Example 1) which had been digested with Fokl REN. The products of this ligation were transformed into L DQii strain HB101. Plasmid DNA from transformed colonies was purified and digested with Pstl and Stul. Clones containing a fragment of approximately 800 bp were sequenced. Plasmid pPT0139, containing the desired sequence of strands 4.A and 4.B, was chosen for subsequent constructions.

Strands 4.C and 4.D were annealed and ligated with the DNA plasmid pPT0139 which had been previously digested with Xbal and Pstl RENs. The products of this ligation were transformed into , oQli strain HB101. Plasmid DNA from transformed colonies was purified and digested with Ncol and Dralll RENs. Clones containing a DNA fragment corresponding to the combined insertion of strands 4.A and B and 4.C and D were sequenced. Plasmid pPT0143, containing the correct (AB)$_2$ DNA sequence, as shown in Table 9 was chosen for further constructions.

Plasmid DNA from pPT0143 was digested with Fokl REN and the fragment containing the (AB)$_2$ gene fragment was isolated by agarose gel electrophoresis and purified on a NACS column. The DNA fragment was then ligated with pPT0134 that had been digested with Fokl REN. The products of the ligation were transformed into E. coli strain HB101 and selected for growth on bacterial plates containing the antibiotic chloramphenicol. Plasmid DNA from individual colonies was analyzed for inserts containing multiple (AB)2 DNA fragments by digestion with Fokl REN. Several clones were obtained ranging from one copy to several copies of (AB)$_2$. One clone, pPT0169, containing (AB)$_6$ was used as an intermediate for the construction of the SequenceD3 gene monomer.

The (AB)$_6$ gene fragment was purified from pPT0169 by digestion with Fokl REN, agarose gel electrophoresis and NACS purification. This DNA fragment was then ligated with DNA plasmid pPT0140 that had been previously digested with Banl REN. The products of the ligation were transformed into E. coli strain HB101, and transformants were selected on bacterial plates containing the antibiotic chloramphenicol. Plasmid DNA from individual colonies was analyzed by digestion with Fold REN for inserts containing multiple copies of the (AB)$_6$ gene fragment. One clone, pPT0171, containing C$_2$(AB)$_{12}$C$_2$ (shown in Table 10) was chosen as the SequenceD3 gene monomer for subsequent constructions.

TABLE 9

GGTGCTCCGGGACCTGCAGGCCCACCGGGTAGCCGTGGCGATCCGGGACCACCG
CCACGAGGCCCTGGACGTCCGGGTGGCCCATCGGCACCGCTAGGCCCTGGTGGC
  G   A   P   G   P   A   G   P   P   G   S   R   G   D   P   G   P   P

Xba I
GGTGCACCTGGCCCAGCGGGTCCGCCTGGATCTAGAGGTGACCCAGGACCGCCT
CCACGTGGACCGGGTCGCCCAGGCGGACCTAGATCTCCACTGGGTCCTGGCGGA
  G   A   P   G   P   A   G   P   P   G   S   R   G   D   P   G   P   P
(SEQ ID NO: 58 & 59)

TABLE 10

```
GGTGCTCACGGCCCAGCAGGTCCGAAGGGCGCGCATGGCCCAGCAGGCCCGAAA
CCACGAGTGCCGGGTCGTCCAGGCTTCCCGCGCGTACCGGGTCGTCCGGGCTTT
 G   A   H   G   P   A   G   P   K   G   A   H   G   P   A   G   P   K
```

```
⎡ GGTGCTCCGGGACCTGCAGGCCCACCGGGTAGCCGTGGCGATCCGGGACCACCG
⎢ CCACGAGGCCCTGGACGTCCGGGTGGCCCATCGGCACCGCTAGGCCCTGGTGGC
⎣  G   A   P   G   P   A   G   P   P   G   S   R   G   D   P   G   P   P
```

```
                                          Xba I
GGTGCACCTGGCCCAGCGGGTCCGCCTGGATCTAGAGGTGACCCAGGACCGCCT    ⎤
CCACGTGGACCGGGTCGCCCAGGCGGACCTAGATCTCCACTGGGTCCTGGCGGA    ⎥
 G   A   P   G   P   A   G   P   P   G   S   R   G   D   P   G   P   P  ⎦₆
```

Ban I
```
GGTGCCCATGGCCCAGCAGGACCGAAAGGAGCTCACGGTCCGGCAGGTCCGAAA
CCACGGGTACCGGGTCGTCCTGGCTTTCCTCGAGTGCCAGGCCGTCCAGGCTTT
 G   A   H   G   P   A   G   P   K   G   A   H   G   P   A   G   P   K
```

(SEQ ID NOS: 60 & 61)

SequenceD3 POLYMER GENE CONSTRUCTION.

Plasmid DNA from pPT0171 was digested with FokI REN and the fragment containing the SequenceD3 gene monomer purified by agarose gel electrophoresis and NACS purification. The SequenceD3 monomer was then self-ligated and then ligated with DNA plasmid pSY1262 that had been digested with BanI REN. The products of the ligation were transformed into E. coli strain HB101 and selected for growth on bacterial plates containing the antibiotic kanamycin. Plasmid DNA from individual colonies was purified and analyzed after digestion with XcmI and PvuII RENs for insertions containing multiple copies of the SequenceD3 gene monomer fragment. Clones pPT0173, pPT0174, pPT0175 and pPT0176 containing monomer, dimer, trimer and tetramer forms of SequenceD3, respectively, were selected for expression analysis.

lSequence3 PROTEIN EXPRESSION ANALYSIS.

E. coli strain HB101 containing SequenceD3 plasmids pPT0173, pPT0174, pPT0175, or pPT0176 were grown as described above. The proteins produced by these cells were analyzed by western blot analysis for novel protein bands reactive with SequenceD-(AB)$_2$ peptide specific antisera. Reactive bands were observed with each clone (see Table 11 for results). However, the expression of the full length polymer decreased with the increased size of the genes. Northern analysis using the SequenceD3 monomer as a probe showed that the synthesis of full length mRNA in these clones was at equivalent levels.

TABLE 11

| SequenceD3 Expression clones | # of repeats | Gene size (in bp) | # of amino acids | Protein band observed (in kD) |
|---|---|---|---|---|
| pPT0173 | 1 | 927 | 309 | 28 |
| pPT0174 | 2 | 1683 | 561 | 64 |
| pPT0175 | 3 | 2439 | 813 | 98 |
| pPT0176 | 4 | 3195 | 1065 | 135 |

SequenceD3   pPT0176   1065 Amino Acids   MW: 91,966 Dalton
MDPVVLQRRDWENPGVTQLNRLAAHPPFASDPM
{(GAHGPAGPK)$_2$[(GAPGPAGPP)(GSRGDPGPP)]$_{12}$(GAHGPAGPK)$_2$}$_4$
GAMDPGRYQLSAGRYHQLVWCQK
(SEQ ID NO:62)

EXAMPLE 4

TABLE 12

| STRUCTURE SequenceD 4, 5 & 6 | |
|---|---|
| SequenceD4 | [C$_2$(DB)$_{12}$C$_2$]$_4$ |
| SequenceD5 | [C$_2$(DB)$_6$C$_2$]$_4$ |
| SequenceD6 | [C$_2$D$_{24}$C$_2$]$_4$ | where:

B=GSRGDPGPP (SEQ ID NO:35)

C=GAHGPAGPK (SEQ ID NO:11)

D=GAQGPAGPG (SEQ ID NO:63)

SequenceD4 AND 5 GENE MONOMER CONSTRUCTIONS.

Three double stranded DNA sections, coding for (DB)$_3$, were synthesized, purified and annealed as described in Example 1.

Eco0109I
5.A) 5'-GTGCACAGGGACCGGCGGGACCAGGTGGCTCTGAGGCGATCCGGGTCCTCCGG

-continued
5.B) 3'-    TGTCCCTGGCCGCCCTGGTCCACCGAGAGCTCCGCTAGGCCCAGGAGGCCCACG
(SEQ ID NOS: 64 & 65)

Eco0109I              Dra111
5.C) 5'-GTGCACAAGGACCGGCAGGCCCTGGTGGCAGCCGCGGTGATCCGGGCCCACCGG
5.D) 3'-    TGTTCCTGGCCGTCCGGGACCACCGTCGGCGCCACTAGGCCCGGGTGGCCCACG
(SEQ ID NOS: 66 & 67)

5.E) 5'-GTGCTCAAGGACCGGCTGGCCCAGGCGGTTCCCGTGGAGACCCGGGTCCACCGG
5.F) 3'-    AGTTCCTGGCCGACCGGGTCCGCCAAGGGCACCTCTGGGCCCAGGTGGCCCACG
(SEQ ID NO: 68 & 69)

The three DNA sections were cloned separately. The first two strand section (5.A & 5.B) was ligated to pPT0138 previously digested with Banl REN. The ligation products were transformed into E. coli strain HB101 and selected for growth on bacterial plates containing the antibiotic chloramphenicol. Plasmid DNA from individual colonies was digested with EcoO109I and Stul RENs and analyzed by agarose gel electrophoresis. Plasmid DNA containing an appropriately sized DNA fragment was sequenced and one clone, pPT0221, was used in subsequent constructions.

The second pair of oligonucleotide strands (5.C & 5.D) were ligated with pPT0134 which had been digested with Fokl REN. After transformation of E. coli, plasmid DNA from individual colonies was analyzed by digestion with Banll and Stul RENs. DNAs that were digested by both enzymes were sequenced. One clone, pPT0222, had the expected sequence and was used for subsequent constructions.

Plasmid DNA from pPT0222 was digested with Fokl REN and the fragment (54 bp) containing the second pair of oligonucleotide strands (5C & SD) was isolated by agarose gel electrophoresis followed by NACS purification. This DNA fragment was ligated with pPT0221 previously digested with Banl REN. The products of the ligation were transformed into E. coli and plasmid DNA from single colonies was analyzed by agarose gel electrophoresis after digestion with Dralll and Stul RENs. One clone, pPT0223, was chosen, after DNA sequencing, to be the acceptor vector for the third synthesized SequenceD gene fragment.

Plasmid pPT0223 was digested with Banl REN and ligated with the third pair of oligonucleotides (5.E & 5.F). The product of the ligation reactions was transformed into E. coli strain HB101 and selected for growth on bacterial plates containing the antibiotic chloramphenicol. Plasmid DNA from individual transformants was purified and digested with Fokl and Banl RENs. Clones containing the correct fragment size were sequenced. One clone, pPT0224, shown in Table 13 containing the desired sequence was used in the subsequent constructions of the SequenceD4 and SequenceD5 monomers.

Plasmid DNA from pPT0224 was digested with Fokl and Banl RENs and the digestion fragment carrying $(DB)_3$ was isolated by agarose gel electrophoresis and purified on a NACS column. The purified fragment was self-ligated and then cloned into pPT0140 which had been digested with Banl REN. The products of the ligation were transformed into E. coli strain HB 101. Plasmid DNA from individual colonies was analyzed for inserts containing multiple $(DB)_3$ DNA fragments by digestion with Fokl. Several size inserts were found ranging from $(DB)_3$ to $(DB)_2$. One clone, pPT0229, was identified to contain the desired SequenceD5 monomer sequence, $C_2(DB)_6C_2$, and was used for subsequent constructions. The clone containing the SequenceD4 gene monomer sequence $C_2(DB)_{12}C_2$ was found to be highly unstable during subsequent passages, as was observed during the construction of SequenceDl. Subsequently, a new plasmid was constructed to use as an acceptor for the SequenceD4 gene monomer fragment.

Plasmid pACYC 184 (Chang and Cohen, *J. Bacteriol.* 134, 1141-1156 [1977]) was digested with Banl REN, purified by agarose gel electrophoresis, and the DNA fragment corresponding to approximately 2000 bp was further purified using a NACS column. This DNA fragment was filled in using DNA polymerase (see Example 1) and then self-ligated. The products of the ligation mixture were transformed into E. coli strain HB101 and selected on bacterial plates containing chloramphenicol at 30 ,g/ml. Plasmid DNA from individual colonies was lineazed by digestion with Eco47II. One clone, pPT0235, was used as the acceptor vector for the SequenceD4 monomer.

The plasmid DNA containing the SequenceD4 gene monomer fragment was isolated from the plasmid by digestion with Dral and PvuII RENs, followed by agarose gel electrophoresis. The agarose slice containing the SequenceD4 gene monomer fragment was ligated with plasmid pPT0235 previously digested with Eco47IH REN, and purified by agarose gel electrophoresis and NACS column. The products of this ligation were transformed into E. coli strain HB101 and selected on bacterial plates containing chloramphenicol at 30 µg/ml. Plasmid DNA from individual colonies was analyzed by digestion with NruI and

TABLE 13

```
GGTGCACAGGGACCGGCGGGACCAGGTGGCTCTCGAGGCGATCCGGGTCCTCCG
CCACGTGTCCCTGGCCGCCCTGGTCCACCGAGAGCTCCGCTAGGCCCAGGAGGC
 G  A  Q  G  P  A  G  P  G  G  S  R  G  D  P  G  P  P

GGTGCACAAGGACCGGCAGGCCCTGGTGGCAGCCGCGGTGATCCGGGCCCACCG
CCACGTGTTCCTGGCCGTCCGGGACCACCGTCGGCGCCACTAGGCCCGGGTGGC
 G  A  Q  G  P  A  G  P  G  G  S  R  G  D  P  G  P  P

GGTGCTCAAGGACCGGCTGGCCCAGGCGGTTCCCGTGGAGACCCGGGTCCACCG
CCACGAGTTCCTGGCCGACCGGGTCCGCCAAGGGCACCTCTGGGCCCAGGTGGC
 G  A  Q  G  P  A  G  P  G  G  S  R  G  D  P  G  P  P
(SEQ ID NOS: 70 & 71)
```

EcoRV RENs. One clone containing the SequenceD4 gene monomer fragment, pPTO237, was chosen for the construction of the SequenceD4 polymer gene. This plasmid was stably maintained in E. coli.

SequenceD4 POLYMER GENE CONSTRUCTION.

Plasmid DNA from pPT0237 was digested with Fokl REN. The DNA fragment containing the SequenceD4 gene monomer was isolated by agarose gel electrophoresis and purified using a NACS column (see Example 1). The monomer gene fragment was then ligated with pSY1262 which had been previously digested with Bani REN, treated with phosphatase, and purified by gel electrophoresis and NACS column. The ligation products were transformed into E. coli strain HB101 and the transformants were selected for growth on bacterial plates containing the antibiotic kanamycin at 50 ,g/ml. Plasmid DNA from individual colonies was purified and analyzed for multiple insertion of the SequenceD4 gene monomer fragment. Several clones were obtained containing one, two or four copies of the SequenceD4 gene monomer. Plasmids pPT0247, pPT0248, and pPT0249 containing respectively 1, 2, and 4 copies of the gene monomer, were selected for protein expression analysis.

SequenceD4 PROTEIN EXPRESSION ANALYSIS.

E. coli strain HB101 containing plasmids pPT0247, pPT0248, and pPT0249 were grown as described above. The proteins produced by these cells were analyzed by western blot analysis for novel protein bands reactive with SequenceD-$C_2A_2$ peptide specific antisera. A reactive band corresponding to full length product was observed with each clone.

SequenceD4 pPT0249 1065 Amino Acids MW: 91,533 Dalton
MDPVVLQRRDWENPGVTQLNRLAAHPPFASDPM
$\{(GAHGPAGPK)_2\ [(GAQGPAGPG)\ (GSRGDPGPP)]_{12}\ (GAHGPAGPK)_2\}_4$
GAMDPGRYQLSAGRYHYQLVWCCK
(SEQ ID NO: 72)

SequenceD5 POLYMER GENE CONSTRUCTION.

Plasmid DNA from pPT0229 containing the SequenceD5 gene monomer was isolated after digestion with Fold REN by agarose gel electrophoresis followed by NACS purification. The gene fragment was ligated with pSY1262 which had been digested with Banl REN. The products of the ligation were transformed into E. coli strain HB101 and selected for growth on bacterial plates containing the antibiotic kanamycin at 50 $\mu$g/ml. Plasmid DNA from individual colonies was purified and analyzed for inserts containing multiple copies of the SequenceD5 gene monomer sequence $C_2(DB)_6C_2$. Plasmids pPT0231 and pPT0232, respectively, contained three and four copies of the SequenceD5 gene monomer and were used for expression analysis.

SequenceD5 PROTEIN EXPRESSION ANALYSIS.

E. coli strain HB101 containing plasmids pPT0231 and pPT0232 were grown as described above. The proteins produced by these cells were analyzed by western blot analysis for novel protein bands reactive with SequenceD-$C_2A_2$ peptide specific antisera. A reactive band corresponding to full length product was observed with each clone.

SequenceD5 pPT0232 633 Amino Acids MW: 55,228 Daltons
MDPVVLQRRDWENPGVTQLNRLAAHPPFASDPM
$\{(GAHGPAGPK)_2\ [(GAQGPAGPG)\ (GSRGDPGPP)]_6\ (GAHGPAGPK)_2\}_4$
GAMDPGRYQLSAGRYHYQLVWCQK
(SEQ ID NO: 73)

SequenceD6 GENE MONOMER CONSTRUCTION.

Four oligonucleotide strands encoding $D_4$, were synthesized, purified and annealed as described in Example 1.

```
                                                              Eco0109I
6.A) 5' - GTGCACAGGGACCGGCGGGTCCAGGCGGTGCTCAAGGACCGGCAGGCCCTTAATTAAG
6.B) 3' -          TGTCCCTGGCCGCCCAGGTCCGCCACGAGTTCCTGGCCGTCCGGGAATTAATTCCACG
(SEQ ID NOS: 74 & 75 )

(Eco0109I)
6.C) 5' - GCCCTGGTGGCGCTCAAGGTCCGGCTGGCCCAGGAGGCGCGCAGGGTCCGGCAGGTCCGGGAG
6.D) 3' -        GACCACCGCGAGTTCCAGGCCGACCGGGTCCTCCGCGCGTCCCAGGCCGTCCAGGCCCTCCACG
(SEQ ID NOS: 76 & 77)
```

The first oligonucleotide segment consisting of strands 6.A and 6.B was ligated to pPT0138 previously digested with Banl REN. The ligation products were transformed into E. coli strain HB101 and selected for growth on bacterial plates containing the antibiotic chloramphenicol. Plasmid DNA from individual colonies was digested with EcoOl09I and Xmnl RENs and analyzed by agarose gel electrophoresis. Plasmid DNA containing the correct sized fragment was sequenced and one clone, pPT0219, containing the correct sequence was used for subsequent constructions.

Plasmid pPT0219 was digested with Banl and EcoO109I RENs and ligated with the second pair of oligonucleotides (6.C and 6.D). The products of the ligation were transformed into E. coli strain HB101 and selected for growth on bacterial plates containing the antibiotic chloramphenicol.

Plasmid DNA from transformants was purified and digested with FokI and BanI RENs. Clones containing the correct fragment size were sequenced. One clone, pPT0220, containing the sequence shown in Table 14 was used in subsequent constructions of the SequenceD6 gene monomer.

```
GGTGCACAGGGACCGGCGGGTCCAGGCGGTGCTCAAGGACCGGCAGGCCCTGGT
CCACGTGTCCCTGGCCGCCCAGGTCCGCCACGAGTTCCTGGCCGTCCGGGACCA
 G   A   Q   G   P   A   G   P   G   G   A   Q   G   P   A   G   P   G

GGCGCTCAAGGTCCGGCTGGCCCAGGAGGCGCGCAGGGTCCGGCAGGTCCGGGA
CCGCGAGTTCCAGGCCGACCGGGTCCTCCGCGCGTCCCAGGCCGTCCAGGCCCT
 G   A   Q   G   P   A   G   P   G   G   A   Q   G   P   A   G   P   G
(SEQ ID NOS: 78 & 79)
```

Plasmid DNA containing the $D_4$ sequence was digested with FokI and BanI RENs and the digestion fragment containing $D_4$ was isolated by agarose gel electrophoresis followed by NACS purification. The purified fragment was self-ligated and subsequently ligated with DNA plasmid pPT0140 digested with BanI REN. The ligation products were transformed into E coli strain HB 101 and selected for growth on bacterial plates containing the antibiotic chloramphenicol. A transformant, pPT0242, containing the SequenceD6 gene monomer ((D4)6 flanked by $C_2$–C2) was used for subsequent constructions.

SequenceD6 POLYMER GENE CONSTRUCTION.

Plasmid DNA from pPT0242 was digested with FokI REN. The DNA fragment containing the SequenceD6 gene monomer was isolated by agarose gel electrophoresis and purified using a NACS column. The monomer gene fragment was then ligated with pSY1262 which had been previously digested with BanI REN, treated with phosphatase, and purified by gel electrophoresis and NACS column. The ligation products were transformed into E coli strain HB 101 and the transformants were selected for growth on bacterial plates containing the antibiotic kanamycin at 50 μg/ml. Plasmid DNA from individual colonies was purified and analyzed for multiple insertion of the SequenceD6 gene monomer sequence, $C_2D_{24}C_2$. Several clones were obtained ranging from one to four repeats of the SequenceD6 gene monomer. Plasmids pPT0243, pPT0244, pPT0245, and pPT0246 containing respectively 1, 2, 3, and 4 repeats of the gene monomer were selected for protein expression analysis.

SequenceD6 PROTEIN EXPRESSION ANALYSIS.

E. coli strain B1101 containing plasmids pPT0243 to pPT0246 were grown as described above. The proteins produced by these cells were analyzed by western blot analysis for novel protein bands reactive with SequenceD-$C_2A_2$ peptide specific antisera. See Table 15 for the results.

TABLE 15

| SequenceD6 Expression clones | # of repeats | Gene size (in bp) | # of amino acids | Protein band observed (in kD) |
|---|---|---|---|---|
| pPT0243 | 1 | 927 | 309 | no detection |
| pPT0244 | 2 | 1683 | 561 | 72 |

TABLE 15-continued

| SequenceD6 Expression clones | # of repeats | Gene size (in bp) | # of amino acids | Protein band observed (in kD) |
|---|---|---|---|---|
| pPT0245 | 3 | 2439 | 813 | 110 |
| pPT0246 | 4 | 3195 | 1065 | 140 |

SequenceD6   pPT0246   1,065 Amino Acids   MW: 85,386 Dalton
MDPVVLQRRDWENPGVTQLNRLAAHPPFASDPM
[(GAHGPAGPK)$_2$ (GAQGPAGPG)$_{24}$ (GAHGPAGPK)$_2$]$_4$
GAMDPGRYQLSAGRYHYQLVWCCK
(SEQ ID NO:80)

PROPERTIES OF PURIFIED SeQuenceD6.

The protein polymer, SequenceD6, was purified in multigram quantities as produced from E. coli strain pPT0246 using standard protein purification, extraction, and separation methods. The lyophilized product was a white, spongy material. By amino acid compositional analysis, the product was shown to consist primarily of the amino acids glycine, alanine, proline and glutamine. The molar % glycine+alanine+proline out of the total amino acids were 82.8%. The molar ratio of glycine, alanine, proline, and glutamine was 1.95:0.89:1.00:0.89, respectively. The theoretical ratio of these amino acids for SequenceD6 polymer is 1.90:1.00:1.00:0.43.

The purified product was dried and analyzed for elemental composition. The chemical analysis showed the product to contain 50.5% carbon, 6.78% hydrogen, 19.5 % nitrogen, 11.3 % water and less than 0.1 % noncombustible ash. Theoretical elemental composition of SequenceD6 is 50.9% carbon, 6.49% hydrogen and 20.2% nitrogen. These analyses indicate that the dried product consists of approximately 85.7% protein, and that approximately 98.6% of that protein is SequenceD6.

The dried product is extremely soluble in water. 8% weight solutions or greater can be easily produced. At room temperature or above such solutions are viscous but fluid. Upon chilling to 0° C. the solution forms a solid gel which does not flow and is semi-transparent. Upon heating to greater than 28° C., the gel forms a thick solution. This thermoreversible transition between the liquid and gel phases of the polymer solution can occur repeatedly with no apparent physical change in the polymer structure.

PLASMID pPT0285 CONSTRUCN.

Two oligonucleotide strands were synthesized and purified as described in Example 1:

```
         (Eco47III)PmeI           PmlI                                           SnaB1
StuI EcoRV SnaBI           (SnaI)          NruI      BanI          StuI      EcoRV          (SnaI)
1.  5'-     GCTATGTTTAAACCACGTGTTCGCGATCCGGGTGCCGATCCAGGCCTGCGATATCAGTCGTTA
2.  3'-     CGATACAAATTTGGTGCACAAGCGCTAGGCCCACGGCTAGGTCCGGACGCTATAGTCATGCAT
            A   M   F   K   P   R   V   R   D   P   G   A   D   P   G   L   R   Y   Q   Y   V
(SEQ ID NOS: 81 & 82)
```

The two oligonucleotide strands were annealed and ligated with the DNA of plasmid pPT0235 which had been digested with Eco47III and SnaI RENs.

The product of this ligation reaction was transformed into E. coli strain HB101. Plasmid DNA from transformants was purified and digested with EcoRI in combination with Eco47III or SnaI or NruI RENs. Plasmid DNA from two clones that gave the correct digestion pattern was sequenced. One plasmid, designated pPT0285, was found to be correct and chosen for further contstructions.

CLP 3.1 GENE MONOMER CONSTRUCTION.

The CLP 3.1 synthetic gene was assembled from smaller parts. First, four double-stranded sections of DNA were chemically synthesized.

FRAGMENT 1:

```
    BanI                                                      PstI       BanII    BanI
5'- GTGCCCCTGGCGCTCCGGGTTCTCAAGGTGCACCGGGTCTGCAGAAAGGGCTCG
3'-     GGGACCGCGAGGCCCAAGAGTTCCACGTGGCCCAGACGTCTTTCCCGAGCCACG
(SEQ ID NOS: 83 & 84)
```

FRAGMENT 2:

```
    PstI                                                              BanII
5'-     GGGTGCACCGGGAGCGCCAGGTAGCCAGGGTGCACCGGGATTGCAGGGGCT
3'- ACGTCCCACGTGGCCCTCGCGGTCCATCGGTCCCACGTGGCCCTAACGTCCC
(SEQ ID NOS: 85 & 86)
```

FRAGMENT 3:

```
    BanII                                                     DraIII
5'-     CCGGGTGCACCAGGTAGCCAGGGAGCACCGGGTCTGCAAGGAGCACCGG
3'- CCGAGGCCCAGCTGGTCCATCGGTCCCTCGTCCGCCAGACGTTCCTCGTG
(SEQ ID NOS: 87 & 88)
```

FRAGMENT 4:

```
       DraIII           BamHI                            BanI    StuI    EcoRV
5'-    CAAACACCGGGTGCACCGGGATCCCAGGGCGCTCCGGGCCTGCAAGGTGCCAGGCCTCGAT
3'- CCGAGTTTGTGGCCCACGTGGCCCTAGGGTCCCGCGAGGCCCGGACGTTCCACGGTCCGGAGCAT
(SEQ ID NOS: 89 & 90)
```

The two strands of fragment 3 were phosphorylated before annealing using polynucleotide kinase 3'-phosphatase-free (see Example 1). All of the fragments were then individually annealed using the procedure described in Example 1.

Fragment 1, after annealing, was digested with PstI REN; the digestion mixture was treated with a BioSpin column as was the phosphorylated fragment 3 strands. All four fragments were then loaded on a 12% polyacrylamide gel in 0.5×TBE and the bands corresponding to double stranded DNA were identified by UV shadowing, excised from the gel and extracted by the crush and soak procedure (Smith, *Methods in Enzymology*, 65, 371-379 [1980]).

The fragments were then ligated into pPT0285 previously digested with BanI and EcoRV RENs and further purified by NACS column (see Example 1). The product of the ligation reaction was transformed into E. coli strain HB101. Plasmid DNA from transformants was purified and digested with PvuII and SacII; clones containing inserts of the correct size were further analyzed with EcoRI in combination with several restriction endonucleases to determine the presence of unique restriction endonuclease sites prior to sequencing. One clone looked promising and was sequenced. Plasmid pPT0291 contained the sequence shown in Table 16, containing all four fragments, but had a deletion of 17 bases in fragment 3 including the DraII restriction site.

TABLE 16

```
    Ban I                                           Pst I
5'- GGT  GCC  CCT  GGC  GCT  CCG  GGT  TCT  CAA  GGT  GCA  CCG  GGT  CTG  CAG
    CCA  CGG  GGA  CCG  CGA  GGC  CCA  AGA  GTT  CCA  CGT  GGC  CCA  GAC  GTC
    G    A    P    G    A    P    G    S    Q    G    A    P    G    L    Q

GGT  GCA  CCG  GGA  GCG  CCA  GGT  AGC  CAG  GGT  GCA  CCG  GGA  TTG  CAG
    CCA  CGT  GGC  CCT  CGC  GGT  CCA  TCG  GTC  CCA  CGT  GGC  CCT  AAC  GTC
    G    A    P    G    A    P    G    S    Q    G    A    P    G    L    Q
```

TABLE 16-continued

```
  Ban II
GGG GCT CCG GGT GCA CCA GGT AGC CAG GGA GCA CCG GGT
CCC CGA GGC CCA GCT GGT CCA TCG GTC CCT CGT CCG CCA
 G   A   P   G   A   P   G   S   Q   G   A   P   G

Bam HI                              Ban I
GCA CCG GGA TCC CAG GGC GCT CCG GGC CTG CAA GGT GCC
CGT GGC CCT AGG GTC CCG CGA GGC CCG GAC GTT CCA CGG
 A   P   G   S   Q   G   A   P   G   L   Q
   (SEQ ID NOS: 91 & 92)
```

This plasmid was used to construct the CLP 3.1 monomer. Fragment 3 was ligated with fragment 4 using the HCC ligation method, see Example 1. The product of the ligation mixture was electrophoresed in 2% low melting agarose gel and the band corresponding to the ligated product was excised from the gel and ligated with pPT0291 plasmid DNA that had been previously digested with BanII and SnaBI RENs and purified by agarose gel electrophoresis and NACS column.

The product of the ligation reaction was transformed into E. coli strain HB101. Plasmid DNA from transformants was purified and digested with BamHI and EcoRI RENs; clones that showed the correct restriction pattern were further analyzed with BanII or DraIII RENs; three clones containing inserts of the correct size were sequenced. Plasmid pPT0292 contained the desired CLP 3.1 monomer sequence (see Table 17).

due to CLP 3.1 multiple DNA insertion. Several clones were obtained ranging in size from approximately 1.0 kbp to 3.0 kbp. Five clones, pPT0293 to pPT0297, containing respectively 6, 9, 11, 13, and 17 repeats of the gene monomer were selected for protein expression analysis.

CLP 3.1 PROTEIN EXPRESSION ANALYSIS.

Overnight cultures of E. coli strain HB101 containing plasmids pPT0293 to pPT0297 were grown as described above. The proteins produced by these cells were then used to perform dot blot and western blot analysis using CLP 3.1 peptide specific antisera (see Example 1). See Table 18 for the results. For purification and amino acids analysis larger cultures were used.

TABLE 17

```
    Ban I                                   Pst I
5'- GGT GCC CCT GGC GCT CCG GGT TCT CAA GGT GCA CCG GGT CTG CAG
    CCA CGG GGA CCG CGA GGC CCA AGA GTT CCA CGT GGC CCA GAC GTC
     G   A   P   G   A   P   G   S   Q   G   A   P   G   L   Q

GGT GCA CCG GGA GCG CCA GGT AGC CAG GGT GCA CCG GGA TTG CAG
    CCA CGT GGC CCT CGC GGT CCA TCG GTC CCA CGT GGC CCT AAC GTC
     G   A   P   G   A   P   G   S   Q   G   A   P   G   L   Q

Ban II
    GGG GCT CCG GGT GCA CCA GGT AGC CAG GGA GCA CCG GGT CTG CAA
    CCC CGA GGC CCA CGT GGT CCA TCG GTC CCT CGT CCG CCA GAC GTT
     G   A   P   G   A   P   G   S   Q   G   A   P   G   L   Q

Dra III              Bam HI                          Ban I
    GGA GCA CCG GGT GCA CCG GGA TCC CAG GGC GCT CCG GGC CTG CAA GGT GCC
    CCT CGT GGC CCA CGT GGC CCT AGG GTC CCG CGA GGC CCG GAC GTT CCA CGG
     G   A   P   G   A   P   G   S   Q   G   A   P   G   L   Q
(SEQ ID NOS: 93 & 94)
```

CLP 3.1 POLYMER GENE CONSTRUCTION.

Plasmid DNA pSY1262 was digested with BanI REN. The digestion mixture was divided into two aliquots. One was treated with Calf Intestinal Phosphatase and the other was treated with Shrimp Alkaline Phosphatase (SAP), as described in Example 1.

Plasmid DNA from pPT0292 was digested with BanI REN and the digestion fragments were separated by agarose gel electrophoresis. The CLP 3.1 gene fragment, 180 bp, was excised and purified by NACS column (see Example 1) and then ligated with plasmid pSY1262 prepared as described above.

The product of this ligation reaction was transformed into E. coli strain HB101. Transformants were selected for resistance to kanamycin. Plasmid DNA from individual transformants was purified and analyzed for increase size

TABLE 18

| CLP 3.1 Expression clone | # of repeats | Gene size (in bp) | # of AA | Protein bands observed(kD) |
|---|---|---|---|---|
| pPT0293 | 6 | 1251 | 417 | 45 |
| pPT0294 | 9 | 1791 | 597 | 65 |
| pPT0295 | 11 | 2151 | 717 | 75 |
| pPT0296 | 13 | 2511 | 837 | 90 |
| pPT0297 | 17 | 3231 | 1077 | 130 |

E. coli strain HB101 containing plasmids pPT0293 to pPT0297 were grown as described above. The proteins produced by these cells were analyzed by SDS-PAGE for detection of reactivity to CLP 3.1 peptide specific antisera. In every analysis a strong reactive band was observed of an apparent molecular weight from 45 kD to 130 kD respectively.

CLP 3.1     pPT0297     1077 Amino acids   MW: 91,266 Daltons
MDP VVLQR RDWE NP GVTQLN RLAAHPPFASDPM
[ ( G AP GAP GS Q GAPGLQ)₄]₁₇
G AMDP GRYQLS AGRYHYQLWVCQK
(SEQ ID NO: 95)

EXAMPLE 5

CLP3.7 Construction and Expression:

One oligonucleotide strand coding for the CLP 3.7 gene monomer (see Table 19) was synthesized using an Applied Biosystems DNA synthesizer model 381A and a 2000A synthesis column supplied by Glen Research as described in Example 1. After the synthesis, the 226 base DNA fragment was deprotected and cleaved from the column support by treatment in NH₄OH at 55° C. for 6 hrs.

(1 % Tween 20, 10 mM Tris-HCl pH 8.0, 1 mM EDTA). The tube was closed, incubated at 95° C. for 10 min and then cooled to room temperature. 5 µl of lysate was added to 45 µl MasterMix (1×PCR buffer as described previously, 5 U Amplitaq, 200 µM dNTPs) in a 0.5 ml Perkin Elmer thin-walled Gene AmPm reaction tube. Amplification was performed in a Perkin Elmer DNA Thermal cycler model 480 for 30 cycles with the following step cycle of 1 min each: 95° C., 52° C., and 72° C. Aliquots from different reactions were analyzed by agarose gel electrophoresis using 1.5% Low Melting Point agarose in 0.5'TAE buffer. Plasmid DNA from the clones showing the correct size insert was purified and anlyzed by DNA sequencing. Plasmid pPT0310 con-

TABLE 19

5'-ATGGCAGCGAAAGGGGACCGGTGCCCCGGGTACTCCTGGTCCACAAGGTCTGCCGGGAAGCCCAGGG
    GCTCCGGGTACTCCAGGTCCGCAAGGCCTGCCGGGTTCACCGGGTGCTCCGGGAACTCCTGGCCCGC
    AGGGCTTGCCGGGATCCCCAGGTGCACCAGGAACGCCGGGACCTCAGGGTCTTCCGGGTAGCCCTGG
    TGCCTTTCCGCTAAAGTCCTGCCGT        -3'
(SEQ ID NO: 96)

Two additional DNA strands were synthesized to be used as primers for PCR amplification. The synthesis and purification of these DNA primers was performed as described in Example 1. The two strands are:

1. 5'-AAG AAG GAG ATA TCA TAT GGC AGC GAA AGG GGA CC  -3'
2. 5'-CGC AGA TCT TTA AAT TAC GGC AGG ACT TTA GCG GAA A -3'
    (SEQ ID NOS: 97 & 98)

tained the desired CLP 3.7 monomer sequence (see Table 20).

The PCR reaction was performed as described in Example 1.

The DNA was resuspended and digested with BanI REN as described in Example

1. The digested DNA was purified as described in Example 1, and then ligated with pPT0285 previously digested with BanI, treated with SAP, and purified as described in Example 1. The product of the ligation reaction was transformed into E. coli strain HB101. Plasmid DNA from transformants was purified and analyzed as described below. Colonies were picked and transferred onto a plate and into a 0.5 ml microfuge tube containing 50 µl of lysis buffer

TABLE 20

BanI AvaI/SmaI
5'- GGTGCCCCGGGT ACTCCTGGTCCACAAGGTCTGCCGGGAAGCCCA
3'- CCACGGGGCCCATGAGGACCAGGTGTTCCAGACGGCCCTTCGGGT
    G   A   P   G   T   P   G   P   Q   G   L   P   G   S   P

BanII           GsuI            StuI            DraIII
GGGGCTCCGGGTACTCCAGGTCCGCAAGGCCTGCCGGGTTCACCG
CCCCGAGGCCCATGAGGTCCAGGCGTTCCGGACGGCCCAAGTGGC
 G   A   P   G   T   P   G   P   Q   G   L   P   G   S   P

TABLE 20-continued

```
            BglI                        BamHI
GGTGCTCCGGGAACTCCTGGCCCGCAGGGCTTGCCGGGATCCCCA
CCACGAGGCCCTTGAGGACCGGGCGTCCCGAACGGCCCTAGGGGT
 G  A  P  G  T  P  G  P  Q  G  L  P  G  S  P

Eco0109I                        BanI
GGTGCACCAGGAACGCCGGGACCTCAGGGTCTTCCGGGTAGCCCTGGTGCC -3
CCACGTGGTCCTTGCGGCCCTGGAGTCCCAGAAGGCCCATCGGGACCACGG -5'
 G  A  P  G  T  P  G  P  Q  G  L  P  G  S  P  (G A)
   (SEQ ID NOS: 99 & 100)
```

CLP3.7 Polymer Construction.

Plasmid DNA from pPT0310 was digested with BanI REN and the digestion fragments were separated by agarose gel electrophoresis. The CLP 3.7 gene fragment, 180 bp, was excised and purified by NACS column. The purified fragment was ligated with plasmid pSY1262 which had been prepared as follows: pSY1262 plasmid DNA was digested with BanI REN and subsequently treated with Shrimp Alkaline Phosphatase (SAP) as described in Example 1.

The product of this ligation reaction was transformed into E. coli strain HB101. Transformants were selected for resistance to kanamycin. Plasmid DNA from individual transformants was purified and analyzed for increased size due to CLP 3.7 multiple DNA insertion. Several clones were obtained and two of them containing inserts of approximately 1.25 kbp and 2.6 kbp (pPT0314 and pPT0312 respectively) were chosen to be used for expression of CLP 3.7.

CLP 3.7 Analysis.

E. coli strain HB101 containing plasmid pPT0312 or pPT0314 were grown as described in Example 1. The proteins produced by these cells were analyzed by SDS-PAGE for detection of reactivity to CLP antibodies. In every analysis a strong reactive band was observed with an apparent molecular weight of 130 kD and 50 kD respectively.

```
CLP 3.7      pPT0312      837 AA        MW 72,637
MDPVVLQRRDWENPGVTQLNRLAAHPPFASDPM
[(GAPGTPGPQGLPGSP)4]13
GAMDPGRYQLSAGRYHYQLVWCQK
(SEQ ID NO:101)

CLP 3.7      pPT0314      417 AA        MW 37,060
MDPVVLQRRDWENPGVTQLNRLAAHPPFASDPM
[(GAPGTPGPQGLPGSP)4]6
GAMDPGRYQLSAGRYHYQLVWCQK
(SEQ ID NO:102)
```

EXAMPLE 6

Factor XIIIa reactive peptides.

The sequence of fibrin and of the native cross-linking site is known. The bovine milk protein B-casein is a known substrate for factor XIIIa. Peptide blocks which include a factor XIIIa cross-linking site and retain activity towards factor XIIIa were produced. These peptide blocks or similar amino acid sequences were then conjugated to high molecular weight carrier polymers or their design was used in the construction of protein polymers. When a formulation (aqueous and physiological) containing such polymers is mixed with factor XIIIa, it will undergo cross-linking leading to a setting reaction in which the polymer solution will be converted to a stiff gel or clot. The degree and spacing of cross-linking will influence the setting time and mechanical properties and cohesive strength of the gel. When applied on or in a tissue, an adhesive bond will be created both through physical adsorption to the tissue matrix and through covalent bonding to available tissue proteins.

A synthetic peptide was synthesized containing the amino acid sequence VLSLSQSKVLPVPE (SEQ ID NO: 103) (peptide 93.1) corresponding to residues 162-175 of bovine B-casein as published by Dumas, B.R., Brignon, G., Grosclaude, F., Mercier, J.C. (1972) Eur. J. Biochem. 25, 505-514. The peptide was shown to serve as a substrate for factor XIIIa cross-linking using HPLC analysis.

According to the sequence of human fibrin gamma chain (Rixon, M. W., Chung, D. W. and Davie, W. W., Biochemistry 22, 2077-2086, 1985), the carboxyl terminal 17 amino acids (residues 421 to 437, GEGQQHHLGGAKQAGDV (SEQ ID NO: 104) contain the residues glutamine (Q424) and lysine (K432) which participate in the isopeptide bond formed by the transglutaminase activity of factor XIIIa. Contained also within this sequence is a platelet binding activity. This peptide (Peptide 93.3) was synthesized and similarly shown to serve as a substrate for factor XIIIa.

Similar results were obtained with Peptide 93.2 (GEGQQHHLGGARQAGDV)(SEQ ID NO: 105). This sequence corresponds to amino acids 421-437 of human fibrin gamma-A protein except that K432 of the natural sequence has been substituted with arginine (R). This substitution conserves the overall charge of the peptide block while eliminating the primary amino group of lysine which may participate in transglutaminase activity. It retains the reactive glutamine Q424 and the flanking recognition sequences for cross-linking. The K to R substitution prevents factor XIIIa cross-linking the peptide with itself.

An additional amino acid sequence (Peptide 93.4) was designed that lacks the reactive glutamine Q424. Since this sequence block only includes fibrin gamma chain residues 429–437 (GGAKQAGDV)(SEQ ID NO: 106), it can only serve as a lysine donor to factor XIIIa mediated cross-linking.

EXAMPLE 7

Protein Polymer Adhesive Substrates (PPAS).

PPAS polymers were designed to include oligopeptide blocks of human fibrin gamma chain which contain either all or part of the site of factor XIIIa cross-linking. The amino acid sequences of Peptides 93.3, 93.2, and 93.4 were incorporated within a structural backbone consisting of 3 complete repeats of a 15 amino acid peptide block of human collagen type I (GAPGTPGPQGLPGSP,(SEQ ID NO:107) the CLP3.7 monomer repeating amino acid sequence) and designated PPAS1-A, PPAS1-B, and PPAS 1-C, respectively.

A variety of structural backbones can be used in the design of adhesive polymers with the option of changing the physical properties of the polymer chain. The composition of the backbone will effect the solubility of the polymer as well as its rheological properties. CLP (collagen-like protein) polymers are useful in this respect in that they are extremely soluble in water, allowing protein solutions of greater than 10 weight percent to be formed while still maintaining good flow properties. CLP polymers have good adhesion to hydrophilic surfaces such as glass and therefore may adhere well to tissue.

The 17 amino acid fibrin block of Peptide 93.3 was integrated with the CLP3.7 monomer sequence so as to recreate its hydrophobicity and secondary structure environment matching, as closely as possible, that of human fibrin. Although, this 17 amino acid block is the C-terminal sequence of fibrin gamma chain (chain-A), a variant gamma chain (chain-B) exists in the blood which contains an additional 16 amino acids beyond the cross-linking site. Because the gamma-B chain also participates in factor XIIIa cross-linking, it follows that the 17 amino acid sequence block does not have to be C terminal for activity. Thus, it can be expected that protein polymers consisting of tandem repeats of monomer blocks containing the fibrin gamma factor XIIIa cross-linking sequence, will contain multiple, active sites of potential cross-linking. Cross-linking may occur between polymer chains and with neighboring tissue. During normal healing of the wound, the protein based adhesive will be degraded and resorbed using essentially the same mechanisms of proteolysis by which normal blood clots are dissolved. The products of degradation are peptides of essentially human sequence or amino acids which may be reutilized by the body.

PPASI-A gene monomer synthesis and construction.

The PPAS1-A amino acid monomer sequence with the fibrin gamma sequence shown in bold is as follows:

$(GAPGTPGPQGLPGSP)_3$ GAPGTPGEGQQHHLGGAKQAGDVGSP (SEQ ID NO:108)

One oligonucleotide strand (see Table 21) was synthesized as described in Example 1. After the synthesis, the 123 base DNA fragment was deprotected and cleaved from the column support by treatment in ammonium hydroxide at 55° C. for 6 hrs.

TABLE 21

| |
|---|
| 5'-ATGGCAGCGAAAGGGGACCGTGCACCAGGAACGCCGGGAGAAGGTCAACAGCACCATCTTGGTGG |
| AGCGAAACAGGCAGGCGACGTCGGTAGCCCTGGTGCCTTTCCGCTAAAGTCCTGCCGT -3' |
| (SEQ ID NO:109) |

The PCR reaction was then performed as previously described using the same primers as were used in the construction of the CLP3.7 monomer. The amplified DNA was then resuspended and digested with ApaLI and DraI RENs. The digested DNA was then purified using a Probind filter followed by a Bio-Spin column and then ligated with pPT0310 previously digested with ApaLI and EcoRV RENs and purified by NACS column. The products of the ligation reaction were transformed into E. coli strain HB101. Plasmid DNA from transformants was purified and analyzed by digestion using EcoO109, HincII and HindIII RENs. Plasmid DNA from the clones showing the correct size insert was purified and analyzed by DNA sequencing. Plasmid pPT0318 contained the desired PPAS 1-A gene monomer sequence (see Table 22).

TABLE 22

```
     BanI  AvaI/SmaI
5'-  GGTGCCCCGGGTACTCCTGGTCCACAAGGTCTGCCGGGAAGCCCA
3'-  CCACGGGGCCCATGAGGACCAGGTGTTCCAGACGGCCCTTCGGGT
     G  A  P  G  T  P  G  P  Q  G  L  P  G  S  P

BanII          GsuI              StuI          DraIII
     GGGGCTCCGGGTACTCCAGGTCCGCAAGGCCTGCCGGGTTCACCG
```

TABLE 22-continued

```
CCCCGAGGCCCATGAGGTCCAGGCGTTCCGGACGGCCCAAGTGGC
 G  A  P  G  T  P  G  P  Q  G  L  P  G  S  P

BglI                    BamHI
GGTGCTCCGGGAACTCCTGGCCCGCAGGGCTTGCCGGGATCCCCA
CCACGAGGCCCTTGAGGACCGGGCGTCCCGAACGGCCCTAGGGGT
 G  A  P  G  T  P  G  P  Q  G  L  P  G  S  P

GGTGCACCAGGAACGCCGGGAGAAGGTCAACAGCACCATCTTGGT
CCACGTGGTCCTTGCGGCCCTCTTCCAGTTGTCGTGGTAGAACCA
 G  A  P  G  T  P  G  E  G  Q  Q  H  L  G

AstII               BanI
GGAGCGAAACAGGCAGGCGACGTCGGTAGCCCTGGTGCC  -3'
CCTCGCTTTGTCCGTCCGCTGCAGCCATCGGGACCACGG  -5'
 G  A  K  Q  A  G  D  V  G  S  P  (G  A)
(SEQ ID NOS: 110 & 111)
```

Construction of expression plasmid pPT0317.

Plasmid DNA pSY1262 was linearized with PvuII REN, then passed through a Probind filter followed by a Bio-Spin column. The DNA was then treated with SAP and ligated with a DNA fragment from pQE-17 (QIAGEN Catalog #33173 ) prepared as follows. Plasmid DNA pQE-17 was digested with BgIIII and HindIII RENs and the 36 bp fragment (see Table 23) was purified using a Probind filter and then a Bio-Spin column. The DNA was purified further using a Microcon-30 filter and the filtrate containing the 36 bp was kept. The DNA was then treated with DNA Polymerase I and purified through a Probind filter and then a Bio-Spin column.

TABLE 23

5'- GATCTTCGATCTCATCACCATCACCATCACTA
(SEQ ID NO:112)

3'- AAGCTAGAGTAGTGGTAGTGGTAGTGATTCGA
(SEQ ID NO:113)

The products of the ligation reaction were transformed into E. coli strain HB101. Plasmid DNA from transformants was purified and analyzed by digestion using BstYI and Bstl1O71 RENs. Plasmid DNA from the clones showing the correct restriction pattern was purified and analyzed by DNA sequencing. Plasmid pPT0317 contained the desired DNA insert and was used for further DNA manipulations.

PPAS 1-A polymer construction.

Plasmid DNA from pPT0318 was digested with BanI REN and the digestion fragments were separated by agarose gel electrophoresis. The PPAS1-A gene fragment, 213 bp, was excised and purified using the Ultrafree-MC filter. The purified fragment was ligated with plasmid pPT0317 which had been prepared as follows. Plasmid DNA pPT0317 was digested with BanI REN, then passed through a Probind filter and then a Bio-Spin column. The DNA was then treated with SAP.

The products of the ligation reaction were transformed into E. coli strain HB101. Transformants were selected for resistance to kanamycin. Plasmid DNA from individual transformants was purified and analyzed using EcoRI and EcoRV RENs for the presence of PPAS 1-A multimer gene inserts. Several clones were obtained with insert sizes ranging from 200 bp to approximately 4 kb. Several clones containining from 10 to 20 repeats were chosen for use in expression of the PPAS1-A polymer.

PPAS1-A expression analysis.

E. coli strain HB101 containing plasmid pPT0321, pPT0325, pPT0326, or pPT0327 was cultured as previously described. The proteins produced by these cells showed strong reactive bands of apparent molecular weights ranging from 80 kD to 180 kD when analyzed by western blot for reactivity to CLP antibody. One clone, pPT0321, containing 10 repeats of the PPAS1-A monomer was selected for further study.

PPAS1-A    pPT0321    762 AA    MW 68,056

MDPVVLQRRDWENPGVTQLNRLAAHPPFASDPM
[(GAPGTPGPQGLPGSP)₃ GAPGTPGEGQQHHLGGAKQAGDVGSP]₁₀
GAMDPGRYQDLRSHHHHHH
(SEQ ID NO:114)

PPAS 1-B gene monomer synthesis and construction.

The PPAS1-B amino acid monomer sequence with the fibrin gamma sequence shown in bold is as follows:

(GAPGTPGPQGLPGSP)₃ GAPGTPGEGQQHHLGGARQAGDVGSP
(SEQ ID NO:115)

Two oligonucleotide strands (see Table 24) were synthesized and purified as previously described.

TABLE 24

1. 5'    GTGGAGCTCGCCAGGCAGGCGACGT (SEQ ID NO:116)
2. 3' GAAGCACCTCGAGCGGTCCGTCCGC (SEQ ID NO:117)

These oligonucleotide strands were annealed and ligated with plasmid pPT0318 which had been digested with BstXI and AatII RENs. The products of this ligation reaction were transformed into E. coli strain HB101. Plasmid DNA from transformants was purified and digested with NcoI and SacI RENs to determine whether they had the correct restriction pattern. Plasmid DNA from correct clones was sequenced. Plasmid pPT0320 (shown in Table 25) (SEQ ID NOS: 118 & 119) contained the desired PPAS1-B monomer sequence.

TABLE 25

```
     BanI    AvaI/SmaI
5'-  GGTGCCCCGGGTACTCCTGGTCCACAAGGTCTGCCGGGAAGCCCA
3'-  CCACGGGGCCCATGAGGACCAGGTGTTCCAGACGGCCCTTCGGGT
      G  A  P  G  T  P  G  P  Q  G  L  P  G  S  P

BanII        GsuI              StuI           DraIII
     GGGGCTCCGGGTACTCCAGGTCCGCAAGGCCTGCCGGGTTCACCG
     CCCCGAGGCCCATGAGGTCCAGGCGTTCCGGACGGCCCAAGTGGC
      G  A  P  G  T  P  G  P  Q  G  L  P  G  S  P

BglI              BamHI
     GGTGCTCCGGGAACTCCTGGCCCGCAGGGCTTGCCGGGATCCCCA
     CCACGAGGCCCTTGAGGACCGGGCGTCCCGAACGGCCCTAGGGGT
      G  A  P  G  T  P  G  P  Q  G  L  P  G  S  P

GGTGCACCAGGAACGCCGGGAGAAGGTCAACAGCACCATCTTGGT
     CCACGTGGTCCTTGCGGCCCTCTTCCAGTTGTCGTGGTAGAACCA
      G  A  P  G  T  P  G  E  G  Q  Q  H  H  L  G

AatII              BanI
     GGAGCTCGCCAGGCAGGCGACGTCGGTAGCCCTGGTGCC      -3'
     CCTCGAGCGGTCCGTCCGCTGCAGCCATCGGGACCACGG      -5'
      G  A  R  Q  A  G  D  V  G  S  P (G  A)
```

PPAS1-B polymer construction.

Plasmid DNA from pPT0320 was digested with BanI REN and the digestion fragments were separated by agarose gel electrophoresis. The PPAS 1-B gene fragment, 213 bp, was excised and purified using an Ultrafree-MC filter. The purified fragment was ligated with plasmid pPT0317 prepared as described above.

The products of this ligation reaction were transformed into E. coli strain HB101. Transformants were selected for resistance to kanamycin. Plasmid DNA from individual transformants was purified and analyzed using EcoRI and EcoRV RENs for DNA inserts containing multimers of the PPAS1-B gene monomer. Several clones were obtained containing inserts up to 5 kb in size.

PPAS1-B expression analysis.

E. coli strain HB101 containing plasmid pPT0324, containing 10 repeats of the PPAS1-B monomer sequence, was cultured as previously described. The proteins produced by these cells were analysed by western blot for reactivity to CLP antibody. A strong reactive band was observed with an apparent molecular weight of approximately 90 kD.

PPAS1-B    pPT0324    762 AA    MW 68,336

MDPVVLQRRDWENPGVTQLNRLAAHPPFASDPM
[(GAPGTPGPQGLPGSP)$_3$ GAPGTPGEGQQHHLGGARQAGDVGSP]$_{10}$
GAMDPGRYQDLRSHHHHHH
(SEQ ID NO:120)

PPAS1-C gene monomer synthesis and construction.

The PPAS1-C amino acid monomer sequence with the fibrin gamma sequence shown in bold is as follows:

(GAPGTPGPQGLPGSP)$_3$ GAPGTPGGAKQAGDVGSP (SEQ ID NO:121)

Two oligonucleotide strands (see Table 26) were synthesized and purified as previously described.

TABLE 26

```
5'    TGCACCAGGAACGCCGGGAGGTGCTAAACAAGCAGGAGACGTCGGTAGCCCTGGTGCCTTT
3'            GGTCCTTGCGGCCCTCCACGATTTGTTCGTCCTCTGCAGCCATCGGGACCACGGAAA
(SEQ ID NOS: 122 & 123)
```

These oligonucleotide strands were annealed and ligated with plasmid pPT0310 which had been digested with ApaLI and EcoRV RENs. The products of this ligation reaction were transformed into E. coli strain HB101. Plasmid DNA from transformants was purified and digested with BsaHI and HindIII RENs to determine their restriction pattern. Plasmid DNA from correct clones was sequenced. Plasmid pPT0319 (shown in Table 27) (SEQ ID NOS: 124 & 125) contained the desired PPAS1-C gene monomer sequence.

TABLE 27

```
          BanI      AvaI/SmaI
5'-   GGTGCCCCGGGTACTCCTGGTCCACAAGGTCTGCCGGGAAGCCCA
3'-   CCACGGGGCCCATGAGGACCAGGTGTTCCAGACGGCCCTTCGGGT
       G  A  P  G  T  P  G  P  Q  G  L  P  G  S  P

BanII          GsuI              StuI           DraIII
      GGGGCTCCGGGTACTCCAGGTCCGCAAGGCCTGCCGGGTTCACCG
      CCCCGAGGCCCATGAGGTCCAGGCGTTCCGGACGGCCCAAGTGGC
       G  A  P  G  T  P  G  P  Q  G  L  P  G  S  P

BglI              BamHI
      GGTGCTCCGGGAACTCCTGGCCCGCAGGGCTTGCCGGGATCCCCA
      CCACGAGGCCCTTGAGGACCGGGCGTCCCGAACGGCCCTAGGGGT
       G  A  P  G  T  P  G  P  Q  G  L  P  G  S  P

ApaLI
      GGTGCACCAGGAACGCCGGGAGGTGCTAAACAAGCAGGAGACGTC
      CCACGTGGTCCTTGCGGCCCTCCACGATTTGTTCGTCCTCTGCAG
       G  A  P  G  T  P  G  G  A  K  Q  A  G  D  V

BanI
      GGTAGCCCTGGTGCC       -3'
      CCATCGGGACCACGG       -5'
       G  S  P  (G  A)
```

PPAS1-C polymer construction.

Plasmid DNA from pPT0319 was digested with BanI REN and the digestion fragments were separated by agarose gel electrophoresis. The PPAS 1-C gene fragment, 192 bp, was excised and purified using an Ultrafree-MC filter. The purified fragment was ligated with plasmid pPT0317 which had been prepared as described above. The products of this ligation reaction were transformed into E. coli strain HB101. Transformants were selected for resistance to kanamycin. Plasmid DNA from individual transformants was purified and analyzed using EcoRI and EcoRV RENs for DNA inserts containing multimers of PPAS1-C gene monomer. Several clones were obtained and one of them, pPT0322, containining an insert of approximately 2 kb, containing 10 repeats of the PPAS1-C gene monomer, was chosen for expression analysis.

PPAS1-C expression analysis.

E. coli strain HBO1 containing plasmid pPT0322 was cultured as previously described. The proteins produced by these cells were analysed by western blot reactivity with CLP antibody. A strong reactive band was observed with an apparent molecular weight of approximately 80 kD.

One oligonucleotide strand coding for the POLSITE portion of the gene monomer (see Table 28) was synthesized as previously described. After the synthesis, the 126 base DNA strand was deprotected and cleaved from the column support by treatment in ammonium hydroxide at 55° C. for 6 hrs.

PPAS1-C    pPT0322    682 AA    MW 59,192

MDPVVLQRRDWENPGVTQLNRLAAHPPFASDPM
[(GAPGTPGPQGLPGSP)$_3$ GAPGTPGGAKQAGDVGSP]$_{10}$
GAMDPGRYQDLRSHHHHHH
(SEQ ID NO:126)

PPAS1-D gene monomer synthesis and construction.

The PPAS1-D amino acid monomer sequence with the fibrin gamma POLSITE sequence shown in bold is as follows:

(GAPGTPGPQGLPGSP)$_2$ GA TRWYSMKKTTMKIIPFNRLTI GEGQQHHLGGARQAGDV GSP
(SEQ ID NO:127)

TABLE 28

| | |
|---|---|
| 5'- | ATGGCAGCGAAAGGGGACCACCGGGTGCTACCCGTTGGTATTCTATGAAAAAGACTACCATGAA |
| | AATCATTCCGTTTAACCGCCTGACCATTGGCGAAGGTCAACTTTCCGCTAAAGTCCTGCCGT    -3' |
| (SEQ ID NO:128) | |

The PCR reaction was then performed as previously described using the same primers as were used in the construction of the CLP3.7 monomer. The DNA was resuspended and digested with DraIII and HincII RENs and the digested DNA was purified using a Probind filter followed by a Bio-Spin column and then ligated with pPT0320 previously digested with DraIII and HincII RENs and purified with a Probind filter followed by a Bio-Spin column. The products of the ligation reaction were transformed into E. coli strain HB101. Plasmid DNA from transformants was purified and digested with NlaIII and plasmids giving the correct restriction pattern were sequenced. A plasmid containing the desired PPASl-D monomer sequence, pPT0328, (see Table 29) (SEQ ID NOS: 129 & 130) was used for further DNA constructions.

TABLE 29

```
    BanI    AvaI/SmaI
5'- GGTGCCCCGGGTACTCCTGGTCCACAAGGTCTGCCGGGAAGCCCA
3'- CCACGGGGCCCATGAGGACCAGGTGTTCCAGACGGCCCTTCGGGT
    G  A  P  G  T  P  G  P  Q  G  L  P  G  S  P

BanII          GsuI           StuI          DraIII
    GGGGCTCCGGGTACTCCAGGTCCGCAAGGCCTGCCGGGTTCACCG
    CCCCGAGGCCCATGAGGTCCAGGCGTTCCGGACGGCCCAAGTGGC
    G  A  P  G  T  P  G  P  Q  G  L  P  G  S  P

GGTGCTACCCGTTGGTATTCTATGAAAAAGACTACCATGAAAATC
    CCACGATGGGCAACCATAAGATACTTTTTCTGATGGTACTTTTAG
    G  A  T  R  W  Y  S  M  K  K  T  T  M  K  I

HincII
    ATTCCGTTTAACCGCCTGACCATTGGCGAAGGTCAACAGCACCAT
    TAAGGCAAATTGGCGGACTGGTAACCGCTTCCAGTTGTCGTGGTA
    I  P  F  N  R  L  T  I  G  E  G  Q  Q  H  H AatII          BanI
    CTTGGTGGAGCTCGCCAGGCAGGCGACGTCGGTAGCCCTGGTGCC    -3'
    GAACCACCTCGAGCGGTCCGTCCGCTGCAGCCATCGGGACCACGG    -5'
    L  G  G  A  R  Q  A  G  D  V  G  S  P (G  A)
```

PPAS 1-D polymer construction.

ppPT0328 plasmid DNA containing the gene monomer coding for PPAS1-D is digested with BanI REN and the digestion fragments are separated by agarose gel electrophoresis. The PPAS1-D gene fragment, 219 bp, is excised and purified using an Ultrafree-MC filter. The purified fragment is ligated with plasmid pPT0317 prepared as described above. The products of this ligation reaction are transformed into E. coli strain HB101. Transformants are selected for resistance to kanamycin. Plasmid DNA from individual transformants is purified and analyzed using EcoRI and EcoRV RENs for DNA inserts containing multimers of the PPAS 1-D gene monomer. An approriate clone containing a DNA insert from 1 to 4 kb is analyzed for PPAS1-D polymer expression.

PPAS1-D protein polymer sequence:
MDPVVLQRRDWENPGVTQLNRLAAHPPFASDPM
[(GAPGTPGPQGLPGSP)$_2$ GATRWYSMKKTTMKIIPFNRLTIGEGQQHHLGGARQAGDVGSP]$_n$
GAMDPGRYQDLRSHHHHHH
(SEQ ID NO:131)

Where n=2–20

EXAMPLE 8

PPAS1-A Activity Assay.

E. coli strain PPT0321 containing the PPAS1-A polymer gene was produced by fermentation. The product was purified from the cellular biomass by means of cellular lysis, clearance of insoluble debris by centrifugation, and affinity chromatography. The purified product was analyzed by sodium dodecyl sulfate polyacrylamide gel electrophoresis, immunoreactivity with CLP antibody, and amino acid analysis. A protein band of apparent molecular weight 85,000 was observed by amido black staining of SDS-PAGE separated and transferred samples and the same band reacted with the CLP antibody on western blots. As expected, amino acid analysis indicated that the product was enriched for the amino acids glycine (34.3%), alanine (7.3%), proline (28.5%), and glutamine (7.0%). The amino acid composition (see Table 30) shows the correlation between the composition of the purified product and the expected theoretical composition as deduced from the synthetic gene sequence.

TABLE 30

Amino Acid Analysis of Purified PPAS1-A

| Amino Acid | pmoles | ACTUAL % composition | THEORETICAL % composition |
|---|---|---|---|
| Ala | 73.74 | 7.3 | 8.4 |
| Asx | 25.57 | 2.5 | 2.3 |
| Glx | 71.11 | 7.0 | 9.7 |
| Phe | 1.48 | 0.15 | 0.1 |
| Gly | 346.27 | 34.3 | 30.5 |
| His | 31.69 | 3.14 | 3.5 |
| Ile | 0 | 0 | 0 |
| Lys | 9.10 | 0.9 | 1.3 |
| Leu | 46.20 | 4.6 | 5.8 |
| Met | 3.83 | 0.38 | 0.4 |
| Pro | 288.16 | 28.5 | 24.4 |
| Arg | 4.27 | 0.42 | 0.7 |
| Ser | 48.07 | 4.8 | 5.5 |
| Thr | 47.84 | 4.7 | 5.4 |
| Val | 12.61 | 1.3 | 1.7 |
| Tyr | 0 | 0 | 0.1 |

Purified PPAS 1-A was analyzed for its ability to serve as a substrate for the blood Clotting enzyme, factor XIIIa. The data indicated that PPAS1-A serves as a substrate for the blood clotting factor XIIIa. By incorporating the fibrin oligopeptide block containing the active glutamine residue within the PPAS -A chain, synthetic protein substrate for factor XIIIa was created. In the presence of BAPA or other compounds such as proteins which contain a reactive primary amino group equivalent to lysine, factor XIIIa will cause the lige of such compounds with PPAS 1-A. The activity of such polymers and factor XIIIa has utility as an adhesive, sealant, or bonding agent. They may be used in the creation of cross-linked hydrogel materials which can encapsulate live cells, tissues or organs. They may be used to incorporate small molecules or active agents to proteins through nonhydrolyzing but proteolytically susceptible linkages. This chemistry can be used to attach pharmaceuticals to resorbable protein matrices for use in drug delivery.

EXAMPLE 9

Construction of PPAS 1 -F.

Construction of Plasmid pPT0334.

Plasmid DNA pPT0312 was linearized with PvuII REN, then passed through a Millipore Probind f ilter . The DNA was then t reat ed w ith SA P. The linearized pPT0312 DNA was then ligated with a DNA f ragment from pQE-17 as described above.

The products of the ligation reaction were transformed into E. coli strain HB1t1. Plasmid DNA from transformants was purified and analyzed by digestion using Bst1107I and EcoRV RENs. Clones containing the de sired DNA fragment were further digested with Bstl 1071 and BstYI RENs to determine the orientation of the insert. Plasmid DNA from the clones showing the correct restriction pattern was purified and an alyzed by DNA sequencing. Plasmid pPT337 contained the desired DNA insert a nd w as used for further DNA manipulation.

Plasmid DNA pbPT0337 wa s digested with XcmI REN, followed by Mung Bean Nuclease treatment for 30 min. at 37° C. The DNA was then purified using Probind and Biospin and then treated with SAP followed by Probind and Biospin column purification.

The PCR amplified DNA, coding for the PPAS1-A (Table 22), was digested with ApaLI and BglII RENs, the fragments were purified by agarose gel electrophoresis followed by Ultrafree MC gel purification. The DNA was then treated with DNA Polymerase I Klenow fragment and then purified using a Probind column followed by a Biospin column as described previously. The DNA was then ligated with pPT0337.

The products of the ligation reaction were transformed into E coli strain HB101. Plasmid DNA from transformants was purified and analyzed by digestion using EcoRI and DraI RENs. Plasmid pPT0334 contained the desired insert and was used for subsequent constructions.

PPAS1-F Polymer Construction pThe PCR amplified DNA coding for PPAS 1-A was again digested with EcoRV REN, then the enzyme was removed with a Probind column followed by treatment with BsaJI REN, then purified by Probind and Biospin columns and concentrated in vacuo. The DNA was treated with DNA Polymerase Klenow fragment followed by Probind column purification, then the DNA fragments were purified by agarose gel electrophoresis followed by Ultrafree MC gel purification, and then concentrated in vacuo followed by Biospin column purification. The DNA was then ligated with plasmid DNA pPT0334 previously digested with EcoRV REN followed by Probind and Biospin columns and then treated with SAP followed by Probind and Biospin columns.

The products of the ligation reaction were transformed into E.coli strain HB101. Plasmid DNA from transformants was purified and analyzed by digestion using BstXI REN. The clones containing the desired DNA fragment were further digested with AccI and EcoRV RENs to determine the orientation of the insert. Plasmid pPT0338 contained the DNA fragment in the correct orientation and was used for subsequent constructions.

Plasmid DNA pPT0338 was digested with BanI REN and the digestion fragments were separated by agarose gel electrophoresis, the DNA was excised and self-ligated. The products of the ligation mixture were transformed into E coli strain HB101. Plasmid DNA from transformants was purified and analyzed by digestion using BamRI and Bst1107I RENs. Plasmid pPT339 contained the desired deletion and was used for subsequent constructions.

Plasmid DNA pPT0339 was digested with BanI REN, followed by Probind and Biospin columns and then treated with SAP followed by Probind and Biospin columns. The plasmid DNA so treated was ligated with the CLP gene fragments from pPT0312. Plasmid DNA pPT0312 was digested with BanI REN and the CLP gene fragments purified by agarose gel electrophoresis followed by NACS and Biospin columns.

The products of this ligation reaction were transformed into E. coli strain HB101. Transformants were selected for resistance to kanamycin. Plasmid DNA from individual transformants was purified and analyzed for DNA inserts containing multimers of PPAS1-F gene monomers. Several clones were obtained and one of them (pPT0348) containing an insert of approximately 2.2 kb (12 repeats of the CLP 3.7 gene monomer) was chosen for expression analysis.

PPAS1-F Analysis.

An overnight culture of E. coli strain HB101 containing plasmid pPT0348 was grown as previously described. The proteins produced by these cells were analysed by western blot reactivity with anti-CLP antibody. A strong reactive band was observed with an apparent molecular weight of approximately 94 kD. The expected amino acid sequence of the PPAS1-F polymer encoded by plasmid pPT0348 is shown below.

As is evident from the above results, highly repetitive sequences can be prepared, cloned, and used for expression of high molecular weight collagen-like polymers to produce a wide variety of products which may mimic the properties of naturally occurring products, as well as comprise novel properties. In the high molecular weight collagen-like polymers according to the subject invention, specific amino-acid sequences may be made readily available to the environment, while providing for structural or non-structural capabilities such as fiber, film, and membrane formation, emulsions, coatings, etc. The subject high molecular weight collagen like polymer may be comprised of strands which interact to provide for structural characteristics, such as article formation with good mechanical, e.g., tensile properties, while at the same time providing for amino acid sequences which may be used in a wide variety of biological and chemical applications. By designing recombinant synthetic collagen-like polymers to comprise less than 45 number percent prolines, a variety of useful collagen-like polymers may be formed having properties similar to collagen, but enjoying unique characteristics. The products find use as films, fibers, molded objects, admixed with other natural or synthetic polymers or coatings on fibers, films, labware or other surfaces, e.g., prosthetic devices, and the like. The subject compositions may be used for binding a wide variety of specific binding materials, as catalytic substances, where the amino acid sequence may specifically chelate a wide variety of elements, as purification media, as composites, laminates, adhesives, combined with inorganic or organic materials, such as carbon fibers, nylon fibers, nitrocellulose, etc., as flask coatings or in synthetic matrices for the growth and study of cells, as affinity columns, as supports for biological materials, and the like.

All publications and patent applications mentioned in this specification are herein incorporated by reference to the same extent as if each individual publication or patent application was specifically and individually indicated to be incorporated by reference.

PPAS1-F    pPT0348    829 AA    MW 72,437

MDPVVLQRRDWENPGVTQLNRLAAHPPFASDAPGTPGEGQQHHLGGAKQAGDVGSP
[(GAPGTPGPQGLPGSP)$_4$]$_{12}$
GAMDPGRYHMAAKGDRAPGTPGEGQQHHLGGAKQAGDVGSPDQDLRSHHHHHH
(SEQ ID NO:132)

The fibrin gamma chain sequence is shown in bold. PPAS I-F was determined to be a substrate for Factor XIIIa and can be used in crosslinking reactions with suitable amine donors.

The invention now being fully described, it will be apparent to one of ordinary in the art that many changes and modifications can be made thereto without ting from the spirit or scope of the appended claims.

What is claimed is:

1. An unnatural collagen-like polymer of at least about 30 kD, characterized by:
    being capable of being expressed in a unicellular organism from a construct prepared in vitro;
    comprising a major proportion of amino acids present as triads having glycine as the first amino acid and at least 40 number % of said triads comprising at least one proline, wherein the total proline content of said triads is less than 45 number %; and
    comprising at least two repetitive units of (glyXO), wherein X and O are the same or different in each triad and symbolize individual amino acids and n is at least 4.

2. A collagen-like polymer according to claim 1, wherein at least two triads are triads found in naturally occurring collagens.

3. A collagen-like polymer according to claim 1, wherein said polymer is not more than about 100 kD and at least 10 number % of the amino acids of said triads are proline.

4. A collagen-like polymer according to claim 1, wherein X and 0 are selected from the group consisting of alanine, isoleucine, valine, leucine, serine, threonine, asparagine, glutamine, lysine, arginine, aspartic acid, glutamic acid, histidine and proline.

5. A collagen-like polymer according to claim 1, wherein the number of triads comprising proline is at least 60 number %.

6. An unnatural collagen-like polymer of at least about 30 kD, having a repeating sequence of triads, wherein each of said triads has glycine as the first amino acid and comprising at least one repeat of a sequence of the following formula:

$$((glyXO)_n \Omega)_m$$

wherein:
    said polymer is capable of being expressed in a unicellular organism from a construct prepared in vitro;
    X and O are any amino acids, except that X and O are selected to provide a total proline content of the triads of at least about 10 and less than about 45 % by number;
    $\Omega$ has from 0 to 50 amino acids and is other than a repetitive glyXO motif;
    n is in the rage of 4 to 1 00; and
    m is at least one.

7. A collagen-like polymer according to claim 6, wherein X and 0 are selected from the group consisting of alanine, isoleucine, leucine, valine, serine, threonine, asparagine, glutamine, lysine, arginine, aspartic acid, glutamic acid, histidine and proline.

8. A collagen-like polymer according to claim 6, wherein at least one of said triads comprises alanine.

9. A collagen-like polymer according to claim 6, wherein at least one glyXO consists of gly-ala-pro, gly-ala-his, gly-pro-ala, gly-pro-pro, gly-ala-ser, or gly-asp-pro.

10. A collagen-like polymer according to claim 8, wherein at least about 40 number % of said triads comprise proline.

11. An unnatural collagen-like polymer of at least about 30 kD, wherein the total proline content of said polymer is less than 45 number %, of the formula:

$$J^1{}_r((((glyU^u\pi^H)_{p2}(glyX^{xol\ Oo})_{n1}(glyU^u\pi^H)_{p2})\Omega_1)_{m1})J^2,$$

wherein:
    said polymer is capable of being expressed in a unicellular organism from a construct prepared in vitro;
    $J^1$ and $J^2$ are the same or different and are amino acid sequences of from about 1 to 50 amino acids;
    X and O are any amino acids except that X and O are selected to provide a polymer having a proline content of less than about 45 number %;
    $\Omega$ is an amino acid sequence of 0 to 50 amino acids;
    x and o indicate the X and 0 in each triad may be the same or different;

n indicates that the amino acid sequence in each Q may be the same or different;

U and π are any amino acids;

u and π indicate the same or different amino acids in the individual triads;

nphu 1is in the range of about 4 to 75;

the r's are the same or different and are 0 or 1;

p2 is in the range of 0 to 6; and $m^1$ is in the range of about 1 to 20.

12. A collagen-like polymer according to claim 11, wherein at least one triad consists of gly-ala-pro, gly-pro-ala, gly-pro-pro, gly-ala-ser, gly-pro-ser, gly-ala-gln, gly-ser-pro, gly-pro-arg, gly-ala-lys, gly-ala-arg, gly-glu-arg, gly-asp-arg, gly-glu-pro, gly-asp-ala or gly-glu-ala.

13. A collagen like polymer according to claim 11, wherein said polymer comprises at least 40 number % of triads comprising proline.

14. A collagen-like polymer according to claim 11, wherein U and II are selected from the group consisting of alanine, isoleucine, leucine, valine, serine, threonine, asparagine, glutamine, lysine, arginine, aspartic acid, glutamic acid, histidine and proline.

15. A collagen-like polymer according to claim 12, wherein the number of triads comprising proline is at least 40 number %.

16. An unnatural collagen-like polymer of at least about 30 kD, characterized by:
    being capable of being expressed in a unicellular organism from a construct prepared in vitro;
    comprising a major proportion of amino acids present as triads having glycine as the first amino acid and at least 40 number % of said triads comprising at least one proline, wherein the total proline content of said triads is less than 45 number %; and
    comprising at least two repetitive units of the formula $\alpha_2\beta_3\alpha_2$, wherein α has three triads characterized as having glycine as the first amino acid and at least two of the three triads having proline; β has from three to nine triads, wherein at least 30% of the triads have proline; and e is at least 6 and not more than about 36.

17. A collagen-like polymer according to claim 16, wherein a comprises at least one of gly-pro-ala and gly-pro-lys, and β comprises at least two of gly-ala-pro, gly-pro-ala, gly-pro-pro, gly-pro-gly, gly-ala-ser or gly-asp-pro.

18. A collagen-like polymer according to claim 17, wherein β comprises GAPGPAGPP (SEQ ID NO: 133), GAPGPAGPPGSRGDPGPP (SEQ ID NO: 134), GAQG-PAGPGGSRGDPGPP (SEQ ID NO: 135), or GAQG-PAGPG (SEQ ID NO: 10).

19. A collagen like polymer according to claim 16, wherein said polymer comprises at least four repetitive units.

20. A DNA sequence encoding a collagen like polymer according to claim 1.

21. A DNA sequence encoding a collagen like polymer according to claim 6.

22. A DNA sequence encoding a collagen like polymer according to claim 11.

23. A DNA sequence encoding a collagen like polymer according to claim 16.

24. A unicellular microorganism comprising a DNA sequence encoding an unnatural collagen-like polymer of at least about 30 kD, characterized by comprising a major proportion of amino acids present as triads having glycine as the first amino acid and at least 40 number % of said triads comprising at least one proline, wherein the total proline content of said triads is less than 45 number %; and comprising at least two repetitive units of $(glyXO)_n$, wherein X and O are the same or different in each triad and symbolize individual amino acids and n is at least 4.

25. A DNA sequence comprising:
    a gene encoding an unnatural collagen-like polymer of at least about 30 kD, characterized by comprising a major proportion of amino acids present as triads having glycine as the first amino acid and at least 40 number % of said triads comprising at least one proline, wherein the total proline content of said triads is less than 45 number %; and comprising at least two repetitive units of $(glyXO)_n$, wherein X and O are the same or different in each triad and symbolize individual amino acids and n is at least 4;
    a transcriptional initiation regulatory region functional in a unicellular microorganism 5' of said gene; and
    a transcriptional termination regulatory region functional in a unicellular microorganism 3' of said gene;
    wherein said gene is under the transcriptional regulation of said regulatory regions and wherein said gene is capable of being expressed in a unicellular microorganism from a construct preDared in vitro to provide said collagen-like polymer.

26. A DNA sequence according to claim 25, wherein said gene encodes an unnatural collagen-like polymer comprising at least one repeat of a sequence of the following formula:

$$((glyXO)_n Q)_m$$

wherein:

X and O are any amino acids, except that X and O are selected to provide for a polymer of less than about 45 number % proline;

Ω has from 0 to 50 amino acids and is other than a repetitive glyXO motif;

n is in the range of 4 to 100; and m is at least one.

27. A DNA sequence according to claim 25, wherein said gene encodes a collagen like polymer of the formula:

$$J^1, ((((glyU^u\pi^\pi)_{p2}(glyX^xO^o)_{n1}(glyU^u\pi^\pi)_{p2})\Omega_1)_{m1})J^2_r$$

wherein:

$J^1$ and $J^2$ are the same or different and are amino acid sequences of from about 1 to 50 amino acids;

X and O are any amino acids except that X and O are selected to provide a polymer having a total proline content of less than about 45 number %;

Ω is an amino acid sequence of 0 to 50 amino acids;

x and o indicate the X and O in each triad may be the same or different;

x indicates that the amino acid sequence in each Ω may be the same or different;

U and II are any amino acids;

u and II indicate the same or different amino acids in the individual triads;

$n^1$ is in the range of about 4 to 75, the r's are the same or different and are 0 or 1;

$p^2$ is in the range of 0 to 6; and $m^1$ is in the range of about 1 to 20.

28. A method for producing an unnatural collagen-like polymer of at least about 30 kD, characterized by comprising a major proportion of amino acids present as triads having glycine as the first amino acid and at least 40 number % of said triads comprising at least one proline, wherein the total proline content of said triads is less than 45 number %; and comprising at least two repetitive units of $(glyXO)_n$, wherein X and O are the same or different in each triad and symbolize individual amino acids and n is at least 4;

said method comprising:

growing a unicellular microorganism according to claim 24 for sufficient time for said gene to be expressed; and isolating said collagen like polymer.

29. A formed object comprising an unnatural collagen-like polymer of at least about 30 kD, characterized by:

comprising a major proportion of amino acids present as triads having glycine as the first amino acid and at least 40 number % of said triads comprising at least one proline, wherein the total proline content of said triads is less than 45 number %; and comprising at least two repetitive units of $(glyXO)_n$, wherein X and O are the same or different in each triad and symbolize individual amino acids and n is at least 4, wherein said collagen-like polymer is capable of being exDressed in a unicellular organism from a construct Drepared in vitro.

30. A formed object according to claim 29, wherein said formed object is a gel, film or fiber.

31. An antibody composition prepared in response to a collagen like polymer according to claim 1 or fragment thereof.

32. An antibody composition according to claim 31, wherein said antibody composition is a monoclonal antibody composition.

* * * * *